US011266698B2

(12) United States Patent
Kelly et al.

(10) Patent No.: US 11,266,698 B2
(45) Date of Patent: *Mar. 8, 2022

(54) BACTERIUM FOR USE AS A PROBIOTIC FOR NUTRITIONAL AND MEDICAL APPLICATIONS

(71) Applicant: 4D Pharma Research Limited, Aberdeen (GB)

(72) Inventors: Denise Kelly, Aberdeen (GB); Imke Mulder, Aberdeen (GB)

(73) Assignee: 4D Pharma Research Limited, Aberdeen (GB)

(*) Notice: Subject to any disclaimer, the term of this patent is extended or adjusted under 35 U.S.C. 154(b) by 0 days.

This patent is subject to a terminal disclaimer.

(21) Appl. No.: 15/906,988

(22) Filed: Feb. 27, 2018

(65) Prior Publication Data

US 2018/0271918 A1    Sep. 27, 2018

Related U.S. Application Data

(60) Division of application No. 15/070,605, filed on Mar. 15, 2016, now Pat. No. 9,937,211, which is a continuation of application No. 14/349,907, filed as application No. PCT/GB2012/052495 on Oct. 8, 2012, now Pat. No. 9,314,489.

(30) Foreign Application Priority Data

Oct. 7, 2011 (GB) .................................... 1117313

(51) Int. Cl.
| | |
|---|---|
| *A61K 35/741* | (2015.01) |
| *A61K 35/00* | (2006.01) |
| *A23L 33/135* | (2016.01) |
| *A61K 35/74* | (2015.01) |
| *A23K 10/18* | (2016.01) |
| *C12N 1/20* | (2006.01) |
| *A61K 9/00* | (2006.01) |
| *A61K 45/06* | (2006.01) |

(52) U.S. Cl.
CPC ............ *A61K 35/741* (2013.01); *A23K 10/18* (2016.05); *A23L 33/135* (2016.08); *A61K 9/0053* (2013.01); *A61K 35/74* (2013.01); *A61K 45/06* (2013.01); *C12N 1/20* (2013.01); *A23V 2002/00* (2013.01); *A61K 2035/115* (2013.01)

(58) Field of Classification Search
None
See application file for complete search history.

(56) References Cited

U.S. PATENT DOCUMENTS

| | | |
|---|---|---|
| 3,817,837 A | 6/1974 | Rubenstein et al. |
| 3,850,752 A | 11/1974 | Schuurs et al. |
| 3,939,350 A | 2/1976 | Kronick et al. |
| 3,996,345 A | 12/1976 | Ullman et al. |
| 4,275,149 A | 6/1981 | Litman et al. |
| 4,277,437 A | 7/1981 | Maggio |
| 4,366,241 A | 12/1982 | Tom et al. |
| 4,683,202 A | 7/1987 | Mullis |
| 4,816,567 A | 3/1989 | Cabilly et al. |
| 5,589,168 A | 12/1996 | Allen et al. |
| 5,599,795 A | 2/1997 | McCann et al. |
| 5,674,707 A | 10/1997 | Hintz et al. |
| 5,741,665 A | 4/1998 | Kato et al. |
| 5,925,657 A | 7/1999 | Seed et al. |
| 5,951,977 A | 9/1999 | Nisbet et al. |
| 6,348,452 B1 | 2/2002 | Brown et al. |
| 6,468,964 B1 | 10/2002 | Rowe et al. |
| 6,645,530 B1 | 11/2003 | Borody |
| 7,101,565 B2 | 9/2006 | Monte |
| 7,485,325 B2 | 2/2009 | Swain |
| 7,625,704 B2 | 12/2009 | Fredricks et al. |
| 7,749,494 B2 | 7/2010 | Renaud et al. |
| 7,998,474 B2 | 8/2011 | Kelly |
| 8,197,805 B2 | 6/2012 | Lin et al. |
| 8,287,932 B2 | 10/2012 | Rosales et al. |
| 8,460,648 B2 | 6/2013 | Borody |
| 8,557,233 B2 | 10/2013 | MacSharry et al. |
| 9,011,834 B1 | 4/2015 | Mckenzie et al. |
| 9,314,489 B2 | 4/2016 | Kelly et al. |
| 9,371,510 B2 | 6/2016 | Moore |

(Continued)

FOREIGN PATENT DOCUMENTS

| | | |
|---|---|---|
| CA | 2768301 A | 1/2011 |
| CA | 2768301 A1 | 1/2011 |

(Continued)

OTHER PUBLICATIONS

Ishibashi et al. Mal. J. Nutr. 3: 149-159, 1997.*
Morgan et al. Encyclopedia of Microbiology, Third Edition, 162-173, 2009, abstract.*
Co-pending U.S. Appl. No. 16/022,207, filed Jun. 28, 2018.
Co-pending U.S. Appl. No. 16/022,256, filed Jun. 28, 2018.
Co-pending U.S. Appl. No. 16/022,484, filed Jun. 28, 2018.
Co-pending U.S. Appl. No. 16/022,577, filed Jun. 28, 2018.
Co-pending U.S. Appl. No. 16/031,024, filed Jul. 10, 2018.
Co-pending U.S. Appl. No. 16/040,356, filed Jul. 19, 2018.
U.S. Appl. No. 15/631,945 Office Action dated Jul. 5, 2018.
U.S. Appl. No. 15/631,952 Office Action dated Jul. 19, 2018.
U.S. Appl. No. 15/679,857 Office Action dated Aug. 6, 2018.
U.S. Appl. No. 15/704,245 Office Action dated Sep. 17, 2018.
U.S. Appl. No. 15/842,635 Office Action dated Aug. 27, 2018.

(Continued)

*Primary Examiner* — Sarvamangala Devi

(74) *Attorney, Agent, or Firm* — Wilson Sonsini Goodrich & Rosati

(57) ABSTRACT

A first aspect of the invention relates to the bacterial species *Roseburia hominis* for use in: regulating the immune system of a subject treating an immune disorder; treating an intestinal disorder; improving intestinal microbiota; regulating the innate immune system of a subject; regulating the adaptive immune system of a subject; regulating appetite in a subject; promoting Tregs and immune tolerance; promoting gut health in a subject; and/or maintaining immune homeostasis in a subject. Further aspects of the invention relate to compositions comprising *Roseburia hominis*.

13 Claims, 23 Drawing Sheets

Specification includes a Sequence Listing.

(56) References Cited

U.S. PATENT DOCUMENTS

| | | |
|---|---|---|
| 9,376,473 B2 | 6/2016 | Gleiberman et al. |
| 9,539,293 B2 | 1/2017 | Kelly et al. |
| 9,610,307 B2 | 4/2017 | Berry et al. |
| 9,662,381 B2 | 5/2017 | Honda et al. |
| 9,796,762 B2 | 10/2017 | Kelly et al. |
| 9,808,519 B2 | 11/2017 | Honda et al. |
| 9,839,655 B2 | 12/2017 | Mulder et al. |
| 9,855,302 B2 | 1/2018 | Gajewski et al. |
| 9,937,211 B2 | 4/2018 | Kelly et al. |
| 9,974,815 B2 | 5/2018 | Mulder et al. |
| 9,987,311 B2 | 6/2018 | Mulder et al. |
| 10,046,015 B2 | 8/2018 | Mulder et al. |
| 10,058,574 B2 | 8/2018 | Grant et al. |
| 10,080,772 B2 | 9/2018 | Crouzet et al. |
| 10,086,020 B2 | 10/2018 | Bernalier-Donadille et al. |
| 10,086,021 B2 | 10/2018 | Jeffery et al. |
| 10,086,022 B2 | 10/2018 | Bernalier-Donadille et al. |
| 10,086,023 B2 | 10/2018 | Bernalier-Donadille Annick et al. |
| 10,391,130 B2 | 8/2019 | Grant et al. |
| 2003/0147858 A1 | 8/2003 | Renaud et al. |
| 2004/0005304 A1 | 1/2004 | Brudnak |
| 2004/0106564 A1 | 6/2004 | Nilius et al. |
| 2006/0062774 A1 | 3/2006 | Davis et al. |
| 2006/0073161 A1 | 4/2006 | Breton |
| 2006/0115465 A1 | 6/2006 | Macfarlane et al. |
| 2007/0098744 A1 | 5/2007 | Knorr et al. |
| 2007/0167423 A1 | 7/2007 | Bergauer et al. |
| 2007/0258953 A1 | 11/2007 | Duncan et al. |
| 2007/0286913 A1 | 12/2007 | Swain et al. |
| 2008/0069861 A1 | 3/2008 | Brown et al. |
| 2008/0107634 A1 | 5/2008 | Mogna et al. |
| 2008/0206212 A1 | 8/2008 | Mcmahon et al. |
| 2008/0260906 A1 | 10/2008 | Stojanovic |
| 2008/0299098 A1 | 12/2008 | Se et al. |
| 2009/0217401 A1 | 8/2009 | Korman et al. |
| 2010/0028449 A1 | 2/2010 | Prakash et al. |
| 2010/0047209 A1 | 2/2010 | Stanton et al. |
| 2010/0247489 A1 | 9/2010 | Saur-Brosch |
| 2010/0284973 A1 | 11/2010 | Schiffer-Mannioui Cecile et al. |
| 2010/0303782 A1 | 12/2010 | Cobb et al. |
| 2010/0311686 A1 | 12/2010 | Kasper et al. |
| 2010/0316617 A1 | 12/2010 | Renaud et al. |
| 2010/0316769 A1 | 12/2010 | Czarnecki-Maulden et al. |
| 2011/0053829 A1 | 3/2011 | Baumhof et al. |
| 2011/0086011 A1 | 4/2011 | Kasper et al. |
| 2011/0280840 A1 | 11/2011 | Blaser et al. |
| 2012/0020943 A1 | 1/2012 | Lin |
| 2012/0107279 A1 | 5/2012 | Arigoni et al. |
| 2013/0022575 A1 | 1/2013 | Cassity |
| 2013/0130988 A1 | 5/2013 | Blareau et al. |
| 2013/0195802 A1 | 8/2013 | Moore |
| 2013/0280724 A1 | 10/2013 | Ramadan et al. |
| 2013/0316032 A1 | 11/2013 | Itoh et al. |
| 2013/0336931 A1 | 12/2013 | Wadstroem et al. |
| 2014/0037716 A1 | 2/2014 | Nowill et al. |
| 2014/0056852 A1 | 2/2014 | Guglielmetti et al. |
| 2014/0112897 A1 | 4/2014 | Pyne et al. |
| 2014/0147425 A1 | 5/2014 | Henn et al. |
| 2014/0154218 A1 | 6/2014 | Kohno et al. |
| 2014/0179770 A1 | 6/2014 | Zhang et al. |
| 2014/0193464 A1 | 7/2014 | Lin et al. |
| 2014/0199281 A1 | 7/2014 | Henn et al. |
| 2014/0227227 A1 | 8/2014 | Qin et al. |
| 2014/0328803 A1 | 11/2014 | McKenzie et al. |
| 2014/0335131 A1 | 11/2014 | Mazmanian et al. |
| 2014/0341921 A1 | 11/2014 | Honda et al. |
| 2014/0363397 A1 | 12/2014 | Allen-Vercoe et al. |
| 2015/0044173 A1 | 2/2015 | Jones et al. |
| 2015/0071957 A1 | 3/2015 | Kelly et al. |
| 2015/0104418 A1 | 4/2015 | Flint et al. |
| 2015/0132264 A1 | 5/2015 | Kelly et al. |
| 2015/0284781 A1 | 10/2015 | Klumpp et al. |
| 2016/0058804 A1 | 3/2016 | Jones et al. |
| 2016/0067188 A1 | 3/2016 | Cade et al. |
| 2016/0184370 A1 | 6/2016 | Mckenzie et al. |
| 2016/0199424 A1 | 7/2016 | Berry et al. |
| 2016/0223553 A1 | 8/2016 | Sears et al. |
| 2016/0235792 A1 | 8/2016 | Berry et al. |
| 2017/0143772 A1 | 5/2017 | Mulder et al. |
| 2017/0143773 A1 | 5/2017 | Mulder et al. |
| 2017/0143774 A1 | 5/2017 | Mulder et al. |
| 2017/0143775 A1 | 5/2017 | Mulder et al. |
| 2017/0173089 A1 | 6/2017 | Kelly |
| 2017/0319634 A1 | 11/2017 | Grant et al. |
| 2017/0326184 A1 | 11/2017 | Patterson et al. |
| 2017/0326202 A1 | 11/2017 | Kelly |
| 2017/0354695 A1 | 12/2017 | Grant et al. |
| 2017/0360856 A1 | 12/2017 | Grant et al. |
| 2017/0368110 A1 | 12/2017 | Grant et al. |
| 2018/0055892 A1 | 3/2018 | Mulder et al. |
| 2018/0072778 A1 | 3/2018 | Kelly et al. |
| 2018/0078585 A1 | 3/2018 | Mulder et al. |
| 2018/0078587 A1 | 3/2018 | Crott et al. |
| 2018/0133265 A1* | 5/2018 | Stevenson ............... A61K 9/19 |
| 2018/0344780 A1 | 12/2018 | Grant et al. |
| 2019/0099458 A1 | 4/2019 | Grant et al. |

FOREIGN PATENT DOCUMENTS

| | | |
|---|---|---|
| CN | 1863540 A | 11/2006 |
| CN | 1917946 A | 2/2007 |
| CN | 1954066 A | 4/2007 |
| CN | 101590081 A | 12/2009 |
| CN | 102304483 A | 1/2012 |
| CN | 102031235 B | 7/2012 |
| CN | 102093967 B | 1/2013 |
| CN | 102905558 A | 1/2013 |
| CN | 102940652 A | 2/2013 |
| CN | 201180025408 | 2/2013 |
| CN | 102373172 B | 3/2013 |
| CN | 103037876 A | 4/2013 |
| CN | 103142656 A | 6/2013 |
| CN | 103146620 A | 6/2013 |
| CN | 103156888 A | 6/2013 |
| CN | 103652322 A | 3/2014 |
| CN | 103781487 A | 5/2014 |
| CN | 103820363 A | 5/2014 |
| CN | 103849590 A | 6/2014 |
| CN | 103865846 A | 6/2014 |
| CN | 103930117 A | 7/2014 |
| CN | 103981115 A | 8/2014 |
| CN | 103981117 A | 8/2014 |
| CN | 104160014 A | 11/2014 |
| CN | 104195075 A | 12/2014 |
| CN | 103509741 B | 2/2015 |
| CN | 102940652 B | 3/2015 |
| CN | 104435000 A | 3/2015 |
| CN | 103037876 B | 4/2015 |
| CN | 104546932 A | 4/2015 |
| CN | 104546933 A | 4/2015 |
| CN | 104546934 A | 4/2015 |
| CN | 104546935 A | 4/2015 |
| CN | 104546940 A | 4/2015 |
| CN | 104546942 A | 4/2015 |
| CN | 104560820 A | 4/2015 |
| CN | 201410522408 | 4/2015 |
| CN | 105112333 A | 12/2015 |
| CN | 103820363 B | 2/2016 |
| CN | 103865846 B | 3/2016 |
| CN | 105982919 A | 10/2016 |
| DE | 19826928 A1 | 12/1999 |
| DE | 10206995 A1 | 9/2003 |
| EP | 0120516 A2 | 10/1984 |
| EP | 0238023 A2 | 9/1987 |
| EP | 0433299 A1 | 6/1991 |
| EP | 0449375 A2 | 10/1991 |
| EP | 0581171 A1 | 2/1994 |
| EP | 0778778 A1 | 6/1997 |
| EP | 0888118 A1 | 1/1999 |
| EP | 1141235 A2 | 10/2001 |
| EP | 1227152 A1 | 7/2002 |
| EP | 1383514 A1 | 1/2004 |
| EP | 1448995 A1 | 8/2004 |

(56) References Cited

FOREIGN PATENT DOCUMENTS

| | | |
|---|---|---|
| EP | 1481681 A1 | 12/2004 |
| EP | 1765391 A1 | 3/2007 |
| EP | 1675481 B1 | 11/2008 |
| EP | 1997499 A1 | 12/2008 |
| EP | 1997905 A1 | 12/2008 |
| EP | 1997906 A1 | 12/2008 |
| EP | 1997907 A1 | 12/2008 |
| EP | 2044436 A2 | 4/2009 |
| EP | 2103226 A1 | 9/2009 |
| EP | 2133088 A3 | 1/2010 |
| EP | 1280541 B2 | 3/2010 |
| EP | 2236598 A1 | 10/2010 |
| EP | 2286832 A1 | 2/2011 |
| EP | 2308498 A1 | 4/2011 |
| EP | 2217253 B1 | 6/2011 |
| EP | 1940243 B1 | 8/2011 |
| EP | 2359838 A1 | 8/2011 |
| EP | 1855550 B1 | 10/2011 |
| EP | 1871400 B1 | 10/2011 |
| EP | 2124972 B1 | 6/2012 |
| EP | 1773361 B2 | 9/2012 |
| EP | 1945234 B1 | 12/2012 |
| EP | 2323493 B8 | 12/2012 |
| EP | 2323494 B8 | 12/2012 |
| EP | 1629850 B2 | 5/2013 |
| EP | 2203551 B1 | 8/2013 |
| EP | 2140771 B1 | 12/2013 |
| EP | 2687227 A1 | 1/2014 |
| EP | 2179028 B1 | 8/2014 |
| EP | 2650002 A4 | 8/2014 |
| EP | 2164349 B1 | 9/2014 |
| EP | 2134835 B1 | 10/2014 |
| EP | 2810652 A2 | 12/2014 |
| EP | 2305838 B1 | 1/2015 |
| EP | 2832859 A1 | 2/2015 |
| EP | 3307288 A1 | 4/2018 |
| ES | 2408279 A2 | 6/2013 |
| JP | H08259450 A | 10/1996 |
| JP | 2003261453 A | 9/2003 |
| JP | 2005097280 A | 4/2005 |
| JP | 2006265212 A | 10/2006 |
| JP | 2007084533 A | 4/2007 |
| JP | 2007116991 A | 5/2007 |
| JP | 2008195635 A | 8/2008 |
| JP | 2009507023 A | 2/2009 |
| JP | 2010246523 A | 11/2010 |
| JP | 5031249 B2 | 9/2012 |
| JP | 2013005759 A | 1/2013 |
| JP | 5183848 B2 | 4/2013 |
| JP | 2013527240 A | 6/2013 |
| JP | 2013201912 A | 10/2013 |
| JP | 2014196260 A | 10/2014 |
| JP | 2014534957 A | 12/2014 |
| JP | 2015500792 A | 1/2015 |
| JP | 5710876 B2 | 4/2015 |
| JP | 5792105 B2 | 10/2015 |
| KR | 100468522 B1 | 1/2005 |
| KR | 20100128168 A | 12/2010 |
| KR | 1020100128168 | 12/2010 |
| KR | 101017448 B1 | 2/2011 |
| KR | 101057357 B1 | 8/2011 |
| KR | 20130021764 A | 3/2013 |
| KR | 101250463 B1 | 4/2013 |
| KR | 20140037544 A | 3/2014 |
| KR | 20140061328 A | 5/2014 |
| PL | 229020 B1 | 5/2018 |
| RU | 2078815 C1 | 5/1997 |
| TW | I417054 B | 12/2013 |
| WO | WO-8807865 A1 | 10/1988 |
| WO | WO-9117243 A1 | 11/1991 |
| WO | WO-9611014 A1 | 4/1996 |
| WO | WO-9720577 A1 | 6/1997 |
| WO | WO-9730717 A1 | 8/1997 |
| WO | WO-9735956 A1 | 10/1997 |
| WO | WO-9843081 A1 | 10/1998 |
| WO | WO-9855131 A1 | 12/1998 |
| WO | WO-9857631 A1 | 12/1998 |
| WO | WO-9919459 A1 | 4/1999 |
| WO | WO-9942568 A1 | 8/1999 |
| WO | WO-9945955 A1 | 9/1999 |
| WO | WO-0116120 A1 | 3/2001 |
| WO | WO-0158275 A2 | 8/2001 |
| WO | WO-0185187 A1 | 11/2001 |
| WO | WO-0193904 A1 | 12/2001 |
| WO | WO-0207741 A1 | 1/2002 |
| WO | WO-0242328 A2 | 5/2002 |
| WO | WO-02070670 A1 | 9/2002 |
| WO | WO-02085933 A1 | 10/2002 |
| WO | WO-02094296 A1 | 11/2002 |
| WO | WO-03010297 A1 | 2/2003 |
| WO | WO-03022255 A1 | 3/2003 |
| WO | WO-03045317 A2 | 6/2003 |
| WO | WO-03046580 A1 | 6/2003 |
| WO | WO-03053220 A2 | 7/2003 |
| WO | WO-2004003235 A3 | 6/2004 |
| WO | WO-2004085628 A1 | 10/2004 |
| WO | WO-2005007834 A1 | 1/2005 |
| WO | WO-2005030133 A2 | 4/2005 |
| WO | WO-2005032567 A2 | 4/2005 |
| WO | WO-2005058335 A1 | 6/2005 |
| WO | WO-2005032567 A3 | 7/2005 |
| WO | WO-2005093049 A1 | 10/2005 |
| WO | WO-2005107381 A2 | 11/2005 |
| WO | WO-2005121130 A2 | 12/2005 |
| WO | WO-2006012586 A2 | 2/2006 |
| WO | WO-2006033949 A1 | 3/2006 |
| WO | WO-2006033950 A1 | 3/2006 |
| WO | WO-2006033951 A1 | 3/2006 |
| WO | WO-2006054135 A1 | 5/2006 |
| WO | WO-2006102350 A1 | 9/2006 |
| WO | WO-2006102536 A2 | 9/2006 |
| WO | WO-2006091103 A3 | 10/2006 |
| WO | WO-2006110406 A2 | 10/2006 |
| WO | WO-2006130205 A1 | 12/2006 |
| WO | WO-2007027761 A2 | 3/2007 |
| WO | WO-2007039313 A2 | 4/2007 |
| WO | WO-2007056218 A2 | 5/2007 |
| WO | WO-2007064732 A1 | 6/2007 |
| WO | WO-2007064749 A1 | 6/2007 |
| WO | WO-2007098371 A2 | 8/2007 |
| WO | WO-2007126990 A2 | 11/2007 |
| WO | WO-2007136719 A2 | 11/2007 |
| WO | WO-2007140230 A3 | 2/2008 |
| WO | WO-2008031438 A3 | 5/2008 |
| WO | WO-2008055702 A1 | 5/2008 |
| WO | WO-2008055703 A2 | 5/2008 |
| WO | WO-2008064489 A1 | 6/2008 |
| WO | WO-2008073148 A2 | 6/2008 |
| WO | WO-2008076696 A2 | 6/2008 |
| WO | WO-2008053444 A3 | 7/2008 |
| WO | WO-2008083157 A2 | 7/2008 |
| WO | WO-2008134450 A2 | 11/2008 |
| WO | WO-2008153377 A1 | 12/2008 |
| WO | WO-2009027753 A1 | 3/2009 |
| WO | WO-2009030481 A1 | 3/2009 |
| WO | WO-2009055362 A1 | 4/2009 |
| WO | WO-2009059284 A1 | 5/2009 |
| WO | WO-2009072889 A1 | 6/2009 |
| WO | WO-2009079564 A2 | 6/2009 |
| WO | WO-2009043856 A3 | 7/2009 |
| WO | WO-2009080862 A1 | 7/2009 |
| WO | WO-2009100331 A1 | 8/2009 |
| WO | WO-2009116864 A1 | 9/2009 |
| WO | WO-2009128949 A2 | 10/2009 |
| WO | WO-2009138220 A1 | 11/2009 |
| WO | WO-2009149149 A1 | 12/2009 |
| WO | WO-2009151315 A1 | 12/2009 |
| WO | WO-2009154463 A2 | 12/2009 |
| WO | WO-2009156301 A1 | 12/2009 |
| WO | WO-2010002241 A1 | 1/2010 |
| WO | WO-2010036876 A2 | 4/2010 |
| WO | WO-2010037402 A1 | 4/2010 |
| WO | WO-2010037408 A1 | 4/2010 |
| WO | WO-2010037539 A1 | 4/2010 |

(56) References Cited

FOREIGN PATENT DOCUMENTS

| | | |
|---|---|---|
| WO | WO-2010048481 A1 | 4/2010 |
| WO | WO-2010063601 A1 | 6/2010 |
| WO | WO-2010081126 A3 | 9/2010 |
| WO | WO-2010129839 A1 | 11/2010 |
| WO | WO-2010130659 A1 | 11/2010 |
| WO | WO-2010130660 A1 | 11/2010 |
| WO | WO-2010130662 A1 | 11/2010 |
| WO | WO-2010130663 A1 | 11/2010 |
| WO | WO-2010130697 A1 | 11/2010 |
| WO | WO-2010130699 A1 | 11/2010 |
| WO | WO-2010130700 A1 | 11/2010 |
| WO | WO-2010130701 A1 | 11/2010 |
| WO | WO-2010130702 A1 | 11/2010 |
| WO | WO-2010130704 A1 | 11/2010 |
| WO | WO-2010130710 A1 | 11/2010 |
| WO | WO-2010130713 A1 | 11/2010 |
| WO | WO-2010/143940 | 12/2010 |
| WO | WO-2010139531 A1 | 12/2010 |
| WO | WO-2010142504 A1 | 12/2010 |
| WO | WO-2010143961 A1 | 12/2010 |
| WO | WO-2010147714 A1 | 12/2010 |
| WO | WO-2010133475 A3 | 1/2011 |
| WO | WO-2011000620 A1 | 1/2011 |
| WO | WO-2011000621 A1 | 1/2011 |
| WO | WO-2011005756 A1 | 1/2011 |
| WO | WO-2010133472 A3 | 2/2011 |
| WO | WO-2011020748 A1 | 2/2011 |
| WO | WO-2011036539 A1 | 3/2011 |
| WO | WO-2011043654 A1 | 4/2011 |
| WO | WO-2011044208 A1 | 4/2011 |
| WO | WO-2011058535 A1 | 5/2011 |
| WO | WO-2011075138 A1 | 6/2011 |
| WO | WO-2011096808 A1 | 8/2011 |
| WO | WO-2011096809 A1 | 8/2011 |
| WO | WO-2011110918 A1 | 9/2011 |
| WO | WO-2011121379 A1 | 10/2011 |
| WO | WO-2011149335 A1 | 12/2011 |
| WO | WO-2011152566 A2 | 12/2011 |
| WO | WO-2011153226 A2 | 12/2011 |
| WO | WO-2011157816 A1 | 12/2011 |
| WO | WO-2012012874 A1 | 2/2012 |
| WO | WO-2012016287 A2 | 2/2012 |
| WO | WO-2012024638 A2 | 2/2012 |
| WO | WO-2011153226 A3 | 3/2012 |
| WO | WO-2012055408 A1 | 5/2012 |
| WO | WO-2012062780 A1 | 5/2012 |
| WO | WO-2012071380 A1 | 5/2012 |
| WO | WO-2012076739 A1 | 6/2012 |
| WO | WO-2012105312 A1 | 8/2012 |
| WO | WO-2012122478 A1 | 9/2012 |
| WO | WO-2012140636 A1 | 10/2012 |
| WO | WO-2012142605 A1 | 10/2012 |
| WO | WO-2012145491 A2 | 10/2012 |
| WO | WO-2012158517 A1 | 11/2012 |
| WO | WO-2012165843 A2 | 12/2012 |
| WO | WO-2012170478 A2 | 12/2012 |
| WO | WO-2013005836 A1 | 1/2013 |
| WO | WO-2013008039 A2 | 1/2013 |
| WO | WO-2013008102 A2 | 1/2013 |
| WO | WO-2013037068 A1 | 3/2013 |
| WO | WO-2013050792 A1 | 4/2013 |
| WO | WO-2013053836 A1 | 4/2013 |
| WO | WO-2013063849 A1 | 5/2013 |
| WO | WO-2013080561 A1 | 6/2013 |
| WO | WO-2013124725 A1 | 8/2013 |
| WO | WO-2013144701 A1 | 10/2013 |
| WO | WO-2013153358 A1 | 10/2013 |
| WO | WO-2013154725 A1 | 10/2013 |
| WO | WO-2013171515 A1 | 11/2013 |
| WO | WO-2013175038 A1 | 11/2013 |
| WO | WO-2013181694 A1 | 12/2013 |
| WO | WO-2013182038 A1 | 12/2013 |
| WO | WO-2014001368 A1 | 1/2014 |
| WO | WO-2014019271 A1 | 2/2014 |
| WO | WO-2014020004 A1 | 2/2014 |
| WO | WO-2014032108 A1 | 3/2014 |
| WO | WO-2014036182 A2 | 3/2014 |
| WO | WO-2014043593 A2 | 3/2014 |
| WO | WO-2014053608 A1 | 4/2014 |
| WO | WO-2014064359 A1 | 5/2014 |
| WO | WO-2014067976 A1 | 5/2014 |
| WO | WO-2014070014 A1 | 5/2014 |
| WO | WO-2014070225 A1 | 5/2014 |
| WO | WO-2014075745 A1 | 5/2014 |
| WO | WO-2014078911 A1 | 5/2014 |
| WO | WO-2014082050 A1 | 5/2014 |
| WO | WO-2014093622 A2 | 6/2014 |
| WO | WO-2014093635 A1 | 6/2014 |
| WO | WO-2014093655 A2 | 6/2014 |
| WO | WO-2014121298 A2 | 8/2014 |
| WO | WO-2014121301 A1 | 8/2014 |
| WO | WO-2014121302 A2 | 8/2014 |
| WO | WO-2014121304 A1 | 8/2014 |
| WO | WO-2014130540 A1 | 8/2014 |
| WO | WO-2014137211 A1 | 9/2014 |
| WO | WO-2014145958 A2 | 9/2014 |
| WO | WO-2014150094 A1 | 9/2014 |
| WO | WO-2014152338 A1 | 9/2014 |
| WO | WO-2014153194 A2 | 9/2014 |
| WO | WO-2014121302 A3 | 10/2014 |
| WO | WO-2014167338 A1 | 10/2014 |
| WO | WO-2014182966 A1 | 11/2014 |
| WO | WO-2014200334 A1 | 12/2014 |
| WO | WO-2014201037 A2 | 12/2014 |
| WO | WO-2015003001 A1 | 1/2015 |
| WO | WO-2015006355 A2 | 1/2015 |
| WO | WO-2015013214 A2 | 1/2015 |
| WO | WO-2015017625 A1 | 2/2015 |
| WO | WO-2015021936 A1 | 2/2015 |
| WO | WO-2015033305 A1 | 3/2015 |
| WO | WO-2015038731 A1 | 3/2015 |
| WO | WO-2015057151 A1 | 4/2015 |
| WO | WO-2015077794 A1 | 5/2015 |
| WO | WO-2015095241 A2 | 6/2015 |
| WO | WO-2015077794 A4 | 7/2015 |
| WO | WO-2015156419 A1 | 10/2015 |
| WO | WO-2015156519 A1 | 10/2015 |
| WO | WO-2015168534 A1 | 11/2015 |
| WO | WO-2015169944 A1 | 11/2015 |
| WO | WO-2015095241 A4 | 12/2015 |
| WO | WO-2016019505 A1 | 2/2016 |
| WO | WO-2016019506 A1 | 2/2016 |
| WO | WO-2016033439 A2 | 3/2016 |
| WO | WO-2016036615 A1 | 3/2016 |
| WO | WO-2016057671 A1 | 4/2016 |
| WO | WO-2016065324 A1 | 4/2016 |
| WO | WO-2016069795 A2 | 5/2016 |
| WO | WO-2016069801 A1 | 5/2016 |
| WO | WO-2016070151 A1 | 5/2016 |
| WO | WO-2016086161 A1 | 6/2016 |
| WO | WO-2016086205 A2 | 6/2016 |
| WO | WO-2016086206 A1 | 6/2016 |
| WO | WO-2016086208 A1 | 6/2016 |
| WO | WO-2016086209 A1 | 6/2016 |
| WO | WO-2016086210 A1 | 6/2016 |
| WO | WO-2016102950 A1 | 6/2016 |
| WO | WO-2016102951 A1 | 6/2016 |
| WO | WO-2016118730 A1 | 7/2016 |
| WO | WO-2016139217 A1 | 9/2016 |
| WO | WO-2016149449 A1 | 9/2016 |
| WO | WO-2016149687 A1 | 9/2016 |
| WO | WO-2016203218 A1 | 12/2016 |
| WO | WO-2016203220 A1 | 12/2016 |
| WO | WO-2016203221 A1 | 12/2016 |
| WO | WO-2017079450 A1 | 5/2017 |
| WO | WO-2017085520 A1 | 5/2017 |
| WO | WO-2017091753 A1 | 6/2017 |
| WO | WO-2017148596 A1 | 9/2017 |
| WO | WO-2017160711 A1 | 9/2017 |
| WO | WO-2018011594 A1 | 1/2018 |
| WO | WO-2018047106 A1 | 3/2018 |
| WO | WO-2018/112365 A2 | 6/2018 |
| WO | WO-2018112363 | 6/2018 |

(56) References Cited

FOREIGN PATENT DOCUMENTS

| WO | WO-2018112363 A1 | 6/2018 |
|---|---|---|
| WO | WO-2018112365 A2 | 6/2018 |
| WO | WO-2018215782 A1 | 11/2018 |

OTHER PUBLICATIONS

Altschul et al. 'Basic local alignment search tool.' Journal of Molecular Biology. 1990, vol. 215, No. 3, pp. 403-410.
"Amedei, A. et al. Multiple sclerosis: the role of cytokines in pathogenesis and in therapies. Int J Mol Sci. Oct. 19, 2012;13(10):13438-60. doi: 10.3390/ijms131013438."
Aminov et al. Molecular diversity, cultivation, and improved detection by fluorescent in situ hybridization of a dominant group of human gut bacteria related to Roseburia spp. or Eubacterium rectale. Applied and environmental microbiology. 2006, vol. 7 2, No. 9, pp. 6371-6376.
An et al. (1985) "New cloning vehicles for transformation of higher plants," EMBO J. 4:277-284.
An et al. (1988) "Binary Vectors," Plant Molecular Biology Manual. A3:1-19.
An et al. Transformation of Tobacco, Tomato, Potato, and *Arabiodopsis thaliana* Using a Binary Ti Vector System,Plant Physiol. May 1986; 81:301-305.
Archer et al. (1997) "The Molecular Biology of Secreted Enzyme Production by Fungi," Critical Reviews Biotechnology. 17(4):273-306.
Atarashi et al. Induction of colonic regulatory T cells by indigenous *Clostridium* species. Science 331(6015):337-341 (2011).
Atlas, R. Handbook of Microbiological Media, Fourth Edition. CRC Press. 2010.
Ausubel et al. (1999) Short Protocols in Molecular Biology. 4th edition, pp. 7-58 to 7-60, and Chapter 18. pp. 18-1 to 18-23.
Ausubel, et al. Current Protocols in Molecular Biology. 1987. Supplement 30.
Ausubel et al., Short protocols in molecular biology. Fifth edition, 2002.
Azad, M.B. et al., Probiotic supplementation during pregnancy or infancy for the prevention of asthma and wheeze: systematic review and meta-analysis BMJ 2013; 347 :f6471.
Aziz et al. The RAST Server: rapid annotations using subsystems technology. BMC Genomics. 2008, vol. 9, No. 1, pp. 75.
Balato, et al., Effects of adalimumab therapy in adult subjects with moderate-to-severe psoriasis on Th17 pathway. (2014) J Eur Acad Dermatol Venereol. 28(8):1016-24.
Barcenilla et al. "Phylogenetic relationships of butyrate-producing bacteria from the human gut" Applied and environmental microbiology. 2000, vol. 66, No. 4, pp. 1654-1661.
Beggs (1978) "Transformation of yeast by a replicating hybrid plasmid," Nature. 275:104-109.
Berg et al. (1996) "Enterocolitis and colon cancer in interleukin-10-deficient mice are associated with aberrant cytokine production and CD4(+) TH1-like responses," The Journal of Clinical Investigation. 98(4):1010-1020.
Birdi, K.S. Handbook of Surface and Colloid Chemistry, 2nd Edition. CRC Press. 1997.
Brand et al., Collagen-induced arthritis, 2007; Protocol 2(5):1269-1275.
Brasel et al. (2000) "Generation of murine dendritic cells from ftl3-ligand-supplemented bone marrow cultures," Blood. 96(9):3029-3039.
Butcher et al. (1980) The role of tissue culture in the study of crown-gall tumorigenesis. Tissue Culture Methods for Plant Pathologists. Eds.: Ingrams, D. S.; Helgeson, J.P. pp. 203-208.
Carvalho et al. (Jan. 2011) "TLR5 activation induces secretory interleukin-1 receptor antagonist (sll-1 Ra) and reduces inflammasome-associated tissue damage," Nature. 4(1 ):102-111.

Cereghino et al. (2000) "Heterologous protein expression in the methylotrophic yeast *Pichia pastoris,*" FEMS Microbiol Review. 24(1 ):45-66.
Cheluvappa, R. et al., T helper type 17 pathway suppression by appendicitis and appendectomy protects against colitis. Clin Exp Immunol. Feb. 2014;175(2):316-22. doi: 10.1111/cei.12237.
Chevreux et al. 'Genome sequence assembly using trace signals and additional sequence information.' German Conference on Bioinformatics. 1999.
Chothia et al. The relation between the divergence of sequence and structure in proteins. EMBO Journal. 1986, 5(4):823-826.
Christou (1994) "Genetic engineering of crop legumes and cereals: current status and recent advances," Agro-Food Industry Hi-Tech. pp. 17-27.
Chung et al. 'Microbiota-stimulated immune mechanisms to maintain gut homeostasis.' Current Opinion in Immunology. 2010, vol. 22, No. 4, pp. 455-460.
Colowick, S. and Kaplan, N., Methods of Enzymology. Academic Press, Inc.
Co-pending U.S. Appl. No. 15/359,144, filed Nov. 22, 2016.
Co-pending U.S. Appl. No. 15/915,885, filed Mar. 8, 2018.
Co-pending U.S. Appl. No. 15/915,889, filed Mar. 8, 2018.
Co-pending U.S. Appl. No. 15/916,167, filed Mar. 8, 2018.
Co-pending U.S. Appl. No. 15/916,202, filed Mar. 8, 2018.
Co-pending U.S. Appl. No. 15/916,205, filed Mar. 8, 2018.
Co-pending U.S. Appl. No. 15/969,543, filed May 2, 2018.
Crellin et al. (2005) "Human CD4+ T cells express TLR5 and its ligand ftagellin enhances the suppressive capacity and expression of FOXP3 in CD4+CD25+ T regulatory cells," Journal of Immunology. 175(12):8051-8059.
Davis et al., Genetic and Microbiological Research Techniques, Methods Enzymol. 1970; 17A:79-143.
Day, J.G. et al., Cryopreservation and Freeze-Drying Protocols. Springer. 2007. 2nd edition.
De Paepe et al. 'Trade-off between bile resistance and nutritional competence drives *Escherichia coli* diversification in the mouse gut.' PLoS Genetics. 2011, vol. 7, No. 6, e1002107.
Dennis et al. 'DAVID: database for annotation, visualization, and integrated discovery.' Genome Bioi. 2003, vol. 4, No. 5, p. 3.
Duck et al. 'Isolation of flagellated bacteria implicated in Crohn's disease.' Inflammatory Bowel Diseases. 2007, vol. 13, No. 10, pp. 1191-1201.
Duncan et al. (2002) "*Roseburia intestinal* is sp. nov., a novel saccharolytic, butyrate-producing bacterium from human faeces," International Journal System Evolutionary Microbiology. 52:1615-1620.
Duncan et al. (2006) "Proposal of *Roseburia faecis* sp. nov., *Roseburia hominis* sp. nov. and *Roseburia inulinivorans* sp. nov., based on isolates from human faeces," International Journal of Systematic and Evolutionary Microbiology. Vol. 56, No. Pt 10, pp. 2437-2441.
Duncan et al. "Lactate-utilizing bacteria, isolated from human feces, that produce butyrate as a major fermentation product" Applied and environmental microbiology. 2004, vol. 70, No. 10, pp. 5810-5817.
Eckburg, PB. et al., Diversity of the human intestinal microbial flora.Science. Jun. 10, 2005;308(5728):1635-8. Epub Apr. 14, 2005.
Elkins et al. 'Genes encoding bile salt hydrolases and conjugated bile salt transporters in *Lactobacillus johnsonii* 100-100 and other *Lactobacillus* species.' Microbiology. 2001, vol. 147, No. 12, pp. 3403-3412.
Ely et al. (2000) "A family of six flagellin genes contributes to the Caulobacter crescentus flagellar filament," Journal of Bacteriology. 182(17):5001-5004.
Extended European search report and opinion dated Aug. 23, 2016 for EP Application No. 16166001.4.
Fabro, A. et al., The Th17 pathway in the peripheral lung microenvironment interacts with expression of collagen V in the late state of experimental pulmonary fibrosis. (2015) Immunobiology. 220(1):124-35.
Fahy, J.V. Eosinophilic and neutrophilic inflammation in asthma: insights from clinical studies. Proc Am Thorac Soc. May 1, 2009;6(3):256-9. doi: 10.1513/pats.200808-087RM.

(56) References Cited

OTHER PUBLICATIONS

Falony et al. In vitro kinetics of prebiotic inulin-type fructan fermentation by butyrate-producing colon bacteria: Implementation of online gas chromatography for quantitative analysis of carbon dioxide and hydrogen gas production. Applied and Environmental Microbiology. 2009, vol. 75, No. 18, pp. 5884-5892.
FDA Orphan Drug Designations. Total Orphan Drugs website. Aug. 2014. Available at http://www.orphan-drugs.org/2014/09/01/fda-orphandrug- designations-august-2014. Accessed on Apr. 13, 2016.
Flores-Langarica et al. (2012) "Systemic flagellin immunization stimulates mucosal CD1 03+ dendritic cells and drives Foxp3+ regulatory T Cell and IgA responses in the mesenteric lymph node," Journal of Immunology. 189 (12):57 45-5754.
Fraley et al. (1986) "Genetic Transformation in Higher Plants," Critical Reviews Plant Science. 4:1-46.
Frame et al., Production offertile transgenic maize plants by silicon carbide whisker-mediated transformation, The Plant Journal. 1994; 6:941-948.
Frank, D. et al., Molecular-phylogenetic characterization of microbial community imbalances in human inflammatory bowel diseases. 2007. PNAS. 104(34):13780-5.
Gaboriau-Routhiau et al. 'The key role of segmented filamentous bacteria in the coordinated maturation of gut helper T cell responses.' Immunity. 2009, vol. 31, No. 4, pp. 677-689.
Gait, M.J., (1984) Oligonucleotide Synthesis: A Practical Approach. Irl Press, pp. vii-xiii.
GB Search and Exam report dated Apr. 20, 2016 for GB application 1510468.0.
GenBank Accession No. ABI48297.1 (Jul. 20, 2007) "Fia1 flagellin [*Roseburia hominis*]".
GenBank Accession No. ABY J02000000 (Nov. 8, 2013) Version 2. "Roseburia intestinal is L 1-82, whole genome shotgun sequencing project".
GenBank Accession No.'s ABY J02000001-ABY J02000409 search results page (Last Updated Apr. 24, 2015).
GenBank accession No. AJ312385 (Oct. 9, 2002) "Roseburia intestinalis 16S rRNA gene, strain L1-82".
GenBank Accession No. CP003040 (Aug. 5, 2011) Version 1. "Roseburia Hominis A2-183, complete genome".
GenBank Accession No. DQ789141. (Jul. 20, 2007) "Roseburia horn in is Fla2 flagellin gene".
GenBank Accession No. M20983. (Apr. 26, 1993) "R.cecicola ftagellin gene".
Gennaro, A.R. "Quality Assurance and Control," from Remington: The Science and Practice of Pharmacy, 2000, Lippincott Williams & Wilkins, 20th ed., pp. 980-983.
Gennaro, A.R., Remington's Pharmaceutical sciences, Mack publishin co. 1985.
Geraedts et al. 'Release of satiety hormones in response to specific dietary proteins is different between human and murine small intestinal mucosa.' Annals of Nutrition and Metabolism. 2010, vol. 56, No. 4, pp. 3018-3313.
Geuking et al. 'Intestinal bacterial colonization induces mutualistic regulatory T cell responses.' Immunity. 2011, vol. 34, No. 5, pp. 794-806.
Gewirtz et al. (2001) Cutting edge: bacterial flagellin activates basolaterally expressed TLR5 to induce epithelial proinflammatory gene expression. The Journal of Immunology. 167:(4)1882-1885.
Giraud et al. 'Dissecting the genetic components of adaptation of *Escherichia coli* to the mouse gut.' PLoS Genetics.2008, vol. 4, No. 1, pp. e2.
Goldin, B.R et al., Clinical indications for probiotics: an overview. Clin Infect Dis. Feb. 1, 2008;46 Suppl 2:S96-100; discussion S144-51. doi: 10.1086/523333.
Greenspan et al., Defining epitopes: It's not as easy as it seems. Nature Biotechnology 7: 936-937, 1999.
Hapfelmeier et al. 'Reversible microbial colonization of germ-free mice reveals the dynamics of IgA immune responses.' Science. 2010, vol. 328, No. 5986, pp. 1705-1709.

Hayashi et al. The innate immune response to bacterial ftagellin is mediated by Toll-like receptors. Nature. 2001, vol. 410, No. 6832, pp. 1099-1103.
Hedayat et al. (Mar. 1, 2012) "Prophylactic and therapeutic implications of toll-like receptor ligands," Medicinal Research Reviews. 32(2):294-325.
Higgins, et al. CLUSTAL: A Package for Performing Multiple Sequence Alignment on a Microcomputer. Gene. 73 (1988): 237-244.
Hinchliffe (1993) "Yeast as a vehicle for the expression of heterologous genes," Yeasts. 2nd edition. Rose, A. R.; Harrison, J. H.: Eds. Academic Press Ltd. 5(9). pp. 325-356.
Hinnen et al., Transformation of yeast, Proc. Natl. Acad. Sci. USA. Apr. 1978; 75:1929-1933.
HOEKEMA (1985) The Binary Plant Vector System Offsetdrukkerij Kanters BB, Alblasserdam. Chapter V. pp. 63-71.
Hold et al. 'Oligonucleotide probes that detect quantitatively significant groups of butyrateproducing bacteria in human feces.' Applied and environmental microbiology. 2003, vol. 69, No. 7, pp. 4320-4324.
Holland et al. (1990) "Secretion of Heterologous Proteins in *Escherichia coli*," Methods Enzymology. 182:132-143.
Hollenberg et al. (1997) "Production of recombinant proteins by methulotrophic yeasts," Current Opinion Biotechnology. 8(5):554-560.
Hooper at al. 'Molecular analysis of commensal host-microbial relationships in the intestine.' Science. 2001; vol. 291, No. 5505, pp. 881-884.
Hossain et al. "Flagellin, a TLR5 agonist, reduces graft-versus-host disease in allogeneic hematopoietic stem cell transplantation recipients while enhancing antiviral immunity," Journal of Immunology. Nov. 2011; 187(10): p. 5130-5140.
Hoyles L. et al. Gastrointestinal Tract, Chapter 56. Handbook of Hydrocarbon and Lipid Microbiology Springer Verlag Berlin 2010, 3120-32.
Ibrahim et al., "Method for the isolation of highly purified *Salmonella* flagellins," Journal of Clinical Microbiology. Dec. 1985; 22(6):1040-1044.
Inaba et al., "Generation of large numbers of dendritic cells from mouse bone marrow cultures supplemented with granulocyte/ macrophage colony-stimulating factor," J. Exp. Med. Dec. 1992; 176(6):1693-1702.
Interational Search Report for International Application No. PCT/GB2012/052495, dated Mar. 25, 2013.
International Preliminary Report on Patentability corresponding to International Patent Application No. PCT/GB2014/051123, datedn Oct. 13, 2015.
International Search Report dated Aug. 21, 2014 for International Application No. PCT/GB2014/051123.
International Search Report dated Aug. 26, 2016 for International application No. PCT/GB2016/051774.
Ito et al. (1983) "Transformation of Intact Yeast Cells Treated with Alkali Cations," J. Bacteriology. 153:163-168.
Ivanov et al. 'Induction of intestinal Th17 cells by segmented filamentous bacteria.' Cell. 2009, vol. 139, No. 3, pp. 485-498.
Jarchum et al., "Toll-Like Receptor 5 Stimulation Protects Mice from Acute Clostridium difficile Colitis," Infection and Immunity. Apr. 2011; 79(4):1498-1503.
Jiao et al., Blockade of Notch Signaling Ameliorates Murine Collagen-Induced Arthritis via Suppressing Th1 and Th17 Cell Responses. 2014; Pathology, 184(4):1085-1093.
Kailasapathy, K. Microencapsulation of Probiotic Bacteria:Technology and Potential Applications. Curr. Issues Intest. Microbiol. (2002) 3: 39-48.
Kang et al. (2010) "Dysbiosis of fecal microbiota in Crohn's disease patients as revealed by a custom phylogenetic microarray," Inflammatory Bowel Diseases. 16(12):2034-2042.
Kelly et al. 'Commensal anaerobic gut bacteria attenuate inflammation by regulating nuclear-cytoplasmic shuttling of PPAR-y and ReiA.' Nature Immunology. 2003, vol. 5, No. 1, pp. 104-112.
Kingsley M. A Personalized Approach to Managing 18D. Gastroenterology and Hepatology 12(5)308-315, May 2016.

(56) References Cited

OTHER PUBLICATIONS

Kinnebrew et al., Interleukin 23 production by intestinal CD1 03(+)CD11 b(+) dendritic cells in response to Interleukin 23 production by intestinal CD1 03(+ )CD11 b(+) dendritic cells in response to bacterial flagellin enhances mucosal innate immune defense, Immunity. 2012; 36(2): 276-287.
Koenders, M.I. et al., Interleukin-17 Acts Independently of TNF-a under Arthritic Conditions. (2006) J. Immunol. 176:6262-6269.
Lakhdari, et al. Identification of NF-Kb Modulation Capabilities within Human Intestinal Commensal Bacteria. J Biomed Biotechnol. 2011; 2011: 282356.
Lavallie et al. (1995) "Gene fusion expression systems in *Escherichia coli*," Current Opinion Biotechnology. 6 (5):501-506.
Leslie, et al., Trehalose and sucrose protect both membranes and proteins in intact bacteria during drying. (1995) Appl. Environ. Microbiol. 61, 3592-3597.
Letran et al. 'TLR5-deficient mice lack basal inflammatory and metabolic defects but exhibit impaired CD4 T cell responses to a ftagellated pathogen.' The Journal of Immunology. 2011, vol. 186, No. 9, pp. 5406-5412.
Lilley et al., Methods in Enzymology; DNA Structure Part A: Synthesis and Physical Analysis of DNA. 1992; vol. 2011. pp. v-vii.
Louis et al. 'Diversity, metabolism and microbial ecology of butyrate-producing bacteria from the human large Intestine.' FEMS Microbiology Letters. 2009, vol. 294, No. 1, pp. 1-8.
Louis et al. 'Diversity of human colonic butyrate-producing bacteria revealed by analysis of the butyryl-GoA: acetate GoA-transferase gene.' Environmental Microbiology. 2010, vol. 12, No. 2, pp. 304-314.
Louis et al. 'Organization of butyrate synthetic genes in human colonic bacteria: phylogenetic conservation and horizontal gene transfer.' FEMS Microbiology Letters. 2007, vol. 269, No. 2, pp. 240-247.
Machiels, et al., Predominant dysbiosis in patients with ulcerative colitis is different from Crohn's disease patients, Inflammatory Bowel Diseases, Microbiology 2012. 8th Congress of ECCO. (This Abstract Is in 7th Congress 2012).
Machiels, K. A decrease of the butyrate-producing species *Roseburia hominis* and Faecalibacterium prausnitzii defines dysbiosis in patients with ulcerative colitis.Gut. Aug. 2014;63(8):1275-83. doi: 10.1136/gutjnl-2013-304833. Epub Sep. 10, 2013.
MacPherson, AJ et al., IgA responses in the intestinal mucosa against pathogenic and non-pathogenic microorganisms. Oct. 2001. 3(12). 1021-1035.
MacPherson, AJ., et al., The functions of mucosal T cells in containing the indigenous commensal flora of the intestine.Cell Mol Life Sci. Dec. 2002;59(12):2088-96.
MacPherson et al. 'IgA adaptation to the presence of commensal bacteria in the intestine.' Gut-Associated Lymphoid Tissues. Springer Berlin Heidelberg, 2006. 117-136.
Mahowald et al. 'Characterizing a model human gut microbiota composed of members of its two dominant bacterial phyla.' Proceedings of the National Academy of Sciences. 2009, vol. 106, No. 14, pp. 5859-5864.
Mallya et al. 'Characterization of the five novel Ly-6 superfamily members encoded in the MHC, and detection of cells expressing their potential ligands.' Protein Science. 2006, vol. 15, No. 10, pp. 2244-2256.
Martin et al., Cloning, Nucleotide Sequence, and Taxonomic Implications of the Flagellin Gene of Roseburia cecicola, Journal of Bacteriology. Jun. 1988; 170(6):2612-2617.
Masco, L., et al., Identification of Bifidobacterium Species Using rep-PCR Fingerprinting. Systematic and Applied Microbiology 26(4):557-63 | Dec. 2003.
Mazmanian et al. 'An immunomodulatory molecule of symbiotic bacteria directs maturation of the host immune system.' Cell. 2005, vol. 122, No. 1, pp. 107-118.
McIntosh et al. 'Mechanism of conjugated linoleic acid and vaccenic acid formation in human faecal suspensions and pure cultures of intestinal bacteria.' Microbiology. 2009, vol. 155, No. 1, pp. 285-294.
McLaughlin., "McLaughlin et al. Fatty acid chain length determines cholecystokinin secretion and effect on human gastric motility. Gastroenterology. 1999, vol. 116, No. 1, pp. 46-53".
Meyer et al. (1992) "The use of cassava mosaic virus as a vector system for plants," Gene. 110:213-217.
Mikayama, et al., Molecular cloning and functional expression of a cDNA encoding glycosylation-inhibiting factor. Proc.Nati.Acad. Sci. USA, Nov. 1993; vol. 90: 10056-10060.
Mitropoulou, G. et al. Immobilization Technologies in Probiotic Food Production. (2013) Journal Nutr Metab. (2013) 716861.
Miyamoto-Shinohara et al. Survival of freeze-dried bacteria. J Gen Appl Microbiol 54(1):9-24 (2008).
Monteleone et al., IL-10-dependent partial refractoriness to Toll-like receptor stimulation modulates gut mucosal dendritic cell function, European Journal of Immunology. 2008; 38(6):1533-1547.
Monteleone, I. et al., Th17-related cytokines: new players in the control of chronic intestinal inflammation. (2011) BMC Medicine. 2011,9:122.
Neish et al., TLRS in the Gut. II. Flagellin-induced inflammation and antiapoptosis, American Journal of Physiology-Gastrointestinal and Liver Physiology. 2007;292:G462-466.
Neville, B.A., Functional genomics of motile commensal intestinal bacteria. PhD Thesis. University College Cork. 2013. 281 Pages.
Neville, et al., Characterization of pro-inflammatory flagellin proteins produced by Lactobacillus ruminis and related motile Lactobacilli. PloS one. Jul. 2012;7(7):e40592.
Neyrinck et al. 'Dietary modulation of clostridial cluster XIVa gut bacteria (*Roseburia* spp.) by chitin-glucan fiber improves host metabolic alterations induced by high-fat diet in mice.' The Journal of Nutritional Biochemistry. 2012, vol. 23, No. 1, pp. 51-59.
Ng et al., Archaeal flagella, bacterial flagella and type IV pili: a comparison of genes and posttranslation modification, Journal of Molecular Microbiology and Biotechnology. 2006;11:167-191.
Notice of Allowance dated Feb. 3, 2016 for U.S. Appl. No. 14/349,907.
Notice of Allowance dated Mar. 6, 2017 for U.S. Appl. No. 14/249,710.
Notice of allowance dated Jun. 16, 2017 for U.S. Appl. No. 14/249,710.
Notice of allowance dated Sep. 6, 2017 for U.S. Appl. No. 14/249,710.
Notice of Allowance dated Nov. 17, 2016 for U.S. Appl. No. 14/249,710.
Notice of Allowance dated Nov. 24, 2017 for U.S. Appl. No. 15/070,605.
Nutsch et al., T cell tolerance and immunity to commensal bacteria. Current Opinion in Immunology. Aug. 2012; 24 (4):385-391.
Office Action dated Jan. 2, 2018 for U.S. Appl. No. 15/357,936.
Office Action dated Jan. 11, 2005 for U.S. Appl. No. 10/285,224.
Office Action dated Jan. 26, 2009 for U.S. Appl. No. 10/275,706.
Office Action dated Feb. 18, 2010 for U.S. Appl. No. 10/285,224.
Office Action dated Mar. 13, 2013 for U.S. Appl. No. 12/760,926.
Office Action dated Mar. 26, 2007 for U.S. Appl. No. 10/275,706.
Office Action dated Apr. 4, 2008 for U.S. Appl. No. 10/285,224.
Office Action dated May 2, 2007 for U.S. Appl. No. 10/285,224.
Office Action dated May 2, 2008 for U.S. Appl. No. 10/275,706.
Office Action dated May 25, 2016 for U.S. Appl. No. 14/249,710.
Office Action dated May 26, 2009 for U.S. Appl. No. 10/285,224.
Office Action dated May 26, 2017 for U.S. Appl. No. 15/357,850.
Office Action dated May 30, 2006 for U.S. Appl. No. 10/285,224.
Office Action dated Jun. 26, 2017 for U.S. Appl. No. 15/357,936.
Office Action dated Jul. 6, 2017 for U.S. Appl. No. 15/070,605.
Office action dated Jul. 8, 2015 for U.S. Appl. No. 14/349,907.
Office Action dated Jul. 31, 2017 for U.S. Appl. No. 15/359,988.
Office Action dated Aug. 10, 2017 for U.S. Appl. No. 15/357,850.
Office Action dated Aug. 21, 2013 for U.S. Appl. No. 12/760,926.
Office Action dated Sep. 4, 2015 for U.S. Appl. No. 14/249,710.
Office Action dated Sep. 17, 2010 for U.S. Appl. No. 10/285,224.
Office Action dated Oct. 12, 2005 for U.S. Appl. No. 10/285,224.

(56) References Cited

OTHER PUBLICATIONS

Office Action dated Oct. 28, 2009 for U.S. Appl. No. 10/275,706.
Office Action dated Oct. 30, 2008 for U.S. Appl. No. 10/285,224.
Office Action dated Nov. 2, 2017 for U.S. Appl. No. 15/700,007.
Office Action dated Nov. 6, 2006 for U.S. Appl. No. 10/285,224.
Office Action dated Nov. 23, 2015 for U.S. Appl. No. 14/232,475.
Office Action dated Nov. 24, 2017 for U.S. Appl. No. 15/359,972.
Office Action dated Nov. 24, 2017 for U.S. Appl. No. 15/679,857.
Office Action dated Dec. 6, 2017 for U.S. Appl. No. 15/592,178.
Office Action dated Dec. 13, 2012 for U.S. Appl. No. 12/760,926.
Office Action dated Dec. 19, 2005 for U.S. Appl. No. 10/275,706.
Olivera et al. 'Nutritional and physiological responses of young growing rats to diets containing raw cowpea seed meal, protein isolate (globulins), or starch.' Journal of agricultural and food chemistry. 2003, vol. 51, No. 1, pp. 319-325.
Overstreet et al. 'Dysbiosis Characterized by Reduced Abundance of Roseburia is Associated With Increased Severity of Colitis in IL-10−/− Mice'. Gastroenterology. 2011, vol. 140, No. 5, Suppl. 1, pp. S-696.
Peterson et al. 'Catecholamines increase conjugative gene transfer between enteric bacteria.' Microbial Pathogensis. 2011, vol. 51, No. 1, pp. 1-8.
Polak J.M. and McGee J.O., In Situ Hybridization: Principles and Practice, Oxford University Press. 1990; pp. vii-viii.
Potrykus (1991) "Gene Transfer to Plants: Assessment of Published Approaches and Results," Annu. Rev. Plant Physiol. Plant Mol. Bioi. 42:205-225.
Prakash, et al., Complete genome sequences of rat and mouse segmented filamentous bacteria, a potent inducer of th17 cell differentiation. Cell Host & Microbe. Sep. 2011;10(3):273-284.
Pryde et al. 'The microbiology of butyrate formation in the human colon.' FEMS Microbiology Letters. 2002. vol. 217,No. 2, pp. 133-139.
Punt et al. (2002) "Filamentous fungi as cell factories for heterologous protein production," Trends Biotechnol. 20 (5):200-206.
Qin et al. 'A human gut microbial gene catalogue established by metagenomic sequencing.' Nature. 2010, vol. 464, No. 7285, pp. 59-65.
Reiff,C. and Kelly,D.,Inflammatory bowel disease, gut bacteria and probiotic therapy. International journal of medical microbiology, 2010;300:25-33.
Rhee et al.,Toll-Like Receptor 5 Engagement Modulates Tumor Development and Growth in a Mouse Xenograft Model of Human Colon Cancer. Gastroenterology. Aug. 2008;135(2):518-528.
Roe, et al., DNA Isolation and Sequencing: Essential Techniques. John Wiley & Sons, New York, New York. 1996; pp. v-vii.
Round et al. 'The Toll-like receptor 2 pathway establishes colonization by a commensal of the human microbiota.' Science. 2011, vol. 332, No. 6032, pp. 974-977.
Rudinger J, "Characteristics of the amino acids as components of a peptide hormone sequence," Peptide Hormones, JA Parsons Edition, University Park Press, Jun. 1976, pp. 1-7.
Russell et al. 'High-protein, reduced-carbohydrate weight-loss diets promote metabolite profiles likely to be detrimental to colonic health.' The American Journal of Clinical Nutrition. 2011, vol. 93, No. 5, pp. 1062-1072.
Salminen et al. 'Probiotics: how should they be defined?.' Trends in Food Science & Technology. 1999, vol. 10, No. 3, pp. 107-110.
Salonen et al., Gastrointestinal microbia in irritable bowel syndrome: present state and perspectives. Microbiology. 2010; 156:3205-3215.
Sambrook, J.F. et al., Molecular Cloning: A Laboratory Manual, 3rd ed. Cold spring harbor laboratory press. 2001.
Scanlan PD., et al., Culture-independent analyses of temporal variation of the dominant fecal microbiota and targeted bacterial subgroups in Crohn's disease. J Clin Microbiol. Nov. 2006;44(11):3980-8. Epub Sep. 20, 2006.
Schieck, M. et al., Genetic variation in TH17 pathway genes, childhood asthma, and total serum IgE levels.(2014) J Allergy Clin Immunol. 133(3):888-91.
Schulke et al. (Aug. 26, 2011) "A fusion protein of ftagellin and ovalbumin suppresses the 25 TH2 response and prevents murine intestinal allergy," The Journal of Allergy and Clinical Immunology. 128(6):1340-1348.
Scott et al. 'Substrate-driven gene expression in Roseburia inulinivorans: importance of inducible enzymes in the utilization of inulin and starch.' Proceedings of the National Academy of Sciences. 2011, vol. 108, Supp. 1, pp. 672-4679.
Sczesnak, et al., The genome of th17 cell-inducing segmented filamentous bacteria reveals extensive auxotrophy and adaptations to the intestinal environment. Cell Host Microbe. Sep. 2011;10(3):260-272.
Shabgah, A.G. et al., Interleukin-17 in human inflammatory diseases. Postepy Dermatol Alergol. Aug. 2014; 31(4): 256-261.
Shevach et al., Current Protocols in Immunology. John Wiley & Sons. New York, New York. 1992. Table of Contents only, as accessed online at URL: http://www.4ulr.com/products/currentprotocols/immunology_toc.html. [Last Accessed Jun. 18, 2015].
Skountzou, et al., *Salmonella* flagellins are potent adjuvants for intranasally administered whole inactivated influenza vaccine. Vaccine. May 2010; 28(24):4103-4112.
Smith, et al. Comparison of Biosequences. Advances in Applied Mathematics. 1981;2: 482-489.
Sokol et al. 'Faecalibacterium prausnitzii is an anti-inftammatory commensal bacterium identified by gut microbiota analysis of Crohn disease patients.' Proceedings of the National Academy of Sciences. 2008, vol. 105, No. 43, pp. 6731-16736.
Sokol et al. 'Low counts of Faecalibacterium prausnitzii in colitis microbiota.' Inflammatory bowel diseases. 2009, vol. 15, No. 8, pp. 1183-1189.
U.S. Appl. No. 15/700,007 Office Action dated Jun. 1, 2018.
Spor, A. et al., Unravelling the effects of the environment and host genotype on the gut microbiome. Nat Rev Microbiol. Apr. 2011;9(4):279-90. doi: 10.1038/nrmicro2540.
Srutkova, D. et al., Efficiency of PCR-based methods in discriminating *Bifidobacterium longum* ssp. *longum* and *Bifidobacterium longum* ssp. *infantis* strains of human origin.J Microbiol Methods. Oct. 2011;87(1):10-6. doi: 10.1016/j.mimet.2011.06.014. Epub Jul. 2, 2011.
Stanton et al. (1983) "*Roseburia cecicola* gen. nov., sp. nov., a Motile, Obligately Anaerobic Bacterium from a Mouse Cecum," Int. J. Syst. Bacterial. 33:618-627.
Strobel, H.J. Basic laboratory culture methods for anaerobic bacteria. Methods Mol Biol. 2009;581:247-61. doi: 10.1007/978-1-60761-214-8_16.
Tamanai-Shacoori, et al., *Roseburia* spp.: a marker of health?. Future Microbiology Review 12(2), 157-170 (2017).
Tatusova, et al., Erratum to BLAST 2 Sequences, a new tool for comparing protein and nucleotide sequences [FEMS Microbiol. 174 (1999) 247-250], FEMS Microbial. Lett. 1999;177(1):187-188.
Tatusova et al. (1999) "BLAST 2 Sequences, a new tool for comparing protein and nucleotide sequences," FEMS Microbial. Lett. 174(2):247-250.
Tesmer, LA. et al., Th17 cells in human disease. Immunol Rev. 2008;223:87-113.
Tilg, et al., Roseburia hominis: a novel guilty player in ulcerative colitis pathogenesis? Gut, Oct. 14, 2013;63(8)1204-1205.
Travis, et al. Complete genome sequence of the human gut symbiont Roseburia hominis. Genome announcements. 2015; 3(6):e01286-15.
Tremaroli, et al., A role for the gut microbiota in energy harvesting? Gut. Dec. 2010; 59(12):1589-1590.
Trueman (1995) "Heterologous Expression in Yeast," Methods Molecular Biology. 49:341-354.
Turnbaugh, et al., An obesity-associated gut microbiome with increased capacity for energy harvest. Nature. Dec. 2006;444(7122):1027-1031.
Turnbaugh et al., Diet-induced obesity is linked to marked but reversible alterations in the mouse distal gut microbiome. Cell Host & Microbe. Apr. 2008;3(4):213-223.

(56) References Cited

OTHER PUBLICATIONS

Turner (1994) "Vectors for genetic manipulation," In; Martinelli, S.D.; Kinghorn J. R.: Eds. Aspergillus: 50 years on. Progress in industrial microbiology. vol. 29. Elsevier. Amserdam, The Netherlands, pp. 641-666.
Ukena, et al., Probiotic *Escherichia coli* Nissle 1917 inhibits leaky gut by enhancing mucosal integrity, PloS one. Dec. 2007;2(12):e1308.
Untergasser, et al., Primer3Plus, an enhanced web interface to Primer3, Nucleic Acids Res. 2007;35(Web Server issue):W71-W74.
U.S. Appl. No. 15/359,144 Office Action dated Apr. 10, 2018.
U.S. Appl. No. 15/359,972 Office Action dated Apr. 4, 2018.
U.S. Appl. No. 15/631,952 Office Action dated Feb. 16, 2018.
U.S. Appl. No. 15/673,270 Office Action dated Apr. 10, 2018.
U.S. Appl. No. 15/679,857 Office Action dated Feb. 14, 2018.
Van Immerseel et al. 'Butyric acid-producing anaerobic bacteria as a novel probiotic treatment approach for inflammatory bowel disease.' Journal of medical microbiology. 2010, vol. 59, No. 2, pp. 141-143.
Vijay-Kumar, et al., Deletion of TLR5 results in 10 spontaneous colitis in mice. The Journal of Clinical Investigation. Dec. 2007;117(12):3909-3921.
Vijay-Kumar et al., Flagellin Treatment Protects against Chemicals, Bacteria, Viruses, and Radiation. The Journal of Immunology. 2008;180(12):8280-8285.
Walker et al. 'Dominant and diet-responsive groups of bacteria within the human colonic microbiota.' The ISME Journal. 2010, vol. 5, No. 2, pp. 220-230.
Watson, et al., Signal transduction in Campylobacter jejuni-induced cytokine production. Cellular Microbiology. 2005;7(5):655-665.
Weigel, et al., Comparative analysis of murine marrow-derived dendritic cells generated by Flt3L or GMCSF/IL-4 and matured with immune stimulatory agents on the in vivo induction of antileukemia responses. Blood. Dec. 2002;100(12):4169-4176.
Werth, et al., The transcription factor grainyhead-like 2 regulates the molecular composition of the epithelial apical junctional complex. Development. 2010;37(22):3835-3845.
Wilson, et al., The TLR5 ligand flagellin promotes asthma by priming allergic responses to indoor allergens. Nature Medicine. Nov. 2012;18(11):1705-1710.
Xu, et al., Differential development of murine dendritic cells by GM-CSF versus Flt3 ligand has implications for inflammation and trafficking. J. Immunology. 2007;179(11):7577-7584.
Yang, J. et al., Targeting Th17 cells in autoimmune diseases. Trends Pharmacol Sci. Oct. 2014;35(10):493-500. doi: 10.1016/j.tips.2014.07.006. Epub Aug. 14, 2014.
Ye, X. et al., The Role of IL-23/Th17 Pathway in Patients with Primary Immune Thrombocytopenia. (2015) PLoS One. 10(1):e0117704.
Yin, X. et al., Combined effect of five single nucleotide polymorphisms related to IL23/Th17 pathway in the risk of psoriasis. Immunogenetics. Mar. 2014;66(3):215-8. doi: 10.1007/s00251-013-0756-z. Epub Jan. 14, 2014.
Yoon, et al., Structural basis of TLR5-flagellin recognition and signaling. Science. Feb. 2012; 335(6070):859-864.
Abel and Zukin, "Epigenetic targets of HDAC inhibition in neurodegenerative and psychiatric disorders", 2008, Current Opinion Pharmacology, 2008. 8(1): 57-64. Feb. 2008.
Alenghat, Theresa et al., "Histone deacetylase 3 coordinates commensal-bacteria-dependent intestinal homeostasis",2013, Nature, 504: 153-157. Published: Nov. 3, 2013.
Angiolilli, Chiara et al., "Hisone deacetylase 3 regulates the inflammatory gene expression programme of rheumatoid arthritis fibroblast-like synoviocytes", Ann Rheum Dis, 2017, 76: 277-285. Epub Jul. 26, 2015.
Auriel, E. et al., "Chapter 38—Nonsteroidal anti-inflammatory drugs exposure and the central nerous system", 2014, Handbook of Clinical Neurology 119, 577-584.
Baraczka, Krisztina et al,"Changes in dopamine and 3,4-dihydroxyphenylacetic acid (DOPAC) levels in human cerebrospinal fluid after L-dopa and deprenyl administration", J Neural Transmission, 1983, 58(3-4):299-304. Dec. 31, 1982.
Bourassa, Megan W et al. "Butyrate, neuroepigenetics and the gut microbiome: Can a high fiber diet improve brain health?." Neuroscience letters vol. 625 (2016): 56-63. doi:10.1016/j.neulet.2016.02.009. Jun. 20, 2016.
Bravo, Javier A. et al., "Ingestion of Lactobacillus strain regulates emotional behavior and central GABA receptor expression in a mouse via the vagus nerve", PNAS Sep. 20, 2011 108 (38) 16050-16055; https://doi.org/10.1073/pnas.1102999108.
Budd and Nicholls, "Mitochondria in the life and death of neurons", 1998, Essays in Biochemistry, 33:43-52.
Carlson, Greg C. "Glutamate receptor dysfunction and drug targets across models of autism spectrum disorders." Pharmacology, biochemistry, and behavior vol. 100,4 (2012): 850-4. doi:10.1016/j.pbb.2011.02.003. Epub Feb. 16, 2011.
Choji Kaneuchi et al., "Clostridium coccoides, a New Species from the Feces of Mice", International Journal of Systematic Bacteriology, vol. 26, No. 4, Oct. 1976, p. 482-486.
Constantinescu, Cris S et al. "Experimental autoimmune encephalomyelitis (EAE) as a model for multiple sclerosis (MS)." British journal of pharmacology vol. 164,4 (2011): 1079-106. doi:10.1111/j. 1476-5381.2011,01302.x. Oct. 2011.
Coughenour LL et al.," A new device for the rapid measurement of impaired motor function in mice", Pharmacol Biochem Behav. Mar. 1977;6(3):351-3.
Crawley, Jacqueline N. "Translational animal models of autism and neurodevelopmental disorders." Dialogues in clinical neuroscience vol. 14,3 (2012): 293-305. Sep. 2012.
Cryan JF and Mombereau C.,"In search of a depressed mouse: utility of models for studying depression-related behavior in genetically modified mice", Mol Psychiatry. Apr. 2004;9(4):326-57.
Cryan, John F, and Timothy G Dinan. "More than a gut feeling: the microbiota regulates neurodevelopment and behavior." Neuropsychopharmacology : official publication of the American College of Neuropsychopharmacology vol. 40,1 (2015): 241-2. doi:10.1038/npp.2014.224. Jan. 2015.
Daniel Garrido et al., "Utilization of galactooligosaccharides by *Bifidobacterium longum* subsp. *infantis* isolates", Food Microbiology, 33 (2013) 262-270. Epub Oct. 22, 2012.
Daniele, Stefano G et al. "Activation of MyD88-dependent TLR1/2 signaling by misfolded α-synuclein, a protein linked to neurodegenerative disorders." Science signaling vol. 8,376 ra45. May 12, 2015, doi:10.1126/scisignal.2005965.
Day, John G., McLellan, Mark R., "Cryopreservation and Freeze-Drying Protocols" Methods in Molecular Biology, 2007.
Desbonnet L et al., "Gut microbiota depletion from early adolescence in mice: Implications for brain and behaviour", Brain Behav Immun. Aug. 2015;48:165-73. doi: 10.1016/j.bbi.2015.04.004. Epub Apr. 10, 2015.
Dheeraj Mohania et al., "Modulation of expression of Programmed Death-1 by administration of probiotic Dahi in DMH-induced colorectal carcinogenesis in rats", ACTA BIOMED 2013; 84: 102-109. Sep. 1, 2013.
Dong-Hyun Kim and Young-Ho Jin, "Intestinal Bacterial B-Glucuronidase Activity of Patients with Colon Cancer", Arch Pharm Res vol. 24, No. 6, 564-567, 2001. Published: Dec. 2001.
Ebadi M. et al. "Ubiquinone (Coenzyme Q10) and Mitochondria in Oxidative Stress of Parkinson's Disease", 2001, Biological Signals and Receplors 10(3-4):224-253.
Eldrup, E. et al., "CSF and plasma concentrations of free norepinephrine, dopamine, 3,4-dihydroxyphenylacetic acid (DOPAC), 3,4-dihydroxyphenylalanine (DOPA), and epinephrine in Parkinson's disease", Acta Neurol Scand ,1995, 92(2):116-21. Aug. 1995.
Federico E. Rey et al., "Dissecting the in Vivo Metabolic Potential of Two Human Gut Acetogens", The Journal of Biological Chemistry, vol. 285, No. 29, p. 22082-22090, Jul. 16, 2010. Epub May 5, 2010.
Felice C. et al. "Review article: selective histone deacetylase isoforms as potential therapeutic targets in inflammatory bowel diseases", 2015, Ailmentary Pharmacology and Therapeutics, 41: 26-38. Epub Nov. 4, 2014.

(56) References Cited

OTHER PUBLICATIONS

Ferro Austin et al., "Short-term succinic acid treatment mitigates cerebellar mitochondrial OXPHOS dysfunction, neurodegeneration and ataxia in a Purkinje-specific spinocerebellar ataxia type 1 (SCA1) mouse model", 2017, PLoS One 2017, 12(12):e0188425. Dec. 6, 2017.

Fischer A et al., "Recovery of learning and memory is associated with chromatin remodelling", Nature. May 10, 2007;447(7141):178-82. Epub Apr. 29, 2007.

Foguem & Manckoundia, "Lewy Body Disease: Clinical and Pathological "Overlap Syndrome" Between Synucleinopathies (Parkinson Disease) and Tauopathies (Alzheimer Disease)", 2018, Current Neurology and Neuroscience Reports, 18:24. Apr. 8, 2018.

Gagnon, Melanie et al "Comparison of the Caco-2, HT-29 and the mucus-secreting HT29-MTX intestinal cell models to investigate Salmonella adhesion and invasion", 2013, Journal of Microbiological Methods. 94: 274-279. Epub Jul. 5, 2013.

Galpern & Lang, "Interface between tauopathies and synucleinopathies: A tale of two proteins"2006, Neurological Progress 59, 3, 449-458. Mar. 2006.

GenBank Accession No. AJ270478.2 of Oct. 3, 2002 (https://www.ncbi.nlm.nih.gov/nuccore/AJ270478).

Glauben, Rainer et al., "Histone Hyperacetylation Is Associated with Amelioration of Experimental Colitis in Mice", Journal of Immunology, 2006, 176: 5015-5022. Apr. 15, 2006.

Gonneaud Alexis, et al., "The histone deacetylase Hdac1 regulates inflammatory signalling in intestinal epithelial cells", 2014, Journal of Inflammation, 11: 43. doi: 10.1186/s12950-014-0043-2. Dec. 20, 2014.

Gray SG. and Dangond F. "Rationale for the use of histone deacetylase inhibitors as a dual therapeutic modality in multiple sclerosis.", Epigenetics. Apr.-Jun. 2006;1(2):67-75. Epub Mar. 5, 2006.

Hai-long Zhang et al., "Study on the Correlation of the Imbalance of TH17 Cells, Th1 Cell, Regulatory T Cells with ankylosing spondylitis Disease Activity Score", Medical Recapitulate, Dec. 2014, vol. 20, No. 24, pp. 4545-4555.

Haines, Isabel et al., "Soluble Fibre Meal Challenge Reduces Airway Inflammation and Expression of GPR43 and GPR41 in Asthma", Nutrients, 2017, 9, 57, pp. 1-11. Published online Jan. 10, 2017.

Hasegawa, Satoru et al. "Intestinal Dysbiosis and Lowered Serum Lipopolysaccharide-Binding Protein in Parkinson's Disease." PloS one vol. 10,11 e0142164. Nov. 5, 2015, doi: 10.1371/journal.pone.0142164.

Hely Mariese A. et al., "Sydney Multicenter Study of Parkinson's Disease: Non-L-Dopa-Responsive Problems Dominate at 15 Years", 2005, Movement Disorders, 20(2): 190-9. Feb. 2005.

Hsiao, Elaine Y et al. "Microbiota modulate behavioral and physiological abnormalities associated with neurodevelopmental disorders." Cell vol. 155,7 (2013): 1451-63. doi: 10.1016/j.cell.2013.11.024. Epub Dec. 5, 2013.

Humira 20 mg/ 0.2 ml Solution for Injection in Pre-Filled Syringe—Summary of Product Characteristics, https://www.medicines.org.uk/emc/product/9080/smpc/print, accessed on Oct. 25, 2019, 30 pages.

Huot Philippe, "The pons and human affective processing—Implications for Parkinson's disease", 2015, EBioMedicine 2, 1592-1593. Nov. 2, 2015.

Huycke, M M et al. "Multiple-drug resistant enterococci: the nature of the problem and an agenda for the future." Emerging infectious diseases vol. 4,2 (1998): 239-49. doi: 10.3201/eid0402.980211. Apr.-Jun. 1998.

Hyland and Cox, "The regulation of veratridine-stimulated electrogenic ion transport in mouse colon by neuropeptide Y (NPY), Y1 and Y2 receptors", 2005, British Journal of Pharmacology,146(5), 712-722. Nov. 2005.

International Preliminary Report on Patentability dated Sep. 17, 2019 for International Application Serial No. PCT/EP2018/065809, (13 pages).

International Search Report dated Aug. 24, 2018 for International Application Serial No. PCT/EP2018/065809, (6 pages).

Jacobs, S. A., Huang, F., Tsien, J. Z. and Wei, W. (2016). Social Recognition Memory Test in Rodents. Bio-protocol 6(9): e1804. DOI:10.21769/BioProtoc.1804. May 5, 2016.

Jagveer Singh et al., "Bifidobacterium longum, a lactic acid-producing intestinal bacterium inhibits colon cancer and modulates the intermediate biomarkers of colon carcinogenesis", Carcinogenesis vol. 18 No. 4 pp. 833-841, 1997. Apr. 1997.

Johnsen, Lea G et al., "Gas chromatography—mass spectrometry data processing made easy", Journal of Chromatography A. 2017, 1503: 57-64. Epub Apr. 27, 2017.

Kadi Linda et al. "Differential effects of chemokines on oligodendrocyte precursor proliferation and myelin formation in vitro", Journal of Neuroimmunology, 2006,174:133-146. Epub Mar. 30, 2006.

Kang and Kim, 2015, "Suprression of NMDA receptor function in mice prenatally exposed to valproic acid improves social deficits and repetitive behaviors", Fronteirs in Molecular neuroscience, 2015, 8:(17), 1-9. May 27, 2015.

Kantak PA et al., "Obsessive-compulsive-like behaviors in house mice are attenuated by a probiotic (*Lactobacillus rhamnosus* GG)", Behav Pharmacol. Feb. 2014;25(1):71-9. doi: 10.1097/FBP.0000000000000013.

Kari Shoaf et al., "Prebiotic Galactooligosaccharides Reduce Adherence of Enteropathogenic *Escherichia coli* to Tissue Culture Cells", Infection and Immunity, Dec. 2006, vol. 74. No. 12, p. 6920-6928. Epub Sep. 18, 2006.

Kehr J., "Monitoring chemistry of brain microenvironment: biosensors, microdialysis and related techniques", 1999, Chapter 41. In: Modern techniques in neuroscience research. (Eds. U. Windhorst and H. Johansson) Springer-Verlag GmbH., Heidelberg, Germany. 1149-1198.

Kitahara, Maki et al., *Bateroides plebeius* sp. nov. and *Bacteroides coprocola* sp. nov., isolated from human faeces, International Jounal of systematic and Evolutionary Microbiology, (2005), vol. 55, 2143-2147, DOI 10.1099/ijs.063788.0. First Published: Sep. 1, 2005.

Kondziella, W, "A New Method for the Measurement of Muscle Relaxation in White Mice" Arch Int Pharmacodyn Ther. Dec. 1, 1964;152:277-84.

Laetitia Rodes et al., "Microencapsulated *Bifidobacterium longum* subsp. *infantis* ATCC 15697 Favorably Modulates Gut Microbiota and Reduces Circulating Endotoxins in F344 Rats", BioMed Research International, vol. 2014, Article ID 602832, 11 pages. Epub May 22, 2014.

Lapadula, G. et al., "Adalimumab in the Treatment of Immune-Mediated Diseases", International Journal of Immunopathology and Pharmacology, 2014, vol. 27, No. 1(s), 33-48. Jan-Mar. 2014.

Laureen Crouzet et al., "The altered gut microbiota of IBS patients plays a key role in visceral hypersensitivity: specific role of sulphate-reducing bacteria", INRA Symposium, 2012.

Lee Do Yeon et al., "Kynurenic acid attenuates MPP—induced dopaminergic neuronal cell death via a Bax-mediated mitochondrial pathway",2008, European Journal of Cell Biology 87:389-397. Epub May 6, 2008.

Li Q et al.," The microbiota-gut-brain axis and its potential therapeutic role in autism spectrum disorder", Neuroscience. Jun. 2, 2016;324:131-9. doi: 10.1016/j.neuroscience.2016.03.013. Epub Mar. 8, 2016.

Ludolph, A C et al. "Tauopathies with parkinsonism: clinical spectrum, neuropathologic basis, biological markers, and treatment options." European journal of neurology vol. 16,3 (2009): 297-309. doi: 10.1111/j.1468-1331.2008.02513.x.

Mayer, Emeran A. et al.," Gut Microbes and the Brain: Paradigm Shift in Neuroscience", Journal of Neuroscience Nov. 12, 2014, 34 (46) 15490-15496; DOI: https://doi.org/10.1523/JNEUROSCI.3299-14.2014.

Michel and Prat, "One more role for the gut:microbiota and blood brain barrier", 2016, Ann Transl Med. 4(1): 15. Jan. 2016.

Mincheol Kim et al., "Towards a taxonomic coherence between average nucleotide identity and 16S rRNA gene sequence similarity

(56) References Cited

OTHER PUBLICATIONS for species demarcation of prokaryotes", International Journal of Systematic and Evolutionary Microbiology (2014), 64, 346-351. Feb. 1, 2014.
NCBI Reference Sequence: NR_026314.1, Blautia hydrogenotrophica strain S5a36 16S ribosomal RNA gene, partial sequence (Feb. 3, 2015), 3 pages.
NCBI Reference Sequence: NR_041278.1, Bacteroids coprocola strain M16165 ribosomal RNA gene, partial sequence. Aug. 8, 2011 National Center for Biotechnology Information, NIH.
Neary N. M. et al., "Appetite regulation: from the gut to the hypothalamus", Clinical endocrinology, 2004, vol. 60,. 2, pp. 153-160. Feb. 2004.
Non-Final Office Action dated Oct. 8, 2019 for U.S. Appl. No. 16/265,238.
Non-Final Office Action dated Oct. 9, 2019 for U.S. Appl. No. 15/969,543.
Odile Menard et al., "Gnotobiotic Mouse Immune Response Induced by *Bifidobacterium* sp. Strains Isolated from Infants", Applied and Environmental Microbiology, Feb. 2008, p. 660-666. Epub Dec. 14, 2007.
Package leaflet: Information for the patient; Humira 20 mg solution for injection in pre-filled sringe, adalimumab, last revised Mar. 2019, 18 pages.
Package leaflet: Information for the user, Remicade 100 mg powder for concentrate for solution for infusion, infliximab, last revised in Mar. 2019, 12 pages.
Package Leaflet: Information for the user, Simponi 100 mg solution for injection in pre-filled pen, golimumab, last revised in Apr. 2019,17 pages.
Padmanabhan, Roshan et al., "Non-contiguous finished genome sequence and description of *Megasphaera massiliensis* sp.nov.", Aug. 7, 2013, Standards in Genomic Sciences 8:525-538. eCollection Jul. 30, 2013.
Pakkenberg, B et al. "The absolute number of nerve cells in substantia nigra in normal subjects and in patients with Parkinson's disease estimated with an unbiased stereological method." Journal of neurology, neurosurgery, and psychiatry vol. 54,1 (1991): 30-3. doi:10.1136/jnnp.54.1.30. Jan. 1991.
Pal Rishi et al. , "Role of neuroinflammation and latent transcription factors in pathogenesis of Parkinson's disease", Neurological Research, 2016, 38(12), 1111-1122. Epub Nov. 3, 2016.
Parfenov A.I., "Pain syndrome in the practice of a gastroenterologist", "Breast Cancer" №0 from Jan. 25, 2008, 5 pages, https://www.rmj.ru/articles/bolevoy_sindrom/Bolevoy_sindrom_v_praktike_gastroenterologa/.
Pedro Berraondo et al., "Cytokines in clinical cancer immunotherapy", British Journal of Cancer, 2019, 120:6-15. Epub Nov. 9, 2018.
Ping Dong et al., "The role of intestinal bifidobacteria on immune system development in young rats", Early Human Development 86 (2010) 51-58. Epub Jan. 27, 2010.
Pirooznia, Sheila K, and Felice Elefant. "Targeting specific HATs for neurodegenerative disease treatment: translating basic biology to therapeutic possibilities." Frontiers in cellular neuroscience vol. 7 30. Mar. 28, 2013, doi:10.3389/fncel.2013.00030.
Prospective Studies Collaboration, "Cholesterol, diastolic blood pressure, and stroke: 13,000 strokes in 450,000 people in 45 prospective cohorts. Prospective studies collaboration", Lancet. Dec. 23-30, 1995;346(8991-8992):1647-53.
Przedborski, Serge et al., "The parkinsonian toxin MPTP: action and mechanism", Restorative Neurology and Neuroscience, 2000, 16(2):135-142.
Psaty BM et al., "Health outcomes associated with various antihypertensive therapies used as first-line agents: a network meta-analysis.",JAMA. May 21, 2003;289(19):2534-44.
Remicade 100mg powder for concentrate for solution for infusion—Summary of Product Characteristics, accessed Oct. 25, 2019, 28 pages.
Sakamoto, Mitsuo et al. "Reclassification of Bacteroides distasonis, Bacteroides goldsteinii and Bacteroides merdae as *Parabacteroides distasonis* gen. nov., comb, nov., *Parabacteroides goldsteinii* comb. nov. and *Parabacteroides merdae* comb. nov.",Journal of Systematic and Evolutionary Microbiology, 2006, vol. 56, No. 7, 1599-1605. Jul. 2006.
Savignac HM et al., "Bifidobacteria exert strain-specific effects on stress-related behavior and physiology in BALB/c mice.", Neurogastroenterol Motil. Nov. 2014;26(11):1615-27. doi: 10.1111/nmo.12427. Epub Sep. 24, 2014.
Scatton Bernard et al., "Reduction of Cortical Dopamine, Noradrenaline, Serotonin and Their Metabolites in Parkinson's Disease", (1983) Brain Research, 275(2): 321-8. Sep. 26, 1983.
Simponi 100 mg solution for injection in pre-filled pen—Summary of Product Characteristics, https://www.medicines.org.uk/emc/products/5133/smpc/print, accessed Oct. 25, 2019, 21 pages.
Smart, Kathleen F. et al., "Analytical platform for metabolome analysis of microbial cells using methyl chloroformate derivatization followed by gas chromatography-mass spectrometry", 2010, Nature Protocols. 10:1709-29. Epub Sep. 30, 2010.
Smith and Waterman, "Comparison of biosequences", Advances in Applied Mathematics, vol. 2, Issue 4, Dec. 1981, pp. 482-489.
Sudha B. Singh and Henry C. Lin, "Hydrogen Sulfide in Physiology and Diseases of the Digestive Tract", Microorganisms 2015, 3, 866-889; doi:10.3390/microorganisms3040866. Nov. 12, 2015.
Suzanne L. Topalian et al., "Survival, Durable Tumor Remission, and Long-Term Safety in Patients With Advanced Melanoma Receiving Nivolumab", Journal of Clinical Oncology, vol. 32, No. 10, Apr. 1, 2014, pp. 1-12. Epub Mar. 3, 2014.
Takashi Nakamura et al., "Evaluation of the Effects of Dietary Organic Germanium, Ge-132, and Raffinose Supplementation on Caecal Flora in Rats", Bioscience of Microbiota, Food and Health vol. 31 (2), 37-45, 2012. Epub Apr. 20, 2012.
Tang, Ying et al, "Inhibiting Histone Deacetylase 2 (HDAC2) Promotes Functional Recovery From Stroke" 2017, Journal of the American Heart Association, 6(10), 1-28. Oct. 5, 2017.
Tang,PhD, Jiaqi et al., "Prenatal Hypoxia Induced Dysfunction in Cerebral Arteries of Offspring Rats" 2017, Journal of the American Heart Association, 6(10), 1-12. Oct. 3, 2017.
U.S. Appl. No. 15/704,245 Non-Final Office Action dated Jul. 3, 2019.
U.S. Appl. No. 15/704,245 Non-Office Action dated Dec. 16, 2019.
U.S. Appl. No. 16/100,349 Final Office Action dated May 1, 2019.
U.S. Appl. No. 16/022,577 Non-Final Office Action dated Jul. 9, 2019.
Vorstman, Jacob A S et al. "Proline affects brain function in 22q11DS children with the low activity COMT 158 allele." Neuropsychopharmacology : official publication of the American College of Neuropsychopharmacology vol. 34,3 (2009): 739-46. doi:10.1038/npp.2008.132. Epub Sep. 3, 2008.
Waisman, Ari et al., "The role of IL-17 in CNS diseases", Acta Neuropathologica, Springer Verlag, Berlin, DE, 2015, vol. 129, No. 5, 625-637. Epub Feb. 26, 2015.
Wang, Huiying et al. "Effect of Probiotics on Central Nervous System Functions in Animals and Humans: A Systematic Review." Journal of neurogastroenterology and motility vol. 22,4 (2016): 589-605. doi:10.5056/jnm16018. Oct. 30, 2016.
Wang, Yan, and Lloyd H Kasper. "The role of microbiome in central nervous system disorders." Brain, behavior, and immunity vol. 38 (2014): 1-12. doi:10.1016/j.bbi.2013.12.015. May 2014.
Weon et al., "TiO2 Nanotubes with Open Channels as Deactivation-Resistant Photocatalyst for the Degradation of Volatile Organic Compounds", 2016, Environmental Science & Technology, 50, 2556-2563. Epub Feb. 18, 2016.
West and Johnstone, "New and emerging HDAC inhibitors for cancer treatment", The Journal of Clinical Investigation, 2014, 124, 30-39. Epub Jan. 2, 2014.
Yang, Changya et al., Non-invasive imaging of Toll-like receptor 5 expression using 131I-labeled mAb in the mice bearing H22 tumors, Oncology Letters, 7: 1919-1924, 2014, DOI: 10.3892/oo.2014.2025. Epub Apr. 2, 2014.
Yang, Fang, "The clinical significance of the imbalance of TH17 and Treg cells and their related cytokines in peripheral blood of Parkinson's disease patients", International Journal of clinical and experimental medicine, 2016, vol. 9, No. 9, 17946-17951.

(56) References Cited

OTHER PUBLICATIONS

Yoshinori Kohwi et al., "Antitumor Effect of Bifidobacterium Infant's in Mice", Gann, 69, 613-618; Oct. 1978.
Zadori, Denes et al., "Kynurenines in Parkinson's disease: therapeutic perspectives", 2012, Journal of Neural Transmission, 119, 2, 275-283. Epub Aug. 20, 2011.
Zheng, Zhen et al. "Peripheral brain-derived neurotrophic factor in autism spectrum disorder: a systematic review and meta-analysis", 2016, Scientific Reports, 6(31241) 1-8.
Zhou, Linghong, and Jane A Foster. "Psychobiotics and the gut-brain axis: in the pursuit of happiness." Neuropsychiatric disease and treatment vol. 11 715-23. Mar. 16, 2015, doi:10.2147/NDT. S61997.
Auriemma, Matteo et al., "Cytokines and T cells in atopic dermatitis", Eur. Cytokine Netw., vol. 24, No. 1, Mar. 2013, pp. 37-44.
Jan. 17, 2019 First Office Action for CN201680041407.6 (Translated).
Jan. 17, 2019 Notice of Allowance for U.S. Appl. No. 15/803,721.
Dec. 21, 2018 Notice of Allowance U.S. Appl. No. 15/700,700.
Jan. 30, 2019 Notice of Corrected Allowability for U.S. Appl. No. 15/803,721.
Jan. 30, 2019 Final Rejection for U.S. Appl. No. 15/842,635.
Feb. 1, 1019 Non-Final Office Action U.S. Appl. No. 16/040,356.
Mar. 4, 1019 Final Office Action for U.S. Appl. No. 15/704,245.
4d Pharma Plc: "Clinical Update—RNS—London Stock Exchange", Jul. 19, 2016.
4D Pharma:"4Dpharma PLC clinical update on blautix (TM), a novel treatment to irritable bowel syndrome," 4DPharma, Jan. 19, 2016, XP002769874, Retrieved from: https://www.directorstalkinterviews.com/4d-pharma-plc-clinical-update-on-blautix-a-novel-treatment-for-irritable-bowel-syndrome/412689588. [Retrieved on May 5, 2017].
Ahanchian, Hamic, A multi-strain synbiotic may reduce viral respiratory infections in asthmatic children: a randomized controlled trial; Sep. 2016, vol. 8, Issue 9, pp. 2833-2839, DOI: http://dxdoi.or/10.19082/2833.
Alp, G., and Aslim, B. (2010). Relationship between the resistance to bile salts and low pH with exopolysaccharide (EPS) production of *Bifidobacterium* spp. isolated from infants feces and breast milk. Anaerobe 16(2), 101-105. doi: 10.1016/j.anaerobe.2009.06.006. Epub Jul. 2, 2009.
Anonymous: "4D pharma's Blautix for Irritable Bowel Syndrome shows positive impact—pharmaceutical daily news", Dec. 13, 2016.
Appleyard, Caroline B. et al., Pretreatment with the probiotic VSL#3 delays transition from inflammation to dysplasia in rate model of colitis-associated cancer; Am J. Physiol. Gastrointest. Liver Physiol. 301:G1004-G1013, 2011, Sep. 8, 2011:DOI:10.1152. ajpg.00167.2011.
Arenberg, et al., Interferon-y-inducible Protein 10 (IP-10) Is an Angiostatic Factor That Inhibits Human Non-small Cell Lung Cancer (NSCLC) Tumorigenesis and Spontaneous Metastases. 1996. J. Exp.Med. 184:981-92. Sep. 1, 1996.
Atarashi et al., Th17 Cell Induction by Adhesion of Microbes to Intestinal Epithelial Cells. CELL, vol. 163, No. 2, Oct. 8, 2015. pp. 367-380.
Atarashi, et al., Treg induction by a rationally selected mixture of Clostridia strains from the human microbiota. Supplementary Information. Nature 500, 232-236 (Aug. 8, 2013) doi:10.1038/nature12331.
Atarashi, K. et al., Treg induction by a rationally selected mixture of Clostridia strains from the human microbiota. Nature. 2013; 500(7461):232-236. Epub Jul. 10, 2013.
ATCC Catalog, https://www.atcc.org/search_results.aspx?dsNav=Ntk:primarysearch%7cbacteroides+thetaiotaomicron%7c3%7c,Ny:true,ro:0,N:1000552&searchterms-bacteroides+thetaiotaomicron&redir=1, Accessed on May 2, 2018.
Awadel-Kariem, Mustafa et al., First report of Parabacteroides goldsteinii bacteraemia in a patient with complicated intra-abdominal infection, Anaerobe, vol. 16, Issue 3, Jun. 2010, pp. 223-225. Epub Feb. 6, 2010.

Aziz, R.K., Bartels, D., Best, A.A., DeJongh, M., Disz, T., Edwards, R.A., et al. (2008). The RAST Server: Rapid Annotations using Subsystems Technology. BMC Genomics 9, 75. doi: 10.1186/1471-2164-9-75. Published: Feb. 8, 2008.
Bagge, et al., Diversity of spore-forming bacteria in cattle manure, slaughterhouse waste and samples from biogas plants. Journal of applied microbiology. 2010;109: 1549-1565. Epub Jul. 13, 2010.
Banfield, J. & Murphy, K.R., Non-Th2, Late-onset, non-allergic asthma. Copd & Asthma for NPs, A peer-reviewed newsletter, Aug. 2016; 14: 8 Pages.
Barry, et al., Criteria for Disksusceptibility tests and quality control guidelines for the cefoperazone-sulbactam combination, Journal of clinical microbiology, Jan. 1988;26(1):13-17.
Beaucage, et al. Deoxynucleoside phosphoramidites—A new class of key intermediates for deoxypolynucleotide synthesis. Tetrahedron Letters, vol. 22, 1981, pp. 1859-1869.
Begley, M., Hill, C., and Gahan, C.G.M. (2006). Bile Salt Hydrolase Activity in Probiotics. Applied and Environmental Microbiology 72(3), 1729-1738. doi: 10.1128/AEM.72.3.1729-1738.2006.
Berger, B., Moine, D., Mansourian, R., and Arigoni, F. (2010). HspR Mutations Are Naturally Selected in Bifidobacterium longum When Successive Heat Shock Treatments Are Applied. Journal of Bacteriology 192(1), 256-263. doi: 10.1128/jb.01147-09.
Berger, S. Gideon guide to medically important bacteria. Gideon E-book Series. 2017 edition. 4 pages.
Bergonzelli, G.E., Granato, D., Pridmore, R.D., Marvin-Guy, L.F., Donnicola, D., and Corthesy-Theulaz, I.E. (2006). GroEL of Lactobacillus johnsonii La1 (NCC 533) is cell surface associated: potential role in interactions with the host and the gastric pathogen *Helicobacter pylori*. Infect Immun 74(1), 425-434. doi: 10.1128/IAI.74.1.425-434.2006.
Bernalier, A., et al., "Diversity of H2/C02-utilizing acetogenic Bacteria from Feces of Non-Methane-Producing Humans", Current Microbiology vol. 33 (Aug. 1996), pp. 94-99, Springer-Vertag New York Inc., USA.
Bernalier et al., "Acetogenesis from H02 and C0-2 by Methane and Non-Methane-Producing Human Colonic Bacterial Communities" Fems Microbiology Ecology, vol. 19. No. 3. 1996. pp. 193-202. XP000979130.
Bernalier et al. *Ruminococcus hydrogenotrophicus* sp. nov., a new H2/CO2-utilizing acetogenic bacterium isolated from human feces. 1996 Arch. Microbiol. 166 (3), 176-183. Sep. 1996.
Bertram, J. et al. Establishment of a cloned line of Lewis lung carcinoma cells adapted to cell culture. (1980) Cancer let. 11:63-73.
Blandino, G., Fazio, D., DiMarco, R. Probiotics: Overview of microbiological and immunological characteristics (2008). Expert Review of Anti-Infective Therapy, 6 (4), pp. 497-508.
Bond, John H., Jr., et al., "Factors Influencing Pulmonary Medicine Excretion in Man: An indirect method of studying the in situ metabolism of the methane-producing colonic bacteria"; Journal of Experimental Medicine, Oct. 29, 1970, pp. 572-388.
Born, P., et al., English Abstract "Carbohydrate substitutes: comparative study of intestinal absorption of fructose, sorbitol and xylitol", "Zuckeraustauschstoffe: Vergleichende Untersuchung zur intestinalen Resorption von Fructose, Sorbit und Xylit", Medizinische Klinik 89, Technischen Universitat Munchen (Munich) Nov. 15, 1994; 89 (11): 575-8 (Article in German), Urban & Vogel, Munich, Germany.
Born, P., et al., "Fecal bacterial activity in symptomatic carbohydrate malabsorption: Effect on the fecal short-chain fatty acid ratio", intervention during the week "Digestive Diseases Week" from May 16 to May 19, 1999, Orlando, Z. Gasteroenterol2000: 38:623-626, Georg Thieme Verlag Stuttgart, New York, USA.
Bottacini, et al., Comparative genomics of the Bifidobacterium brevetaxon. BMC Genomics, 2014; 15:170. DOI:10.1186/1471-1471-2164-15-170. Published: Mar. 1, 2014.
Bottacini, F., Morrissey, R., Esteban-Torres, M., James, K., van Breen, J., Dikareva, E., et al. (2018). Comparative genomics and genotype-phenotype associations in Bifidobacterium breve. Scientific Reports 8(1), 10633. doi: 10.1038/S41598-018-28919-4. Published: Jul. 13, 2018.
Bottacini, F., O'Connell Motherway, M., Kuczynski, J., O'Connell, K.J., Serafini, F., Duranti, S., et al. (2014). Comparative genomics

(56) References Cited

OTHER PUBLICATIONS of the Bifidobacterium breve taxon. BMC Genomics 15(1), 170. doi: 10.1186/1471-2164-15-170. Mar. 1, 2014.
Bressa, et al., Differences in gut microbiota profile between women with active lifestyle and sedentary women. Pios One, 2017; 12(2): 1-20. Feb. 10, 2017.
Bry et al. A model of host-microbial interactions in an open mammalian ecosystem. Science 273(5280):1380-1383 (1996). Sep. 6, 1996.
Buffie et al., Precision microbiome restoration of bile acid-mediated resistance to Clostridium difficile. Nature, 517(7533):205-208 (2015). Published online Oct. 22, 2014.
Busing, K. et al., Effects of oral Enterococcus faecium strain DSM 10663 NCIMB 10415 on diarrhoea patterns and performance of sucking piglets. Benef Microbes. Mar. 2015;6(1):41-4. doi: 10.3920/BM2014.0008.
"Campeau, J.L. et al., Intestinal Epithelial Cells Modulate Antigen-Presenting Cell Responses to Bacterial DNA. Infectionand Immunity. Aug. 2012; 80(8): 2632-2644."
Candela et al. 'Interaction of probiotic Lactobacillus and Bifidobacterium strains with human intestinal epithelial cells:Adhesion properties, competition against enteropathogens and modulation of IL-8 production'. International Journal of Food Microbiology. 2008, vol. 125, No. 3, pp. 286-292. Epub Apr. 30, 2008.
Candela, M., Bergmann, S., Vici, M., Vitali, B., Turroni, S., Eikmanns, B.J., et al. (2007). Binding of human plasminogen to Bifidobacterium. J Bacteriol 189(16), 5929-5936. doi: 10.1128/JB.00159-07. Epub Jun. 8, 2007.
Candela, M., Biagi, E., Centanni, M., Turroni, S., Vici, M., Musiani, F., et al. (2009). Bifidobacterial enolase, a cell surface receptor for human plasminogen involved in the interaction with the host. Microbiology 155(Pt 10), 3294-3303. doi: 10.1099/mic.0.028795-0. Epub Jul. 2, 2009.
Candela, M., Centanni M Fau—Fiori, J., Fiori J Fau—Biagi, E., Biagi E Fau—Turroni, S., Turroni S Fau—Orrico, C., Orrico C Fau—Bergmann, S., et al. (2010). DnaK from *Bifidobacterium animalis* subsp. *lactis* is a surface-exposed human plasminogen receptor upregulated in response to bile salts. Microbiology 156(6), 1609-1618.
Caruthers, et al. New chemical methods for synthesizing polynucleotides. Nucleic Acids Symp Ser. 1980;(7):215-23.
Casey et al. 'Isolation and characterization of anti-*Salmonella* lactic acid bacteria from the porcine gastrointestinal tract'. Letters in Applied Microbiology. 2004, vol. 39, No. 5, pp. 431-438.
Caspi, P.R. Experimental autoimmune uveoretinitis in the rat and mouse. Curr Protoc Immunol. May 2003;Chapter 15:Unit 15.6. doi: 10.1002/0471142735.im1506s53.
Cekanaviciute, et al., Gut bacteria from multiple sclerosis patients modulate human T cells and exacerbate symptoms in mouse models. PNAS. Received for review Jun. 30, 2017; 1-6. Oct. 3, 2017 114 (40) 10713-10718; first published Sep. 11, 2017.
Charriot, et al., Future treatment for ashtma, Eur Respir Rev 2016; 25: 77-92.
Chen, S. et al., Live combined bacillus subtilis and enterococcus faecium ameliorate murine experimental colitis by immunosuppression. International journal of inflammation. 2014(878054). 7 Pages. Published online Sep. 8, 2014.
Chi, W. et al., IL-23 promotes CD4+ T cells to produce IL-17 in Vogt-Koyanagi-Harada disease. J Allergy Clin Immunol. May 2007;119(5):1218-24. Epub Mar. 1, 2007.
Chi, W. et al. Upregulated IL-23 and IL-17 in Behet patients with active uveitis. Invest Ophthalmol Vis Sci. Jul. 2008;49(7):3058-64. doi: 10.1167/iovs.07-1390.
Chiu, et al., Monocolonization of germ-free mice with bacteroides fragilis protects against dectran sulfate sodium-induced acute colitis. Biomed Research International 2014. vol. 2014. Article ID 675786. 9 Pages. May 29, 2014.
Christiaen, S.E., O'Connell Motherway, M., Bottacini, F., Lanigan, N., Casey, P.G., Huys, G., et al. (2014). Autoinducer-2 plays a crucial role in gut colonization and probiotic functionality of Bifidobacterium breve UCC2003. PLoS One 9(5), e98111. doi: 10.1371/journal.pone.0098111. Published: May 28, 2014.
Christmann, et al., Human seroreactivity to gut microbiota antigens. J Allergy Clin Immunol 136(5):1378-1386; available online May 23, 2015.
Cintas LM, Casaus MP, Herranz C, Nes IF, Hernandez PE. Review: bacteriocins of lactic acid bacteria (2001). Food Sci Technol 7(4):281-305.
Claesson, et al. Gut microbiota composition correlates with diet and health in the elderly. 2012. Nature, 488, 178-184. Published: Jul. 13, 2012.
Claims to be granted in European Application No. 15817513.3 amended Jun. 6, 2016.
Clarridge III, J.E. Impact of 16S rRNA gene sequence analysis for identification of bacteria on clinical microbiology and infectious diseases (2004). Clinical Microbiology Reviews, 17 (4), pp. 840-862.
Clinical Trials forThetanix, EU Clinical Trials Register, Date of commencement of clinical trial: Oct. 16, 2015. Available at: https://clinicaltrialsregister.eu/ctr-search/search?query=Thetanix.
CN Office Action dated Jan. 17, 2019, for CN 201680041407.6 (translation not yet available).
Colin, et al., GIC-1001, A Clinical Stage, Orally Administered Colonic Analgesic Drug Proposed as a Cost-Effective Alternative to I.V. Sedation Used in Colonoscopy. Canadian Digestive Diseases Week, 2014; 2 pages.
Collins, M.D., et al., *Enterococcus avium* nom. rev., comb, nov.; *E. casseliflavus* nom. rev., comb, nov.; *E. durans* nom. rev., comb, nov.; *E. gallinarum* comb. nov.; and *E. malodoratus* sp. nov. (1984) Int J Syst Evol Microbiol. 34: 220-223. First Published: Apr. 1, 1984.
Constantinescu et al. Experimental autoimmune encephalomyelitis (EAE) as a model for multiple sclerosis (MS). 2011. Br J Pharmacol. 164(4):1079-1106.
Co-pending U.S. Appl. No. 16/147,551, filed Sep. 28, 2018.
Co-pending U.S. Appl. No. 16/206,250, filed Nov. 30, 2018.
Co-pending U.S. Appl. No. 16/240,644, filed Jan. 4, 2019.
Co-pending U.S. Appl. No. 16/247,834, filed Jan. 15, 2019.
Co-pending U.S. Appl. No. 16/248,857, filed Jan. 16, 2019.
Co-pending U.S. Appl. No. 16/251,462, filed Jan. 18, 2019.
Co-pending U.S. Appl. No. 16/265,238, filed Feb. 1, 2019.
Cotter, P.O., Hill, C., Ross, R.P. Food microbiology: Bacteriocins: Developing imlate immunity for food (2005). Nature Reviews Microbiology, 3 (10), pp. 777-788.
Cronin, M., Knobel, M., O'Connell-Motherway, M., Fitzgerald, G.F., and van Sinderen, D. (2007). Molecular Dissection of a Bifidobacterial Replicon. Applied and Environmental Microbiology 73(24), 7858-7866.
Cummings, M., Breitling, R., and Takano, E. (2014). Steps towards the synthetic biology of polyketide biosynthesis. Fems Microbiology Letters 351(2), 116-125. doi: 10.1111/1574-6968.12365. Epub Jan. 7, 2014.
Dahya V. et al., Clostridium ramosum Osteomyelitis in an immunocompetent patient after traumatic injury, Infectious Diseases in Clinical Practice Mar. 12, 2015 Lippincott Williams and Wilkins USA, vol. 23, No. 2, Mar. 12, 2015, pp. 102-104, XP009193312, ISSN: 1056-9103 the whole document.
Darfeuille-Michaud et al. High prevalence of adherent-invasive *Escherichia coli* associated with ileal mucosa in Crohn's disease. 2004. Gastroenterology 127(2):412-21.
Darlington, G.J., Liver Cell Lines. (1987) Meth Enzymol. 151:19-38.
DATABASE UniProt [Online] Jun. 1, 2003 (Jun. 1, 2003), "subname:Full=possible pirin family protein {ECO:0000313|EMBL:AAO75294.1};", XP00275366,retrieved from EBI accession No. UNIPROT:Q8ABC3 Database accession No. Q8ABC3.
Davis et al. (1970) "Genetic and Microbiological Research Technqiues," Methods Enzymol. 17A:79-143.
De Ruyter, P.G., Kuipers, O.P., and de Vos, W.M. (1996). Controlled gene expression systems for Lactococcus lactis with the food-grade inducer nisin. Applied and Environmental Microbiology 62(10), 3662-3667.

(56) References Cited

OTHER PUBLICATIONS

Deangelis, M., et al., Selection of potential probiotic lactobacilli from pig feces to be used as additives in pelleted feeding (2006). Research in Microbiology, 157 (8), pp. 792-801. Epub Jun. 23, 2006.

Delgado, S., Ruiz, L., Hevia, A., Ruas-Madiedo, P., Margolles, A., and Sanchez, B. (2018). "Evidence of the In Vitro and In Vivo Immunological Relevance of Bifidobacteria," in the Bifidobacteria and Related Organisms.), 295-305.

Demarche, et al., Detailed analysis of sputum and systemic inflammation in asthma phenotypes: are paucigranulocytic asthmatics really non-inflammatory?, BMC Pulmonary Medicine, 2016; (16)46: 1-13. Published: Apr. 5, 2016.

Distrutti, et al., 5-Amino-2-hydroxybenzoic Acid 4-(5-Thioxo-5H-[1,2]dithiol-3yl)-phenyl Ester (ATB-429), a Hydrogen Sulfide-Releasing Derivative of Mesalamine, Exerts Antinociceptive Effects in a Model of Postinflammatory Hypersensitivity. The Journal of pharmacology and experimental therapeutics, 2006;319(1):447-458. Epub Jul. 19, 2006.

Distrutti, et al., Gut Microbiota role in irritable bowel syndrome: New therapeutic strategies. World Journal of Gastroenterology. Feb. 21, 2016; 22(7): p. 2219-2241, XP002769875.

Distrutti, et al., Hydrogen sulphide induces u opioid receptor-dependent analgesia in a rodent model of visceral pain. Molecular Pain, 2010; 6(36):1-16.

Divyashri et al. Probiotic attributes, antioxidant, anti-inflammatory and neuromodulatory effects of Enterococcus faecium CFR 3003: in vitro and in vivo evidence. (2015) J Med Microbiol, doi: 10.1099/jmm.0.000184. Dec. 2015;64(12):1527-1540. Epub Oct. 7, 2015.

DMSZ: Opening of Ampoules and Rehydration of Dried Cultures; (http://web.archive.org/web/20000 52411541 O/www.dsmz.de/open. htm); updated of website on Mar. 2000.

Dong, H., Rowland I Fau—Yaqoob, P., and Yaqoob, P. (2012). Comparative effects of six probiotic strains on immune function in vitro. Br J Nutr 108(3), 459-470. doi: 10.1017/S0007114511005824. Epub Nov. 7, 2011.

Drago, Lorenzo et al., Immunodulatory Effects of Lactobucillus salivarius LS01 and Bifidobacterium breve, Alone and in Combination on Peripheral Blood Mononuclear Cells of Allergic Asthmatics; Allergy Asthma Immunol. Res. Jul. 2015: 7(4):409-413. Published online Mar. 18, 2015.

Duncan, et al. *Roseburia intestinalis sp.* nov., a novel saccharolytic, butyrate-producing bacterium from human faeces. Int J Syst Evol Microbiol. Sep. 2002;52(Pt 5):1615-20.

Durand et al., "Reductive Acetogenesis in Animal and Human Gut." Physiological and Clinical Aspects of Short-Chain Fatty Acids, 1995. pp. 107-117, XP000979817 Cambridge University Press ISBN 0-521-44048-3.

Elhenawy et al., Preferential packing of acidic glycosidases and proteases into bacteroides Outer membrane vesicles. mBio 5:e00909-14, pp. 1-12, 2014.

Elmadfa, I., Klein, P., Meyer, AL. Immune-stimulating effects oflactic acid bacteria in vivo and in vitro (2010). Proceedings of the Nutrition Society, 69 (3), pp. 416-420. Epub Jun. 16, 2010.

Embl sequence AAO75294.1 (2003)—provided within the Office Action dated Feb. 16, 2018 in U.S. Appl. No. 15/631,952. 2 Pages.

Eren, A. Murat et al., "A single genus in the gut microbiome reflects host preference and specificity," The ISME Journal (2015) 9, 9-100 (2015).

ESR dated Dec. 17, 2018, Appl. 18189521.0.

Estelle Devillard et al., Metabolism of Linoleic Acid by Human Gut Bacteria: Different Routes for Biosynthesis of Conjugated Linoleic Acid, Journal of Bacteriology, Mar. 2007, vol. 189, No. 4, pp. 2566-2570. Epub Jan. 5, 2007.

European Communication dated Jun. 14, 2017 for EP Application No. 15817513.3.

Evelo Biosciences, Inc. Clinical Trials (Rank 1): A Study of EDP1503 in Patients With Colorectal Cancer, Breast Cancer, and Checkpoint Inhibitor Relapsed Tumors, https://clinicaltrials.gov/ct2/show/NCT03775850?spons=evelo&rank=1, 2018, accessed on Feb. 4, 2019.

Evelo Biosciences, Inc. Clinical Trials (Rank 2): A Study of EDP1815 in Healthy Participants and Participants With Mild to Moderate Psoriasis and Atopic Dermatitis, https://clinicaltrials.gov/ct2/show/NCT03733353?spons-evelo&rank-2, 2018, accessed on Feb. 4, 2019.

Evelo Biosciences, Inc. Clinical Trials (Rank 3): A Study of EDP1066 in Healthy Participants and Participants With Mild to Moderate Psoriasis and Atopic Dermatitis, https://clinicaltrials.gov/ct2/show/NCT03542994?spons-evelo&rank-3, 2018, accessed Feb. 4, 2019.

Evelo Biosciences, Inc. Clinical Trials (Rank 4): Pembrolizumab and EDP1503 in Advanced Melanoma, https://clinicaltrials.gov/ct2/show/NCT03595683?spons=evelo&rank=4, 2018, accessed Feb. 4, 2019.

Evelo Biosciences, Inc. Portfolio: https://evelobio.com/portfolio/, accessed Feb. 4, 2019.

Evelo Biosciences, Inc. website: https://evelobio.com/science/, accessed Feb. 4, 2019.

Faghih, Z. et a., IL-17 and IL-4 Producing CD8+ T Cells in Tumor Draining Lymph Nodes of Breast Cancer Patients: Positive Association with Tumor Progression. (2013). Iranian Journal of Immunology. 10(4):193-204.

Faith et al. Identifying gut microbe-host phenotype relationships using combinatorial communities in gnotobiotic mice. Sci Transl Med 6(220):220ra11 (2014).

Faith et al. The long-term stability of the human gut microbiota. 2013. Science, 341(6141): 1237439.

Falony, et al., Coculture Fermentations of Bifidobacterium species and bacteroides thetaiotaomicron Reveal a mechanistic insight into the prebiotic effect of inulin-type Fructans. Applied and environmental microbiology, Apr. 2009;75(8):2312-2319. Epub Feb. 27, 2009.

Fanning, S., Hall, L.J., Cronin, M., Zomer, A., MacSharry, J., Goulding, D., et al. (2012). Bifidobacterial surface-exopolysaccharide facilitates commensal-host interaction through immune modulation and pathogen protection. Proc Natl Acad Sci U S A 109(6), 2108-2113. doi: 10.1073/pnas.1115621109. Epub Jan. 23, 2012.

Farmer, et al., Gut pain & visceral hypersensitivity. British journal of pain, 2013;7(1):39-47.

Farooq, P.D. et al., Pseudomembranous colitis, Disease-A-Month 2015 Mosby Inc. USA, vol. 61, No. 5, May 1, 2015, pp. 181-206, XP009193313, ISSN: 0011-5029 p. 195.

Fenner, et al., *Bacteroides massiliensis* sp. nov., isolated from blood culture of a newborn. International Journal of systematic and evolutionary microbiology, 2005. 55: 1335-1337.

Ferrario, C., Milani, C., Mancabelli, L., Lugli, G.A., Duranti, S., Mangifesta, M., et al. (2016). Modulation of the eps-ome transcription of bifidobacteria through simulation of human intestinal environment. FEMS Microbiol Ecol 92(4), fiw056. doi: 10.1093/femsec/fiw056. . Epub Mar. 8, 2016.

Frick, et al., Identification of commensal bacterial strains that modulate Yersinia enterocolitica and Dextran sodium sulfate-induced inflammatory responses: implications for the development of probiotics. Infection and immunity, Jul. 2007;75(7):3490-3497. Epub May 7, 2007.

GB Exam and search report dated Aug. 30, 2016 for GB Application No. 1520638.6.

GB Search and Exam report dated Mar. 31, 2016 for GB application 1510469.8.

GB Search and Exam report dated Mar. 31, 2016 for GB application 1510470.6.

GB Search and Exam report dated Apr. 15, 2016 for GB application 1510467.2.

GB Search and Exam report dated Apr. 20, 2016 for GB application 1510466.4.

GB Search and Exam report dated Aug. 30, 2016 for GB application No. 1520631.1.

GB Search and Exam report dated Nov. 17, 2016 for GB application 1520502.4.

(56) References Cited

OTHER PUBLICATIONS

GB Search and Exam report dated Sep. 13, 2016 for GB application 1520497.7.
GB1612190.7 International Search Report dated Apr. 12, 2017.
GB1809729.5 Examination Report dated Oct. 15, 2018.
GenBank Accession No. NR_044054.1 (Feb. 3, 2015) Blautia wexlerae strain SSM 19850 16S ribsomal RNA gene, partial sequence.
GenBank Accession No. NR_117867.1 (Feb. 3, 2015) Blautia stercoris strain GAM6-1 16S ribsomal RNA gene, partial sequence.
Genbank NCBI Reference Sequence: NR-044054.1, Blautia wexlerae strain DSM 19850 16S ribosomal RNA gene, partial sequence, accessed Feb. 5, 2019.
Genbank NCBI Reference Sequence: NR_117867.1, Blautia stercoris strain GAMC6-1 16S ribosomal RNA gene, partial sequence, accessed Feb. 5, 2019.
Genbank NCBI Reference Sequence: NR_026314, Blautia hydrongentrophica strain S5a36 16S ribosomal RNA gene, partial sequence, accessed Feb. 5, 2019.
Ghadimi, D. et al., Epigenetic imprinting by commensal probiotics inhibits the IL-23/IL-17 axis in an in vitro model of the intestinal mucosal immune system. JLB. 2012;92(4):895-911. Epub Jun. 22, 2012.
Gonzalez-Rodriguez, I., Sanchez, B., Ruiz, L., Turroni, F., Ventura, M., Ruas-Madiedo, P., et al. (2012). Role of extracellular transaldolase from Bifidobacterium bifidum in mucin adhesion and aggregation. Appl Environ Microbiol 78(11), 3992-3998. doi: 10.1128/AEM. 08024-11. Epub Mar. 23, 2012.
Gopal, P.K., Sullivan, P.A., Smart, J.B. Utilization of galactooligosaccharides as selective substrates for growth by lactic acid bacteria including Bifidobacterium lactis DR10 and Lactobacillus rhamnosus DR20 (2001). International Dairy Journal, 11 (1-2), pp. 19-25. Dec. 31, 2000.
Gousia, P., et al., Antimicrobial resistance of major foodborne pathogens from major meat products (2011). Foodborne Pathogens and Disease, 8 (1), pp. 27-38. Epub Nov. 1, 2010.
Groeger, D., O'Mahony, L., Murphy, E.F., Bourke, J.F., Dinan, T.G., Kiely, B., et al. (2013). Bifidobacterium infantis 35624 modulates host inflammatory processes beyond the gut. Gut Microbes 4(4), 325-339. doi: 10.4161/gmic.25487. Epub Jun. 21, 2013.
GT Biologies obtains FDA orphan drug designation for paediatric crohn's drug, pharmaceutical-technology.com news, Oct. 8, 2013. Available at: http://www.pharmaceutical-technology.com/news/newsgt-biologics-obtains-fda-orphan-drug-designation-for-paediatric-crohns-drug?WT.mc_id=DN_News.
Guide for the care and use of laboratory animals: 8th edition. The national academic press; 2011.
Haabeth et al. A model for cancer-suppressive inflammation. (2012) OncoImmunology 1(1):1146-1152.
Hammerich, L. et al., Interleukins in chronic liver disease: lessons learned from experimental mouse models. (2014) Clin Exp Gastroenterol. Sep. 1, 2014;7:297-306.
Handbook of Experimental Immunology, vols. I IV (D.M. Weir and C.C. Blackwell, eds, 1986, Blackwell Scientific Publications).
Handbook of Pharmaceutical Excipients, 2nd Edition, (1994), Edited by A Wade and PJ Weller.
Hansen, et al., The role of mucosal immunity and host genetics in defining intestinal commensal bacteria. 2010. Curr. Opin. Gastroenterol., 26(6): 564-571.
Heberle, H., Meirelles, G.V., da Silva, F.R., Telles, G.P., and Minghim, R. (2015). InteractiVenn: a web-based tool for the analysis of sets through Venn diagrams. BMC Bioinformatics 16(1), 169. doi: 10.1186/s12859-015-0611-3.
Heuvelin, E., Lebreton, C., Grangette, C., Pot, B., Cerf-Bensussan, N., and Heyman, M. (2009). Mechanisms Involved in Alleviation of Intestinal Inflammation by Bifidobacterium Breve Soluble Factors. Plos One 4(4), e5184. doi: 10.1371/journal.pone.0005184. Epub Apr. 17, 2009.
Hidalgo-Cantabrana, C., Lopez, P., Gueimonde, M., de Los Reyes-Gavilan, C.G., Suarez, A., Margolles, A., et al. (2012). Immune Modulation Capability of Exopolysaccharides Synthesised by Lactic Acid Bacteria and Bifidobacteria. Probiotics Antimicrob Proteins 4(4), 227-237. doi: 10.1007/s12602-012-9110-2.
Hidalgo-Cantabrana, C., Sanchez, B., Alvarez-Martin, P., Lopez, P., Martinez-Alvarez, N., Delley, M., et al. (2015). A single mutation in the gene responsible for the mucoid phenotype of *Bifidobacterium animalis* subsp. *lactis* confers surface and functional characteristics. Appl Environ Microbiol 81(23), 7960-7968. doi: 10.1128/AEM. 02095-15. online Oct. 30, 2015.
Hidalgo-Cantabrana, C., Sanchez, B., Milani, C., Ventura, M., Margolles, A., and Ruas-Madiedo, P. (2014). Genomic overview and biological functions of exopolysaccharide biosynthesis in *Bifidobacterium* spp. Appl Environ Microbiol 80(1), 9-18. doi: 10.1128/AEM.02977-13. Epub Oct. 11, 2013.
Holdeman, et al., Eubacterium contortum (Prevot) comb. nov.: Emendation of description and designation of the type strain. International journal of systematic bacteriology. Oct. 1971;21(4): 304-306.
Horn, et al., Synthesis of Oligonucleotides on Cellulose. Part II: Design and Synthetic Strategy to the Synthesis of 22 Oligodeoxynucleotides Coding for Gastric Inhibitory Polypeptide (GIP). 1980. Nuc Acids Res Symp Ser 225-232.
Horwell, et al., The 'peptoid' approach to the design of non-peptide, small molecule agonists and antagonists of neuropeptides. 1995. Trends Biotechnol. 13(4):132-134.
Hougee, et al., Oral treatment with probiotics reduces allergic symptoms in ovalbumin-sensitized mice:a bacterial strain comparative study. Int Arch Allergy Immunol. 2010; 151:107-117. Epub Sep. 15, 2009.
Hughes, K.R., Harnisch, L.C., Alcon-Giner, C., Mitra, S., Wright, C.J., Ketskemety, J., et al. (2017). Bifidobacterium breve reduces apoptotic epithelial cell shedding in an exopolysaccharide and MyD88-dependent manner. Open Biol 7(1). doi: 10.1098/rsob. 160155.
Hytönen, J., Haataja, S., and Finne, J. (2003). *Streptococcus pyogenes* Glycoprotein-Binding Strepadhesin Activity Is Mediated by a Surface-Associated Carbohydrate-Degrading Enzyme, Pullulanase. Infection and Immunity 71(2), 784-793.
Hytonen, J., Haataja, S., and Finne, J. (2006). Use of flow cytometry for the adhesion analysis of *Streptococcus pyogenes* mutant strains to epithelial cells: investigation of the possible role of surface pullulanase and cysteine protease, and the transcriptional regulator Rgg. BMC Microbiol 6, 18. doi: 10.1186/1471-2180-6-18. Published online Feb. 24, 2006.
International Preliminary Report dated Mar. 1, 2017 for International Application No. PCT/GB2015/054113.
International Preliminary Report on Patentability for International Application No. PCT/GB2012/051686 dated Jan. 14, 2014.
International Search Report dated Jan. 27, 2017 for International Application No. PCT/GB2016/053622.
International Search Report dated Feb. 10, 2016 for International Application No. PCT/GB2015/054113.
International Search Report dated Feb. 17, 2017 for International Application No. PCT/GB2016/053676.
International Search Report dated Mar. 7, 2016 for International Application No. PCT/GB2015/054112.
International Search report dated Mar. 15, 2003 for International Application No. PCT/GB2002/05255.
International Search Report dated Aug. 26, 2016 for International application No. PCT/GB2016/051776.
International Search Report dated Sep. 6, 2016 for International application No. PCT/GB2016/051768.
International Search Report dated Sep. 6, 2016 for International application No. PCT/GB2016/051773.
International Search Report dated Sep. 6, 2016for International application No. PCT/GB2016/051770.
International Search Report dated Feb. 2, 2017 for International application No. PCT/GB2016/053620.
International Search Report dated Mar. 6, 2017 for International Application No. PCT/GB2016/053677.
International Search Report for International Application No. PCT/GB2012/051686 dated Jan. 31, 2013.
International search report with written opinion dated Feb. 26, 2018 for PCT/GB2017/053722.

(56) References Cited

OTHER PUBLICATIONS

International search report with written opinion dated Jun. 8, 2017 for GB Application No. 1616016.
International search report with written opinion dated Sep. 29, 2017 for GB Application No. 1621123.
International search report with written opinion dated Oct. 16, 2017 for PCT/GB2017/052076.
Inturri, R., Molinaro, A., Di Lorenzo, F., Blandino, G., Tomasello, B., Hidalgo-Cantabrana, C., et al. (2017). Chemical and biological properties of the novel exopolysaccharide produced by a probiotic strain of Bifidobacterium longum. Carbohydr Polym 174, 1172-1180. doi: 10.1016/j.carbpol.2017.07.039. Epub Jul. 19, 2017.
Ishikawa, et al., Effect of bifidobacteria to suppress Th17, Food Science and technology institute, 2008, 5 Pages.
Ispirli, H. et al., Characterization of functional properties of Enterococcus faecium strains isolated from human gut.Can. J. Microbiol. 61: 861-870 (2015) dx.doi.org/10.1139/cjm-2015-0446.
Israel, E. et al., Supplementary Appendix, Severe and difficult-to-treat asthma in adults. N. Engl J Med 2017;p. 377:965-76. DOI: 10.1056/NEJMra1608969.
Israel, et al., Severe and difficult-to-treat asthma in adults, The New England Journal of Medicine, Sep. 2017; 377(10):965-976.
Issue Notification dated Feb. 20, 2019 for Co-Pending U.S. Appl. No. 15/631,945.
Ivanov, D., Emonet, C., Foata, F., Affolter, M., Delley, M., Fisseha, M., et al. (2006). A serpin from the gut bacterium Bifidobacterium longum inhibits eukaryotic elastase-like serine proteases. J Biol Chem 281(25), 17246-17252. doi: 10.1074/jbc.M601678200. Epub Apr. 20, 2006.
Jackson MS, Bird AR, McOrist AL. Comparison of two selective media for the detection and enumeration of Lactobacilli in human faeces (2002). J Microbial Methods. 51 (3), pp. 313-321.
Jawad, S. et al., Elevated serum levels of interleukin-17A in uveitis patients. Ocul Immunol Inflamm. Dec. 2013;21 (6):434-9. doi: 10.3109/09273948.2013.815786. Epub Aug. 19, 2019.
Jenq, Robert R., Intestinal Bluatia is associated with reduced death from graft versus-host disease, Bio Blood Marro Transplant. Aug. 2015; 21(8): 1373-1383. doi:10.1016/j.bbmt.2015.04.016.
Jeon, S.G., Kayama, H., Ueda, Y., Takahashi, T., Asahara, T., Tsuji, H., et al. (2012). Probiotic Bifidobacterium breve induces IL-10-producing Tr1 cells in the colon. PLoS Pathog 8(5), e1002714. doi: 10.1371/journal.ppat.1002714. Epub May 31, 2012.
Joblin K N., "Ruminal Acetogens and Their Potential to Lower Remnant Methane Emissions." Australian Journal of Agricultural Research, vol. 50. No.8. 1999, pp. 1307-1313. XP001010439.
Kanauchi, et al., Eubacterium limosum ameliorates experimental colitis and metabolite of microbe attenuates colonic inflammatory action with increase of mucosal integrity introduction, China World J Gastroenterol February, Jan. 1, 2006. pp. 1071-1077.
Kanauchi, et al., Eubacterium limosum (probiotic) and its metabolites showed antiinflammatory effects and increased mucosal barrier function in colitis. Gastroenterology, 2005;128: p. A281, XP009193489.
Kang, S. et al., Dysbiosis of fecal microbiota in Crohn's disease patients as revealed by a custom phylogenetic microarray.Inflamm Bowel Dis. Dec. 2010;16(12):2034-42. doi: 10.1002/ibd.21319.
Karaffova, et al., Interaction of TGF-B4 and IL-17 with IgA secretion in the intestine of chickens fed with E. faecium AL41 and challenged with S. Enteritidis. Research in Veterinary science. 2015:75-79. Epub Apr. 17, 2015.
Karin, M. Nuclear factor-kappaB in cancer development and progression. Nature. May 25, 2006;441(7092):431-6.
Keller et al.. "DNA Probes", 1994. Stockton Press. New York. XP002158943 108660 pp. 594-596.
Kelly, et al., Commensal gut bacteria: mechanisms of immune modulation. Trends in immunology, 2005;26(6):326-333.
Kinoshita, H., Uchida, H., Kawai, Y., Kawasaki, T., Wakahara, N., Matsuo, H., et al. (2008). Cell surface Lactobacillus plantarum LA 318 glyceraldehyde-3-phosphate dehydrogenase (GAPDH) adheres to human colonic mucin. J Appl Microbiol 104(6), 1667-1674. doi: 10.1111/j.1365-2672.2007.03679.x. Epub Jan. 9, 2008.

Kirsty Minton: Mucosal immunology: The ins and outs of gut inflammation, The journal of immunology, 4(2), Feb. 1, 2004: pp. 81-81, XP055252701.
Kishimoto, M., Nomoto, R., Mizuno, M., and Osawa, R. (2017). An in vitro investigation of immunomodulatory properties of Lactobacillus plantarum and L. delbrueckii cells and their extracellular polysaccharides. Bioscience of Microbiota, Food and Health 36(3), 101-110. doi: 10.12938/bmfh.17-001. Epub Mar. 22, 2017.
Kitahara, M. et al., *Bacteroides plebeius* sp. nov. and *Bacteroides coprocola* sp. nov., isolated from human faeces, 2005; Int J Syst Ev Microbiol 55: 2143-47. First Published: Sep. 1, 2005.
Kogyo, S. Lactic Acid Bacteria, Intestinal Flora ad Health II; Physiological effects of heat-treated lactococcus "EF-2001" and application to food. Mar. 3, 20010, vol. 44, No. 6, pp. 35-39.
Koh, Gar Yee et al., Parabacteroides distasonis attenuate toll-like receptor 4 signalling and Akt activation and blocks colon tumor formulation in high-fat-diet-fed azoxymethane-treated mice, International Journal of Cancer, 2018, 143, 1797-1805. pp 1-30. Accepted Article, doi: 10.1002/ijc.31559. Apr. 26, 2018.
Korhonen, J.M., Sclivagnotis, Y., Von Wright, A Characterization of dominant cultivable lactobacilli and their antibiotic resistance profiles from faecal samples of weaning piglets (2007). Journal of Applied Microbiology, 103 (6), pp. 2496-2503.
Kumolosasi, E., Salim, E., Jantan, I., and Ahmad, W. (2014). Kinetics of Intracellular, Extracellular and Production of Pro-Inflammatory Cytokines in Lipopolysaccharide-Stimulated Human Peripheral Blood Mononuclear Cells. Tropical Journal of Pharmaceutical Research 13(4), 536-543. doi: 10.4314/tjpr.v13i4.8.
Kverka, M. et al., Oral administration of Parabacteroides distasonis antigens attenuates experimental murine colitis through modulation of immunity and microbiota composition. Clinical & Experimental Immunology. 2010; 163:250-259. Epub Nov. 19, 2010.
Lahteinen, T., et al., A Probiotic properties of Lactobacillus isolates originating from porcine intestine and feces (2010) Anaerobe, 16 (3), pp. 293-300. Epub Aug. 18, 2009.
Laukova, A. et al. Benefits of Combinative Application of Probiotic, Enterocin M-Producing Strain Enterococcus Faecium AL41 and Eleutherococcus Senticosus in Rabbits. Folia Microbiol (Praha) 61 (2), 169-177. Sep. 9, 2015.
Law, J., Buist, G., Haandrikman, A., Kok, J., Venema, G., and Leenhouts, K. (1995). A system to generate chromosomal mutations in Lactococcus lactis which allows fast analysis of targeted genes. Journal of Bacteriology 177(24), 7011-7018.
Lebeer, S., Claes, I.J., Verhoeven, T.L., Vanderleyden, J., and De Keersmaecker, S.C. (2011). Exopolysaccharides of Lactobacillus rhamnosus GG form a protective shield against innate immune factors in the intestine. Microb Biotechnol 4(3), 368-374. doi: 10.1111/j.1751-7915.2010.00199.x. Epub Aug. 17, 2010.
Lebeer, S., Verhoeven, T.L., Francius, G., Schoofs, G., Lambrichts, I., Dufrene, Y., et al. (2009). Identification of a Gene Cluster for the Biosynthesis of a Long, Galactose-Rich Exopolysaccharide in Lactobacillus rhamnosus GG and Functional Analysis of the Priming Glycosyltransferase. Appl Environ Microbiol 75(11), 3554-3563. doi: 10.1128/AEM.02919-08. Published online Apr. 3, 2009.
Lee, et al. Intestinal microbiota in pathophysiology and management of irritable bowel syndrome. 2014. World J Gastroenterol. 20(27): 8886-8897.
Lejeune, FJ. et al., Efficiency of Recombinant Human TNF in Human Cancer Therapy. (2006) Cancer Immun. 6:6.
Leser et al. 'Culture-independent analysis of gut bacteria: the pig gastrointestinal tract microbiota revisited'. Applied and Environmental Microbiology. 2002, vol. 68, No. 2, pp. 673-690.
Li, C.Y., Lin He Fau—Lai, C.-H., Lai Ch Fau—Lu, J.J.-Y., Lu Jj Fau—Wu, S.-F., Wu Sf Fau—Fang, S.-H., and Fang, S.H. (2011). Immunomodulatory effects of lactobacillus and Bifidobacterium on both murine and human mitogen-activated T cells. Int Arch Allergy Immunol 156(2), 128-136. doi: 10.1159/000322350.
Li, et al,. Screening and Identification of Lactobacillus animalis strain and characteristics of its bacteriostatic protein, Weishengwuxue Tongbao 2009; 36(7): 1001-1007.
Liu et al. Reclassification of Clostridium coccoides, Ruminococcus hansenii, Ruminococcus hydrogenotrophicus, Ruminococcus luti, Ruminococcus productus and Ruminococcus schinkii as *Blautia*

(56) References Cited

OTHER PUBLICATIONS

*coccoides* gen. nov., comb. nov., *Blautia hansenii* comb. nov., *Blautia hydrogenotrophica* comb. nov., *Blautia luti* comb. nov., *Blautia producta* comb. nov., *Blautia schinkii* comb. nov. and description of *Blautia wexlerae* sp. nov., isolated from human faeces. 2008. Int J Syst Evol Microbiol 58,1896-1902.

Liu, Y., et al., Human-derived probiotic Lactobacillus reuteri strains differentially reduce intestinal inflannuation (2010). American Journal of Physiology—Gastrointestinal and Liver Physiology, 299 (5), pp. G1087-G1096. Epub Aug. 26, 2010.

Ljungh, A, Wadstrorn, T. Lactic acid bacteria as probiotics (2006). Current Issues in Intestinal Microbiology, 7 (2), pp. 73-90.

Lodemann, U. et al., Effects of the Probiotic enterococcus faecium and pathogenic *escherichia coli* strains in a pig and human epithelial intestinal cell model. Hindawi publishing corporation scientifica. 2015(235184) 10 pages. Epub Mar. 26, 2015.

Lopetuso et al. Commensal Clostridia: leading players in the maintenance of gut homeostasis. 2013. Gut Pathogens, 5: 23.

Lopez, P., Gonzalez-Rodriguez, I., Sanchez, B., Ruas-Madiedo, P., Suarez, A., Margolles, A., et al. (2012). Interaction of Bifidobacterium bifidum LMG13195 with HT29 cells influences regulatory-T-cell-associated chemokine receptor expression. Appl Environ Microbiol 78(8), 2850-2857. doi: 10.1128/AEM.07581-11. Epub Feb. 17, 2012.

Lopez-Boado, Y. S. et al., Bacterial Exposure Induces and Activates Matrilysin in Mucosal Epithelial Cells. J Cell Biol148, 1305-1315 (2000).

Lozupone. Diversity, stability and resilience of the human gut microbiota. 2012. Nature. Sep. 13, 2012; 489 (7415): 220-230.

López, P., González-Rodríguez, I., Gueimonde, M., Margolles, A., and Suárez, A. (2011). Immune Response to Bifidobacterium bifidum Strains Support Treg/Th17 Plasticity. Plos One 6(9), e24776. doi: 10.1371/journal.pone.0024776. Sep. 22, 2011.

López, P., Gueimonde, M., Margolles, A., and Suárez, A. (2010). Distinct Bifidobacterium strains drive different immune responses in vitro. International Journal of Food Microbiology 138(1), 157-165. doi: https://doi.org/10.1016/j.ijfoodmicro.2009.12.023. Epub Jan. 4, 2010.

Luger, D. and Caspi, R.R., New perspectives on effector mechanisms in uveitis. (2008) Semin. Immunopathol. 30(2): 134-143. Published online Mar. 4, 2008.

Álvarez-Martin, P., O'Connell-Motherway, M., van Sinderen, D., and Mayo, B. (2007). Functional analysis of the pBC1 replicon from Bifidobacterium catenulatum L48. Applied Microbiology and Biotechnology 76(6), 1395. doi: 10.1007/S00253-007-1115-5. Aug. 17, 2007.

Lyons, et al., Bacterial strain-specific induction of Foxp3 T regulatory cells is protective in murine allergy models. Clinical & Experimental Allergy. 2010; 40:811-819. Epub Jan. 11, 2010.

MacSharry et al., Immunomodulatory effects of feeding with bifidobacterium longum on allergen-induced lung inflammation in the mouse. Pulmonary pharmacology & Therapeutics. 2012; 25:325-334. Epub Jun. 13, 2012.

Maintaining Cultures for Biotechnology and Industry (1996) Jennie C. Hunter-Cevera, Academic Press.

Manni et al., A tale of two cytokines: IL-17 and IL-22 in asthma and infection. Expert Rev Respir Med. Feb. 2014 ; 8(1): 25-42. doi:10.1586/17476348.2014.854167. Published online Dec. 10, 2013.

Mansour et al. Isolation of Enterococcus faecium NM113, Enterococcus faecium NM213 and Lactobacillus casei NM512 as novel probiotics with immunomodulatory properties. (2014) Microbiol Immunol. 58(10):559-69.

Martin R. et al., Isolation of lactobacilli from sow milk and evaluation of their probiotic potential. J of dairy research 76(4)418-425. Nov. 2009. Epub Jul. 29, 2009.

Matthes, et al., Simultaneous rapid chemical synthesis of over one hundred oligonucleotides on a microscale. Apr. 1984. EMBO Journal, 3(4): p. 801-805.

Maya, J.R. et al., Emerging Therapies for Noninfectious Uveitis: What May Be Coming to the Clinics. (2014) J. Ophthalmology. 310329. Epub Apr. 24, 2014.

Mazmanian, SK., An immunomodulatory molecule of symbiotic bacteria directs maturation of the host immune system. Cell. Jul. 15, 2005;122(1):107-18.

Mccarville, J.L., Dong, J., Caminero, A., Bermudez-Brito, M., Jury, J., Murray, J.A., et al. (2017). A Commensal Bifidobacterium longum Strain Prevents Gluten-Related Immunopathology in Mice through Expression of a Serine Protease Inhibitor. Applied and Environmental Microbiology 83(19), e01323-01317. doi: 10.1128/AEM.01323-17. Print Oct. 1, 2017.

McClymont, S.A., Putnam Al Fau—Lee, M.R., Lee Mr Fau—Esensten, J.H., Esensten Jh Fau—Liu, W., Liu W Fau—Hulme, M.A., Hulme Ma Fau—Hoffmuller, U., et al. (2011). Plasticity of human regulatory T cells in healthy subjects and patients with type 1 diabetes. Journal of Immunology 186(7), 3918-3926. doi: 10.4049/jimmunol.1003099.

Menard, S., Laharie D Fau—Asensio, C., Asensio C Fau—Vidal-Martinez, T., Vidal-Martinez T Fau—Candalh, C., Candalh C Fau—Rullier, A., Rullier A Fau—Zerbib, F., et al. (2005). Bifidobacterium breve and *Streptococcus thermophilus* secretion products enhance T helper 1 immune response and intestinal barrier in mice. Experimental Biology and Medicine (Maywood) 230(10), 749-756.

Meyza, et al. The BTBR mouse model of idiopathic autism—Current view on mechanisms. 2017. Neurosci Biobehav Rev.;76(Pt A):99-110. Epub Feb. 3, 2017.

Milani, C., Mangifesta, M., Mancabelli, L., Lugli, G.A., Mancino, W., Viappiani, A., et al. (2017). The Sortase-Dependent Fimbriome of the Genus *Bifidobacterium*: Extracellular Structures with Potential to Modulate Microbe-Host Dialogue. Appl Environ Microbiol 83(19). doi: 10.1128/AEM.01295-17.

Miossec, P. et al., Targeting IL-17 and TH17 cells in chronic inflammation, Oct. 2012; Nature Rev Drug Discovery 11(10), 763-776. doi: 10.1038/nrd3794.

Miraglia Del Giudice, M., Indolfi, C., Capasso, M., Maiello, N., Decimo, F., and Ciprandi, G. (2017). Bifidobacterium mixture (B longum BB536, B infantis M-63, B breve M-16V) treatment in children with seasonal allergic rhinitis and intermittent asthma. Italian Journal of Pediatrics 43(1), 25. doi: 10.1186/s13052-017-0340-5.

Miyake, T. et al., Phylogenetic analysis of the genus bifidobacterium and related genera based on 16S rDNA sequences. Microbiol. Immunol. 1998; 42(10): 661-667.

Miyauchi, E., Control of multiple sclerosis by gut microbiota. Journal of clinical and experimental medicine. 2015. vol. 253 No. 5.2, pp. 445-450.

Molecular Biology Techniques, 1st edition. An intensive laboratory course. 1998.

Molecular Biology Techniques: An Intensive Laboratory Course, (Ream et al., eds., 1998, Academic Press).

Mortaz, E. et, al., Anti-Inflammatory Effects of Lactobacillus Rahmosus and Bifidobacterium Breve on Cigarette Smoke Activated Human Mcrophiages, PLoS ONE, Apr. 21, 2015, 10(8):e0136455.DOI:10.1371, Journal.pone.0136455.

Mucientes, A. et al., Specific association of IL17A genetic variants with panuveitis. (2015) Br J Ophthalmol. 99(4):566-70. Epub Jan. 16, 2015.

Mukai et al., SH3BP2 Gain-Of-Function Mutation Exacerbates Inflammation and Bone Loss in a Murine Collagen-Induced Arthritis Model, 2014 PLoS ONE 9(8): e105518. Aug. 21, 2014.

Mulder et al. 'Environmentally-acquired bacteria influence microbial diversity and natural innate immune responses at gut surfaces'. Bmc Biology. 2009, vol. 7, No. 1, p. 79 . Published: Nov. 20, 2009.

Murofushi, Y., Villena, J., Morie, K., Kanmani, P., Tohno, M., Shimazu, T., et al. (2015). The tolllike receptor family protein RP105/MD1 complex is involved in the immunoregulatory effect of exopolysaccharides from Lactobacillus plantarum N14. Mol Immunol 64(1), 63-75. doi: 10.1016/j.molimm.2014.10.027. Epub Nov. 13, 2014.

Narushima, et al., Characterization of the 17 strains of regulatory T cell-inducing human-derived Clostridia. Gut Microbes Mar. 18, 2014; 5:3, 333-339.

(56) References Cited

OTHER PUBLICATIONS

Naughton PJ; Grant G. (2005) Modelling of salmonellosis in: Microbial Ecology of the Growing Animal Holzapfel WH, Naughton PJ. (Eds). London, Elsevier, pp. 235-257.
Neeser, J.R., et al., Lactobacillus johnsonii La1 shares carbohydrate-binding specificities with several enteropathogenic bacteria (2000). Glycobiology, 10 (11), pp. 1193-1199.
Neish, A. S. et al., Prokaryotic Regulation of Epithelial Responses by Inhibition of IκB-α Ubiquitination. Science 289, 1560 (2000).
Nemeth et al. 'Inhibition of *Salmonella*-induced IL-8 synthesis and expression of Hsp70 in enterocyte-like Caco-2 cells after exposure to non-starter lactobacilli'. International Journal of Food Microbiology. 2006, vol. 112, No. 3, pp. 266-274. Epub Oct. 12, 2006.
Nicolau, D.P. Current challenges in the management of the infected patient (2011). Current Opinion in Infectious Diseases, 24 (Suppl1), pp. S1-S10.
Notice of Allowance dated Mar. 30, 2011 for U.S. Appl. No. 10/285,224.
Notice of Allowance dated Apr. 25, 2016 for U.S. Appl. No. 14/232,475.
Notice of Allowance dated Aug. 23, 2016 for U.S. Appl. No. 14/232,475.
Notice of allowance dated Sep. 1, 2017 for U.S. Appl. No. 15/357,850.
Notice of Allowance dated Nov. 22, 2017 for U.S. Appl. No. 15/359,988.
Notice of Publication dated Dec. 27, 2018 for U.S. Appl. No. 16/022,256.
Nuala Moran: 'Microbial wealth', chemistry and industry, 78(6), Jun. 1, 2014, pp. 20-23, XP055252922.
Numasaki, M. et al., IL-17 Enhances the Net Angiogenic Activity and In Vivo Growth of Human Non-Small Cell Lung Cancer in SCID Mice through Promoting CXCR-2-Dependent Angiogenesis. (2005) J. Immunol. 175: 6177-6189. Nov. 1, 2005.
Numasaki, M. et al., Interleukin-17 promotes angiogenesis and tumor growth. Blood. Apr. 1, 2003;101(7):2620-7. Epub Oct. 31, 2002.
O'Connell Motherway, M., Kinsella, M., Fitzgerald, G.F., and Sinderen, D. (2013). Transcriptional and functional characterization of genetic elements involved in galacto-oligosaccharide utilization by Bifidobacterium breve UCC2003. Microbial biotechnology 6(1), 67-79. doi: 10.1111/1751-7915.12011. Epub Dec. 2, 2012.
O'Connell Motherway, M., O'Driscoll, J., Fitzgerald Gerald, F., and Van Sinderen, D. (2009). Overcoming the restriction barrier to plasmid transformation and targeted mutagenesis in Bifidobacterium breve UCC2003. Microbial Biotechnology 2(3), 321-332. doi: 10.1111/j.1751-7915.2008.00071.x. Published online Apr. 17, 2009.
O'Connell Motherway, M., Zomer, A., Leahy, S.C., Reunanen, J., Bottacini, F., Claesson, M.J., et al. (2011). Functional genome analysis of Bifidobacterium breve UCC2003 reveals type IVb tight adherence (Tad) pili as an essential and conserved host-colonization factor. Proc Natl Acad Sci U S A 108(27), 11217-11222. doi: 10.1073/pnas.1105380108. Epub Jun. 20, 2011.
Odamaki, Toshitaka et al., "Age-related changes in gut microbiota composition from newborn to centenarian: a cross-sectional study," BMC Microbiology (2016) 16:90, pp. 1-12, DOI 10.1186/S12866-016-0708-5. Published: May 25, 2016.
Office Action dated Mar. 19, 2019 for U.S. Appl. No. 16/031,024.
Ohashi, Y., Ushida, K. Health-beneficial effects ofprobiotics: Its mode of action (2009). Animal Science Journal, 80 (4), pp. 361-371.
Oladipo, et al., Bioprotective potential of bacteriocinogenic enterococcus gallinarum strains isolated from some Nigerian fermented foods, and of their bacteriocins. Polish Journal of Microbiology. 2014; 63(4): 415-422.
Olivares, M., Castillejo, G., Varea, V., and Sanz, Y. (2014). Double-blind, randomised, placebo-controlled intervention trial to evaluate the effects of Bifidobacterium longum CECT 7347 in children with newly diagnosed coeliac disease. British Journal of Nutrition 112(1), 30-40. doi: 10.1017/S0007114514000609. Epub Apr. 28, 2014.

O'Sullivan et al., "Bacterial Supplementation in the Irritable Bowel Syndrome. A Randomised Double-Blind Placebo-Controlled Crossover Study", Digest Liver Dis. 2000. pp. 294-301.
Overbeek, R., Begley, T., Butler, R.M., Choudhuri, J.V., Chuang, H.-Y., Cohoon, M., et al. (2005). The Subsystems Approach to Genome Annotation and its Use in the Project to Annotate 1000 Genomes. Nucleic Acids Research 33(17), 5691-5702. doi: 10.1093/nar/gki866.
Pace et al. Macrophage activiation: Priming activity from a T-cell hybridoma is attributable to interferon. (1983) PNAS. 80:3782-6.
Pang, et al., Crystal structure of human pirin: an iron-binding nuclear protein and transcription cofactor. Journal of Biological Chemistry, 279(2); Jan. 9, 2004:1491-1498. Epub Oct. 22, 2003.
Parabacteroides distasonis (Eggerth and Gagnon) Sakamoto and Benno (ATCC 8503). Sep. 19, 2017. 2 Pages.
Park, S.K. et al., *Blautia stercoris* sp. nov., isolated from human faeces. International journal of systematic and evolutionary microbiology. 2012; 62(4): 776-779. Epub May 13, 2011.
Patel., R. et al., Determination of 16S rRNA sequences of enterococci and application to species identification of nonmotile enterococcus gallinarum isolates. Journal of clinical microbiology, 1998; 36(11):3399-3407.
Paustian, C., Taylor, P., Johnson, T., Xu, M., Ramirez, N., Rosenthal, K.S., et al. (2013). Extracellular ATP and Toll-like receptor 2 agonists trigger in human monocytes an activation program that favors T helper 17. PLoS One 8(1), e54804. doi: 10.1371/journal.pone.0054804. Epub Jan. 31, 2013.
Coakley M et al.: Intestinal bifidobacteria that produce trans-9, trans-11 conjugated linoleicacid: A fatty acid with antiproliferative activity against human colon SW480and HT-29 cancer cells, Nutrition and Cancer, Taylor & Francis Group, US vol. 56, No. 1, Jan. 1, 2006 (Jan. 1, 2006), pp. 95-102, XP008087265, ISSN: 0163-5581, DOI:10.1207/515327914NC5601 13 cf. abstract, p. 101, last para, of the right-hand col.
PCR (Introduction to Biotechniques Series), 2nd ed. (Newton & Graham eds., 1997, Springer Verlag).
PCT/EP2017/025038 International Preliminary Report on Patentability dated Jun. 6, 2018, 8 Pages.
PCT/EP2017/025038 International Search Report and Written Report dated Jun. 12, 2017.
PCT/EP2017/025038 Written Opinion of the International Preliminary Examining Authority dated Jan. 1, 2018.
PCT/EP2017/025038 Written Opinion of the International Preliminary Examining Authority dated Jan. 25, 2018.
PCT/GB2017/052076 Written Opinion of the International Preliminary Examining Authority dated Jun. 21, 2018, 11 Pages.
PCT/GB2017/052077 International Search Report dated Oct. 16, 2017.
PCT/GB2017/052077 Written Opinion dated Oct. 16, 2017.
PCT/GB2017/052077 Written Opinion of the International Preliminary Examining Authority dated Jun. 21, 2018, 10 Pages.
Database WPI, Week 201801, Thomson Scientific, London, GB; AN 2017-834299, XP002787097, & WO 2017/209156 AI (Morinaga Milk Ind Co. Ltd) Dec. 7, 2017 (Dec. 7, 2017) * abstract * of WO2017/2019156, Kobayashi, Youdai et al.
Devillard, E. et al., Metabolism of Linoleic Acid by Human Gut Bacteria: Different Routes for Biosynthesis of Conjugated Linoleic Acid, Journal O. Bacteriology, 2007, vol. 189, No. 4, p. 2544-2570. Published online Jan. 5, 2007.
Pearson, WR. An introduction to sequence similarity ("Homology") searching. Current protocols in bioinformatics/editoral board, Andreas D Baxevanis. [et al], 2013; 0 3:10.1002/0471250953.bi0301 s42. doi: 10.1002/0471250953.bi0301s42.
Petersen et al. Intestinal colonization with phylogenetic group B2 *Escherichia coli* related to inflammatory bowel disease: a systematic review and meta-analysis. 2015. Scand J Gastroenterol. ;50(10):1199-207. Epub Apr. 24, 2015.
Petsuriyawong et al. 'Screening of probiotic lactic acid bacteria from piglet feces'. Nature Science. 2011, vol. 45, pp. 245-253.
Hoarau, Cyrille et al., Supernatant from Bifidobacterium Differentially Modulates Transduction Signaling Pathways for Biological Functions of Human Dendritic Cells, Plos One, Public Library of Science, US, vol. 3, No. 7, Jul. 1, 2008 (Jan. 7, 2008), p. e2753-1,

(56) References Cited

OTHER PUBLICATIONS

XP009139666,ISSN: 1932-6203 *cf. abstract and conclusion, furthermore discussion part at p. 3, col. at the right side*.
Pinto-Sánchez, M.I., Smecuol, E.C., Temprano, M.P., Sugai, E., González, A., Moreno, M.L., et al. (2017). Bifidobacterium infantis NLS Super Strain Reduces the Expression of α-Defensin-5, a Marker of Innate Immunity, in the Mucosa of Active Celiac Disease Patients. Journal of Clinical Gastroenterology 51(9), 814-817. doi: 10.1097/mcg.0000000000000687.
Database WPI,Week 201801, Thomson Scientific, London, GB; AN 2017-834299, XP002787097,& WO 2017/209156 AI (Morinaga Milk Ind Co Ltd) Dec. 7, 2017 (Dec. 7, 2017) * abstract *.
Hoarau et al.: "TLR2 Activation by Supernatant From Bifidobacterium Breve Modulates Maturation and Survival of Human DCs via Differential Effects on PI3Kinase, p38 and ERK Pathways",Journal of Allergy and Clinical Immuno, Elsevier, Amsterdam, NL, vol. 119, No. 1, Jan. 1, 2007 (Jan. 1, 2007), p. S258, XP005756921, ISSN: 0091-6749, DOI: 10.1016/J.JACI.2006.12.377 *cf. abs.No. 1008 at p. S258*.
Liu, Chang-jian et al., Antioxidant and Cholesterol-Reducing Properties of Enterococcus gallinarum m661, Bioengineering (Food Science), vol. 34, No. 7, Dec. 31, 2013, pp. 157-161.
Matsuda F et al.: Evaluation of a probiotics,BBG-01, for enhancement of immunogenicity of an oral inactivated cholera vaccine and safety: A randomized, double-blind, placebo-controlled trial in Bangladeshi children under 5 years of age,Vaccine, Elsevier, Amsterdam, NL, vol. 29, No. 10, Dec. 26, 2010 (Dec. 26, 2010), pp. 1855-1858, XP028147184, ISSN: 0264-410X, DOI: 10.1016/J.VACCINE.2010.12.133 [retrieved on Jan. 7, 2011] *cf. abstract*.
Scutto, Angelo et al., In silico mining and characterization of bifidobacterial lipoprotein with CHHP domain secreted in an aggregated form, International J. of Biol. Macromolecutes 82(2016), 653-662. Oct. 12, 2015.
Rajilic-Stojanovic, et al. The first 1000 cultures species of the human gastrointestinal micriobiota. FEMS Mlcriobiol Rev, vol. 38, 2014. pp. 996-1047. Epub Jun. 27, 2014.
Reddy, K.B.P.K., et al., Role of cryoprotectants on the viability and functional properties of pro biotic lactic acid bacteria during freeze drying (2009). Food Biotechnology, 23 (3), pp. 243-265. Published online: Aug. 3, 2009.
Remington. Remington: The science and practice of pharmacy. 20th Edition. Gennaro, Eds. Lippincott Williams & Wilkins, 2003.
Reuter, G. (2001). The Lactobacillus and Bifidobacterium microflora of the human intestine: composition and succession. Current Issues in Intestinal Microbiology 2(2), 43-53.
Rhee, Young-Kyung et al.., Antihumor Activity of Bifidobacterium Spp. isolated from a healthy Korean, Arch Pharm Res vol. 23, No. t, 482-487 2000. Oct. 2000.
Riquelme. Will 4D Pharma be UK's next Microbiome leader? Feb. 2, 2015, LABIOTECH.eu [online].
Robertson, J.M.C., et al., Lack of flagella disadvantages Salmonella enterica serovar Enteritidis during the early stages of infection in the rat (2003). Journal of Medical Microbiology, 52 (1), pp. 91-99.
Robinson, et al. Inside information—The unique features of visceral sensation. 2008. Mol Interv, 8(5): 242-253.
Rockwell, S.C. et al., Characteristics of a Serially Transplanted Mouse Mammary Tumor and Its Tissue-Culture-Adapted Derivative. (1972) J Natl Cancer Inst. 49:735-49.
Rong, Y., Dong, Z., Hong, Z., Jin, Y., Zhang, W., Zhang, B., et al. (2017). Reactivity toward Bifidobacterium longum and Enterococcus hirae demonstrate robust CD8(+) T cell response and better prognosis in HBV-related hepatocellular carcinoma. Experimental Cell Research 358(2), 352-359. doi: 10.1016/j.yexcr.2017.07.009. Epub Jul. 8, 2017.
Roseburia. Ubiome, 2018. Accessed on Jun. 25, 2018; Available at: https://shop.ubiome.com/pages/roseburia-1.
Ruiz, L., Delgado, S., Ruas-Madiedo, P., Margolles, A., and Sanchez, B. (2016). Proteinaceous Molecules Mediating Bifidobacterium-Host Interactions. Front Microbiol 7, 1193. doi: 10.3389/fmicb.2016.01193. Published online Aug. 3, 2016.
Ruiz, P.A., Hoffmann, M., Szcesny, S., Blaut, M., and Haller, D. (2005). Innate mechanisms for Bifidobacterium lactis to activate transient pro-inflammatory host responses in intestinal epithelial cells after the colonization of germ-free rats. Immunology 115(4), 441-450. doi: 10.1111/j.1365-2567.2005.02176.x.
Sagar, et al., Bifidobacterium breve and lactobacillus rhamnosus treatment is as effective as budesonide at reducing inflammation in a murine model for chronic asthma. Respiratory Research. 2014; 15(46):1-17. Published: Apr. 16, 2014.
Saiki, et al., Primer-directed enzymatic amplification of DNA with a thermostable DNA polymerase. 1988. Science, 239. pp. 487-491. Jan. 29, 1988.
Sakamato, et al., Parabacteroides faecis sp. nov., isolated from human faeces. International Journal of Systematic and Evolutionary Microbiology (2015), 65, 1342-1346. Epub Feb. 9, 2015.
Sakamoto, et al., Parabacteroides gordonii sp. nov., isolated from human blood cultures. International Journal of Systematic and Evolutionary Microbiology (2009), 59, 2843-2847. Epub Jul. 23, 2009.
Sakamoto, et al., Parabacteroides johnsonii sp. nov., isolated from human faeces. International Journal of Systematic and Evolutionary Microbiology (2007), 57, 293-296.
Sakamoto, M. et al., Reclassification of Bacteroides distasonis, Bacteroides goldsteinii and Bacteroides merdae as Parabacteroides distasonis gen. nov., comb, nov., Parabacteroides goldsteinii comb. nov. and Parabacteroides merdae comb. nov. International journal of systematic and evolutionary microbiology. 2006; 56: 1599-1605. DOI 10.1099/ijs.0.0641920.
SALIX Pharmaceuticals, Inc. FDA Highlights of Prescribing Information—XIFAXAN (rifaximin tablet). Revised Nov. 2015.
Scher et al., Expansion of intestinal Prevotella copri correlates with enhanced susceptibility to arthritis. 2013; eLIFE 2, e01202, 20 Pages.
Schiavi, E., Gleinser, M., Molloy, E., Groeger, D., Frei, R., Ferstl, R., et al. (2016). The Surface-Associated Exopolysaccharide of Bifidobacterium longum 35624 Plays an Essential Role in Dampening Host Proinflammatory Responses and Repressing Local TH17 Responses. Appl Environ Microbiol 82(24), 7185-7196. doi: 10.1128/AEM.02238-16.
Schiavi, E., Plattner, S., Rodriguez-Perez, N., Barcik, W., Frei, R., Ferstl, R., et al. (2018). Exopolysaccharide from Bifidobacterium longum subsp. longum 35624 modulates murine allergic airway responses. Benef Microbes, 1-14. doi: 10.3920/BM2017.0180. Epub May 4, 2018.
Schleifer, K.H. et al., Transfer of Streptococcus faecalis and Streptococcus faecium to the Genus Enterococcus nom. rev. as Enterococcus faecalis comb. nov. and Enterococcus faecium comb. nov. Int J Syst Evol Microbiol, Jan. 1984 34: 31-34, doi:10.1099/00207713-34-1-31. Jan. 1, 1984.
Schmitz, S. et al., A prospective, randomized, blinded, placebo-controlled pilot study on the effect of Enterococcus faecium on clinical activity and intestinal gene expression in canine food-responsive chronic enteropathy. J Vet Intern Med. Mar. 2015-Apr. 29(2):533-43. doi: 10.1111/jvim.12563. Epub Mar. 16, 2015.
Schouten, et al., Cow milk allergy symptoms are reduced in mice fed dietary synbiotics during oral sensitization with whey. J Nutr. Nutritional Immunology. Jul. 2009; 139(7): 1398-403. Epub May 27, 2009.
Schreiber, O, et al., Lactobacillus reuteri prevents colitis by reducing P-selectin-associated leukocyte- and plateletendothelial cell interactions (2009). American Journal of Physiology-Gastrointestinal and Liver Physiology, 296 (3), pp. G534-G542. Epub Jan. 15, 2009.
Schwiertz, et al., Quantification of Different Eubacterium spp. in Human Fecal Samples with Species-Specific 16S rRNA-Targeted Oligonucleotide Probes. Applied and environmental biology, vol. 66, No. 1, Jan. 1, 2000; pp. 375-382.
Severijnen, A. J. et al., Chronic Arthritis Induced in Rats by Cell Wall Fragments of Eubacterium Species from the Human Intestinal Flora. Infection and Immunity, Feb. 1990, vol. 58, No. 2, 523-528.
Sgadari, C. et al., Interferon-inducible protein-10 identified as a mediator of tumor necrosis in vivo. (1996) PNAS. 93:13791-6. Nov. 26, 1996.

(56) References Cited

OTHER PUBLICATIONS

Sgadari et al. Mig, the Monokine Induced By Interferon-g, Promotes Tumor Necrosis In Vivo. (1997) Blood. 89:2635-43.
Simon, et al., Peptoids: A modular approach to drug discover, Oct. 1992. PNAS, 89(20):9367-9371.
Simpson-Herren, L. et al., Kinetic parameters and growth curves for experimental tumor systems. Cancer Chemother Rep. Jun. 1970;54(3):143-74.
Sisson, G. et al., Randomised clinical trial: a liquid multi-strain probiotic vs. placebo in the irritable bowel syndrome—a 12 week double-blind study. Aliment Pharmacol Ther. 2014; 40: 51-62. Epub May 11, 2014.
Sivan, A., Corrales, L., Hubert, N., Williams, J.B., Aquino-Michaels, K., Earley, Z.M., et al. (2015). Commensal Bifidobacterium promotes antitumor immunity and facilitates anti-PD-L1 efficacy. Science 350(6264), 1084-1089. doi: 10.1126/science.aac4255. Epub Nov. 5, 2015.
Sivieri, K et al., Probiotic enterococcus faecium CRL 183 inhibit chemically induced colon cancer in male wistar rats. Eur Food Res Technol. Dec. 2008; 228:231-237.
Skolnick, et al. From genes to protein structure and function: novel applications of computational approaches in the genomic era. Trends Biotechnol. Jan. 2000;18(1):34-9. Review.
Smith, C.L., et al., Lactobacillus fermentum BRII and fmctooligosaccharide partially reduce jejunal inflammation in a model of intestinal mucositis in rats (2008). Nutrition and Cancer, 60 (6), pp. 757-767.
Song et al., Impact of Schistosoma japonicum Infection on Collagen-Induced Arthritis in DBA/1 Mice: A Murine Model of Human Rheumatoid Arthritis. 2011; PLoS ONE 6, e23453, 10 pages. Epub Aug. 8, 2011.
Song, Yuli et al., *Bacteroides goldsteinii* sp. nov. Isolated from Clinical Specimens of Human Intestinal Origin, J. Clinical Microbiology, Sep. 2005, p. 4522-4527. DOI:10.1128/JCM.43.9.4522-4527.2005.
Sonnenburg, et al., Genomic and Metabolic Studies of the Impact of Probiotics on a Model Gut Symbiont and Host. PLoS Biol 2006, 4(12): e413. https://doi.org/10.1371/journal.pbio.0040413.
U.S. Appl. No. 15/915,889 Notice of Allowance dated Jun. 4, 2018.
Written Opinion for PCT/US2017/066709 dated Apr. 6, 2018 (Published as WO2018112363) owned by Evelo Biosciences, Inc.
Stokholm, et al., Maturation of the gut microbiome and risk of asthma in childhood. Nature Communications, 2018; 9(141): 1-10.
Stoll et al., Altered microbiota associated with abnormal humoral immune responses to commensal organisms in enthesitis-related arthritis, 2014; Arthritis Res Ther. 16:486.
Strasser, S. et al., Influence of lyophilization, fluidized bed drying, addition of protectants, and storage on the viability oflactic acid bacteria (2009). Journal of Applied Microbiology, 107 (1), pp. 167-177. Epub Mar. 3, 2009.
Strickertsson, J.A. et al., Enterococcus faecalis Infection and Reactive Oxygen Species Down-Regulates the miR-17-92 Cluster in Gastric Adenocarcinoma Cell Culture. Genes 2014, 5(3), 726-738.
Strus et al. Distinct effects of Lactobacillus plantarum KL30B and *Escherichia coli* 3A1 on the induction and development of acute and chronic inflammation. 2015. Cent Eur J Immunol.40(4):420-30. Epub Jan. 15, 2016.
Sun, D. et al., The role of Th17-associated cytokines in the pathogenesis of experimental autoimmune uveitis (EAU). (2015) Cytokine. 74(1):76-80. Epub Mar. 2, 2015.
Sun, et al., Exploring gut microbes in human health and disease: Pushing the envelope. Genes Dis. Dec. 2014; 1(2):132-139.doi:10.1016/j.gendis.2014.08.001. Published online Aug. 10, 2014.
Supplement to: ISRAEL, et al., Severe and difficult-to-treat asthma in adults. N Engl J Med 2017;377:965-76.
Tahoun, A., Masutani, H., El-Sharkawy, H., Gillespie, T., Honda, R.P., Kuwata, K., et al. (2017). Capsular polysaccharide inhibits adhesion of Bifidobacterium longum 105-A to enterocyte-like Caco-2 cells and phagocytosis by macrophages. Gut Pathog 9, 27. doi: 10.1186/s13099-017-0177-x.

Tan, Hai-Qin et al., *Parabacteroides chartae* sp. nov., an obligately anaerobic species from wastewater of a paper mill, International Journal of systematic and Evolutionary Microbiology (2012), 62-2613-2617, DOI 10.1099/ijs.0.038000-0.
Tanaka, K. and Watanabe, K., In Vitro tebipenem activity against anaerobic bacteria. Japanese Journal of Chemotherapy. Mar. 2009. vol. 57 S-1.
Tap et al. Towards the human intestinal microbiota phylogenetic core. 2009. Environ Microbiol, 11 (10):2574-84. Epub Jul. 6, 2009.
Tatusova et al., BLAST 2 Sequences, a new tool for comparing protein and nucleotidesequences, FEMS Microbiology Letters 174 (1999) 247-250.
Tatusova et al., Erratum to BLAST 2 Sequences, a new tool for comparing protein and nucleotide sequences, [FEMS Microbiol. 174 (1999) 247-250], FEMS Microbiology Letters 177 (1999) 187-188.
Teng, L. J. et al., PCR Assay for Species-Specific Identification of Bacteroides thetaiotaomicron. J Clin Microbiol38, 1672-1675 (2000).
Terciz, Janos et al., Inflammation and Colon Cancer, Gastroenterology, 2010: 138: 2101-2114.
Tomas, M.S.J., et al., Stability of freeze-dried vaginal Lactobacillus strains in the presence of different lyoprotectors (2009). Canadian Journal of Microbiology, 55 (5), pp. 544-552.
Tomosada, Y., Villena, J., Murata, K., Chiba, E., Shimazu, T., Aso, H., et al. (2013). Immunoregulatory Effect of Bifidobacteria Strains in Porcine Intestinal Epithelial Cells through Modulation of Ubiquitin-Editing Enzyme A20 Expression. PLOS ONE 8(3), e59259. doi: 10.1371/journal.pone.0059259. Epub Mar. 26, 2013.
Toomer, O. et al., Maternal and postnatal dietary probiotic supplementation enhances splenic regulatory T helper cell population and reduces peanut allergen-induced hypersensitivity responses in mice. Immunobiology. 209; 2014: 661-670. Epub May 14, 2014.
Tsukinowa, et al., Fecal microbiota of a dugong (*Dugong dugong*) in captivity at Toba Aquarium. J. Gen. Appl. Microbiol., 54, 25-38 (2008).
Turnbaugh et al. A core gut microbiome in obese and lean twins. Jan. 22, 2009. Nature, 457(7228): 480-484. Epub Nov. 30, 2008.
Turroni, F., Taverniti V Fau—Ruas-Madiedo, P., Ruas-Madiedo P Fau—Duranti, S., Duranti S Fau—Guglielmetti, S., Guglielmetti S Fau—Lugli, G.A., Lugli Ga Fau—Gioiosa, L., et al. (2014). Bifidobacterium bifidum PRL2010 modulates the host innate immune response. Appl Environ Microbiol 80(1098-5336 (Electronic)), 730-740.
Tzortzis, G., et al., Modulation of anti-pathogenic activity in canine-derived *Lactobacillus* species by carbohydrate growth substrate (2004). Journal of Applied Microbiology, 96 (3), pp. 552-559.
Udayappan, et al., Oral treatment with Eubacterium hallii improves insulin sensitivity in db/db mice. NPJ Biofilms and microbiomes, vol. 2, Jul. 6, 2016; p. 16009.
Udayappan et al., PS4-5. Administration of Eubacterium hallii improves insulin sensitivity and degree of liversteatosis in male db/db mice. Nederlands tijdschrift voor diabetologie, vol. 11, No. 4., Nov. 23, 2013.pp. 145.
Untergasser, A., Nijveen, H., Rao, X., Bisseling, T., Geurts, R., and Leunissen, J.A. (2007). Primer3Plus, an enhanced web interface to Primer3. Nucleic Acids Res 35(Web Server issue), W71-74. doi: 10.1093/nar/gkm306.
U.S. Appl. No. 15/357,936 Notice of Allowance dated Apr. 18, 2018.
U.S. Appl. No. 15/359,144 Notice of Allowance dated Sep. 4, 2018.
U.S. Appl. No. 15/359,972 Notice of Allowance dated Aug. 8, 2018.
U.S. Appl. No. 15/359,988 Notice of Allowance dated Mar. 2, 2018.
U.S. Appl. No. 15/359,988 Notice of Allowance dated Mar. 16, 2018.
U.S. Appl. No. 15/592,178 Notice of Allowance dated Apr. 12, 2018.
U.S. Appl. No. 15/592,178 Notice of Allowance dated Jul. 12, 2018.
U.S. Appl. No. 15/631,945 Notice of Allowance dated Oct. 18, 2018.
U.S. Appl. No. 15/700,007 Notice of Allowance dated Oct. 17, 2018.
U.S. Appl. No. 15/915,885 Notice of Allowance dated May 23, 2018.

(56) References Cited

OTHER PUBLICATIONS

U.S. Appl. No. 15/916,167 Notice of Allowance dated May 31, 2018.
U.S. Appl. No. 15/916,202 Notice of Allowance dated Jun. 11, 2018.
U.S. Appl. No. 15/916,205 Notice of Allowance dated May 30, 2018.
U.S. Appl. No. 15/431,393 Office Action dated Jul. 30, 2018.
U.S. Appl. No. 15/631,945 Office Action dated May 15, 2018.
U.S. Appl. No. 15/700,007 Non-Final Office Action dated Jun. 10, 2019.
U.S. Appl. No. 15/803,723 Notice of Allowance dated Feb. 13, 2018.
U.S. Appl. No. 15/842,635 Non-Final Office Action dated May 29, 2019.
Van de Bogert, et al., Immunomodulatory properties of streptococcus and veillonella isolates from the human small intestine microbiota, PLOS One, Dec. 2014: 1-20, DOI:10.1371/journal.pone.0114277.
Van de Pol, M.A et al., Sybiotics reduce allergen-induced T-helper 2 respond and improve peak expiatory flow in allergic asthmatics, Allergy 2011 ;66:39-47. Epub Aug. 17, 2010.
Van de Veerdonk, et al., The Anti-CD20 antibody rituximab reduces the Th17 cell response. Arthritis & Rheumatism. Jun. 2011; 63(6):1507-1516.
Van Nevel et al., "Conrol of Rumen Methanogenesis." Environmental Monitoring and Assessment, vol. 42, 1996, p. 73097, XP000979267.
Van Tilburg, M. Can we treat visceral hypersensitivity in functional abdominal pain? Lancet Gastroenterolhepatol, 2017; 2 Pages. . 2(10):694-695. doi: 10.1016/82468-1253(17)30258-3. Epub Aug. 18, 2017.
Verheijden, K.A.T. et al., The development of allergic inflammation in a murine house dust mite asthma is suppressed by symbiotic mixtures of non-digestible oligosaccharides and Bifidobacterium breve M-16V; Eur. J. Nut. (2016) 55: 1141-1151, DOI 10.1007, 500394-015-0928-8. Epub May 24, 2015.
Vetrovsky, T. and Baldrian, P., The variability of the 16S rRNA gene in bacterial genomes and its consequences for bacterial community analyses. Plos One. Feb. 2013; 8(2): e57923. Epub Feb. 27, 2013.
Viaud, Sophie et al. "The intestinal microbiota modulates the anticancer immune effects of cyclophosphamide." Science (New York, N.Y.) vol. 342,6161 (2013): 971-6. doi:10.1126/science. 1240537. Nov. 22, 2013.
Wang, Chun-Sai-Er, et al., VSL#3 can prevent ulcerative colitis-associated carcinogenesis in mice, Oct. 7, 2018, vol. 24, Issue 37, pp. 4254-4262.
Wang et al. 16S rRNA gene-based analysis of fecal microbiota from preterm infants with and without necrotizing enterocolitis. 2009. ISME J. 3(8): 944-954. Epub Apr. 16, 2009.
Wang, Feng, Bifidobacterium can mitigate intestinal immunopathology in the context of CTLA-4 blockade, PNA, Jan. 2, 2018 vol. 115, No. 1, pp. 157-161. . Epub Dec. 18, 2017.
Wang, G., Xia, Y., Cui, J., Gu, Z., Song, Y., Q., C.Y., et al. (2014). The Roles of Moonlighting Proteins in Bacteria. Current Issues in Molecular Biology 16, 15-22. Epub Jul. 22, 2013.
Wang, R.F., and Kushner, S.R. (1991). Construction of versatile low-copy-numbers vectors for cloning, sequencing and gene expression in *Escherichia coli*. Gene 100, 195-199. doi: https://doi.org/10.1016/0378-1119(91)90366-J.
Wang W., Lyophilization and development of solid protein pharmaceuticals. International J. Pharmaceutics 203: 1-60, 2000.
Wei, X., Yan, X., Chen, X., Yang, Z., Li, H., Zou, D., et al. (2014). Proteomic analysis of the interaction of Bifidobacterium longum NCC2705 with the intestine cells Caco-2 and identification of plasminogen receptors. J Proteomics 108, 89-98. doi: 10.1016/j.jprot.2014.04.038. Epub May 17, 2014.
Welman, A.D., and Maddox, I.S. (2003). Exopolysaccharides from lactic acid bacteria: perspectives and challenges. Trends in Biotechnology 21(6), 269-274. doi: https://doi.org/10.1016/S0167-7799(03)00107-0.
Wendler, et al., Identification of a pirin, a novel highly conserved nuclear protein. J. Biol Chem. Mar. 28, 1997; 272(13):8482-9.
Wenzel, S.E., Asthma phenotypes: the evolution from clinical to molecular approaches, Nature medicine, May 2012; 18(5):716-725.
Westermann, C., Gleinser, M., Corr, S.C., and Riedel, C.U. (2016). A Critical Evaluation of Bifidobacterial Adhesion to the Host Tissue. Front Microbiol 7, 1220. doi: 10.3389/fmicb.2016.01220. Aug. 5, 2016.
Williams, N.T. Probiotics (2010). American Journal of Health-System Pharmacy, 67 (6), pp. 449-458. Mar. 15, 2010.
Workman et al. Guidelines for the welfare and use of animals in cancer research (2010) Br. J. Cancer. 102:1555-77.
Written Opinion for PCT/US2017/066713 dated Aug. 13, 2018 (Published as WO2018/112365) owned by Evelo Biosciences, Inc.
Wrzosek, et al., Bacteroides thetaiotaomicron and Faecalibacterium prausnitzii influence the production of mucus glycans and the development of globlet cells in the colonic epithelium of a gnotobiotic model rodent. BMC biology, 2013;11 (61):1-13. Published: May 21, 2013.
Wunderlich, P.F et al., Double-blind report on the efficacy of lactic acid-producing enterococcus SF68 in the prevention of antibiotic-associated diarrhoea and in the treatment of acute diarrhoea. The journal of international medical research. 1989; 17: 333-338.
Xie et al. Short communication: Modulation of the small intestinal microbial community composition over short-term or long-term administration with Lactobacillus plantarum ZDY2013. 2016. Journal Dairy Sci. 99:6913-6921. Epub Jun. 16, 2016.
Xu, et al., A genomic view of the human-Bacteroides thetaiotaomicron symbiosis. Science. Mar. 28, 2003; 299(5615):2074-6.
Xu, et al., The endogenous hydrogen sulfide producing enzyme cystathionine-i synthase contributes to visceral hypersensitivity in a rat model of irritable bowel syndrome. Molecular Pain, Biomed central, London, GB. Aug. 6, 2009; 5(1):p. 44.
Xu, J. et al., "Message from a human gut symbiont: sensitivity is a prerequisite for sharing", Trends in microbiology, 12(1), Jan. 1, 2004: pp. 21-28, XP055253932.
Yang, Changa et al., Non-invasive imaging of toll-like receptor 5 expressing using 131 labelled mAb in the mice bearing H22 tumors, Oncol. Lett. 2014., 7(6).1919-1924., Published online Apr. 2, 2014. DOI: 10.3892/ol.2014.2025.
Yao, W., et al., Cultivation-Independent Analysis of the Development of the Lactobacillus spp. Community in the Intestinal Tract of Newborn Piglets (2011)Agricultural Sciences in China, 10(3), pp. 438-447.
YQ et al. Therapeutic Modulation of the Gut Microbiota in IBD—More Questions to Be Answered. (2016). J. Dig. Dis., Oct. 15, 1751-2980, 12422, First published:Oct. 15, 2016.
Yu, Dah-Shyong et al., Bacille Calmette-Guerin can induce cellular apoptosis of urothelial cancer directly through toll-like receptor 7 activation, Kaohsiung Journal of Medical Sciences (2015) 31,391-397.
Yu, et al., Utilization of major fucosylated and sialylated human milk oligosaccharides by isolated human gut microbes. Glycobiology, 2013; 23(11):1281-1292. Epub Sep. 7, 2013.
Yu, N.Y., Wagner, J.R., Laird, M.R., Meili, G., Rey, S., Lo, R., et al. (2010a). PSORTb 3.0: improved protein subcellular localization prediction with refined localization subcategories and predictive capabilities for all prokaryotes. Bioinformatics 26(13), 1608-1615. doi: 10.1093/bioinformatics/btq249. Epub May 13, 2010.
Yun, J.H., et al., Isolation and characterization of potential pro biotic lactobacilli from pig feces (2009). Journal of Basic Microbiology, 49 (2), pp. 220-226.
Yurdusev, N. et al., Antagonistic Effect Exerted by Three Strictly Anaerobic Strains Against Various Strains of Clostridium Perfringens in Gnotobiotic Rodent Intestines. Can J Microbiol 33, 226-231 (1987).
Yurdusev, N. et al., InfectInunun 57,724-731 (1989).
Yutin, N. and Galperin, M.Y., A genomic update on clostridial phylogeny:Gram-negative spore formers and other misplaced Clostridia. Environmental microbiology. Oct. 2013; 15(10): 2631-2641. Epub Jul. 9, 2013.

(56) References Cited

OTHER PUBLICATIONS

Zhang, B. et al., Oral administration of enterococcus faecalis FK-23 suppresses Th17 cell development and attenuates allergic airway responses in mice. International journal of molecular medicine. 2012; 30:248-254. Epub May 24, 2012.
Zhang, B. et al., The Prevalence of Th17 Cells in Patients With Gastric Cancer. 2008. Biochem Biophys Res Commun 374 (3), 533-537. Epub Jul. 23, 2008.
Zhang, et al., The Activation of NF-κB in Infiltrated Mononuclear Cells Negatively Correlates with Treg Cell Frequency in Oral Lichen Planus. Inflammation. Aug. 2015;38(4):1683-9. doi: 10.1007/s10753-015-0145-x.
Zheng, B. et al., Bifidobacteriu breve attenuates murine dextran sodium sulfate-induced colitis and increases regulatory T cell responses. PLOS one. May 2014; 9(5). May 2, 2014.
Zheng, B., van Bergenhenegouwen, J., Overbeek, S., van de Kant, H.J., Garssen, J., Folkerts, G., et al. (2014). Bifidobacterium breve attenuates murine dextran sodium sulfate-induced colitis and increases regulatory T cell responses. PLoS One 9(5), e95441. doi: 10.1371/journal.pone.0095441. May 2, 2014.
Zheng, Bin et al., Bifodobacterium breve Attenuates Murine Dexran Doium Sulfate-Induced Colitis and Increases Regulatory T Cell Responses, PLOS ONE, vol. 9, Isue 5, e95441, May 2014. May 2, 2014.
Zhongyuan, T. et al., The inflammation regulation effects of enterococcus faecium HDRsEfl on human enterocyte-like HT-29 cells. Animal cells and systems. Mar. 2016;20(2):70-76. Mar. 22, 2016.
Zhou et al. Central and peripheral hypersensitivity in the irritable bowel syndrome. 2010. Pain. 148(3): 454-461. Epub Jan. 13, 2010.
Zhu, S. and Qian, Y., IL-17/IL-17 receptor system in autoimmune disease: mechanisms and therapeutic potential. Clinical Science (2012) 122, 487-511.
Zitomersky, N. et al., Characterization of Adherent Bacteroidales from Intestinal Biopsies of Children and Young Adults with Inflammatory Bowel Disease. PLOS one. 2013; 8(6). e63686. Published online Jun. 11, 2013.
Zitvogel, et al., Type I interferons in anticancer immunity. Nature Reviews. Jul. 2015:405-414. Epub Jun. 1, 2015.
Carbonnelle, Etienne et al., "MALDI-TOF mass spectrometry tools for bacterial identification in clinical microbiology laboratory", Clinical Biochemistry 44 (2011) 104-109. Epub Jul. 8, 2010.

Paul P. Tak and Gary S. Firestein, "NF-κB: a key role in inflammatory diseases", The Journal of Clinical Investigation, Jan. 2001, vol. 107, No. 1, pp. 1-7.
Amadi-Obi, Ahjoku et al., "TH17 cells contribute to uveitis and scleritis and are expanded by IL-2 and inhibited by IL-27/STAT1", Nature Medicine, 2007, vol. 13, No. 6, 711-718.
Analytical Profile index, 2019, https://en.wikipedia.org/wiki/Analytical_profile_index.
Cryan, John F. and Dinan, Timothy G, "Mind-Altering Microorganisms: The Impact Of The Gut Microbiota On Brain And Behavior", Nature Reviews, Neuroscience, vol. 13, Oct. 2012, 701-712.
Drancourt, Michel et al., "16S Ribosomal DNA Sequence Analysis of a Large Collection of Environmental and Clinical Unidentifiable Bacterial Isolates", Journal of Clinical Microbiology, Oct. 2000, 3623-3630.
Guarner, F. et al., World Gastroenterology Organisation Global Guidelines, "Probiotics and prebiotics", Feb. 2017, pp. 1-35.
Harty, D.W.S. et al., "Pathogenic potential of lactobacilli", International Journal of Food Microbiology 24, 1994, 179-189.
Helena S. Domingues et al.," Functional and Pathogenic Differences of Th1 and Th17 Cells in Experimental Autoimmune Encephalomyelitis", PLoS ONE, Nov. 2010, vol. 5, Issue 11, e15531, pp. 1-13, Published online Nov. 29, 2010.
Justesen, Ulrik Stenz et al., "16S rRNA Gene Sequencing in Routine Identification of Anaerobic Bacteria Isolated from Blood Cultures", Journal of Clinical Microbiology, vol. 48,No. 3, Mar. 2010, p. 946-948, 0095-1137/10/$12.00 doi:10.1128/JCM.02075-09, Epub Jan. 13, 2010.
Kabashima, K., "The Critical Role of Th17 Cells in the Pathogenesis of Atopic Dermatitis", J Environ Dermatol Cutan Allergol., 2009, vol. 3 No.3, p. 129-137.
Nakamura, K. et al., "Special Edition/Pathology and Treatment of Atopic Dermatitis, Recent Findings on Cytokine Abnormalities in Atopic Dermatitis", MB Derma, 2011, vol. 175, pp. 15-19.
Ross, M. et al., "16S gut community of the Cameron County Hispanic Cohort", Microbiome, 2015, vol. 3, No. 7, pp. 1-11.
Spergel, J. et al., "Atopic dermatitis and the atopic march", J Allergy Clin Immunol, Dec. 2003, vol. 112, No. 6, pp. S118-S127.
Nomura, T. et al., "The panoply of αβT cells in the skin", Journal of Dermatological Science, 2014, vol. 76, pp. 3-9.

* cited by examiner

SEQUENCE LISTING

```
<160> NUMBER OF SEQ ID NOS: 4

<210> SEQ ID NO 1
<211> LENGTH: 15
<212> TYPE: PRT
<213> ORGANISM: Roseburia hominis

<400> SEQUENCE: 1

Ala Gln Tyr Asn Asp Asp Ala Lys Ser Val Leu Glu Ile Leu Lys
1               5                   10                  15

<210> SEQ ID NO 2
<211> LENGTH: 14
<212> TYPE: PRT
<213> ORGANISM: Roseburia hominis

<400> SEQUENCE: 2

Gly Leu Asn Lys Ala Ser Arg Asn Ser Gln Asp Gly Ile Ser
1               5                   10

<210> SEQ ID NO 3
<211> LENGTH: 18
<212> TYPE: DNA
<213> ORGANISM: Artificial Sequence
<220> FEATURE:
<223> OTHER INFORMATION: Description of Artificial Sequence: Synthetic
      General bacterial probe Eub338

<400> SEQUENCE: 3
gctgcctccc gtaggagt                                              18

<210> SEQ ID NO 4
<211> LENGTH: 23
<212> TYPE: DNA
<213> ORGANISM: Artificial Sequence
<220> FEATURE:
<223> OTHER INFORMATION: Description of Artificial Sequence: Synthetic
      Roseburia hominis A2-183-specific probe

<400> SEQUENCE: 4
gtacattaca tactctgtca gtg                                        23
```

BACTERIUM FOR USE AS A PROBIOTIC FOR NUTRITIONAL AND MEDICAL APPLICATIONS

CROSS REFERENCE

This application is a divisional of U.S. application Ser. No. 15/070,605, filed Mar. 15, 2016, now U.S. Pat. No. 9,937,211, issued Apr. 10, 2018, which is a continuation of U.S. application Ser. No. 14/349,907, filed Apr. 4, 2014, now U.S. Pat. No. 9,314,489, issued Apr. 19, 2016, which is a 371 of International Application No. PCT/GB2012/052495 filed Oct. 8, 2012, which claims priority to GB application number 1117313.5, filed Oct. 7, 2011, each of which are herein incorporated by reference in their entirety.

SEQUENCE LISTING

The instant application contains a Sequence Listing which has been submitted in ASCII format via EFS-Web and is hereby incorporated by reference in its entirety. Said ASCII copy, created on Jul. 2, 2021 is named "56708_703_401_SL.txt" and is 1,328 bytes in size.

BACKGROUND TO THE INVENTION

The present invention relates to the bacterial species *Roseburia hominis* and various nutritional and therapeutic uses thereof.

The human intestine, thought to be initially sterile in utero, is exposed to a large variety of maternal and environmental microbes immediately after birth. The subsequent colonization and succession events in the gut remain dynamic during the first years of life, after which the microbiota becomes adult-like and relatively stable (1). The human gut microbiota contains more than 500 different phylotypes belonging essentially to two major bacterial divisions, the Bacteroidetes and the Firmicutes (2). The successful symbiotic relationships arising from bacterial colonization of the human gut have yielded a wide variety of metabolic, structural, protective and other beneficiary functions. The enhanced metabolic activities of the colonized gut ensure that dietary components, which are otherwise indigestible, are degraded with released byproducts providing an important nutrient source for the host. Similarly, the immunological importance of the gut microbiota is well-recognized and exemplified in germfree animals which have an impaired immune system that is functionally reconstituted following the introduction of commensal bacteria (3-5).

In sharp contrast to the production of secretory intestinal IgA which is influenced by microbial colonization per se (6, 7), T cell development and differentiation seems to require colonization of specific commensal micro-organisms. *Clostridium* species, in particular the spore-forming segmented filamentous bacteria (SFB), appear to be a major driver for the maturation of intestinal Th1, Th17 and Tregs (8, 9). Recent studies have, however, now shown that other gut bacteria including those of the altered Schaedler flora can induce de novo generation of Tregs while mono-colonization with *Bacteroides fragilis* can correct the Th1/Th2 imbalance in germfree mice by promoting the expansion of Tregs (5, 10).

The present invention seeks to elucidate other resident gut bacteria that can modulate metabolic activity in the gut and/or play a role in immunoregulatory processes.

STATEMENT OF INVENTION

The present invention centres on the activity of the bacterial species *Roseburia hominis*, a member of the Firmicutes phylum. Studies by the applicant have demonstrated that this bacterial species plays an important part in immunoregulation and metabolic activity in the gut, as well as having an effect on appetite and satiety genes. The roles of bacterial genes participating in colonization and adaptation to the murine gut, as well as the host genes responding to colonization by this bacterium are described in more detail below.

Aspects of the invention, together with preferred embodiments, are set forth in the accompanying claims.

A first aspect of the invention relates to the bacterial species *Roseburia hominis* for use in regulating the immune system of a subject.

Another aspect of the invention relates to the bacterial species *Roseburia hominis* for use in treating a disorder selected from an inflammatory disorder, an immune disorder and an intestinal disorder.

Another aspect of the invention relates to the bacterial species *Roseburia hominis* for use in promoting gut health by restoring immune homeostasis.

Another aspect of the invention relates to the bacterial species *Roseburia hominis* for use in improving intestinal microbiota in a subject.

Another aspect of the invention relates to the bacterial species *Roseburia hominis* for use in regulating the innate immune system of a subject.

Another aspect of the invention relates to the bacterial species *Roseburia hominis* for use in regulating the adaptive immune system of a subject.

Another aspect of the invention relates to the bacterial species *Roseburia hominis* for use in promoting Tregs and immune tolerance of a subject.

Another aspect of the invention relates to the bacterial species *Roseburia hominis* for use in regulating appetite in a subject.

Another aspect of the invention relates to the use of the bacterial species *Roseburia hominis* in the preparation of a medicament for regulating the immune system of a subject.

Another aspect of the invention relates to the use of the bacterial species *Roseburia hominis* in the preparation of a nutritional supplement or medicament for treating a disorder selected from an inflammatory disorder, an immune disorder and an intestinal disorder in a subject.

Another aspect of the invention relates to the use of the bacterial species *Roseburia hominis* in the preparation of a nutritional supplement or medicament for improving intestinal microbiota in a subject.

Another aspect of the invention relates to the use of the bacterial species *Roseburia hominis* in the preparation of a nutritional supplement or medicament for regulating the innate immune system of a subject.

Another aspect of the invention relates to the use of the bacterial species *Roseburia hominis* in the preparation of a nutritional supplement or medicament for regulating the adaptive immune system of a subject.

Another aspect of the invention relates to the use of the bacterial species *Roseburia hominis* in the preparation of a nutritional supplement or medicament for regulating appetite in a subject.

Another aspect of the invention relates to a method of treating a disorder selected from an inflammatory disorder, an immune disorder and an intestinal disorder in a subject, said method comprising administering to the subject a nutritionally or pharmaceutically effective amount of the bacterial species *Roseburia hominis*.

Another aspect of the invention relates to a method of improving intestinal microbiota in a subject, said method comprising administering to the subject a composition comprising the bacterial species *Roseburia hominis*.

Another aspect of the invention relates to method of regulating the innate immune system of a subject, said method comprising administering to the subject a composition comprising the bacterial species *Roseburia hominis*.

Another aspect of the invention relates to a method of regulating the adaptive immune system of a subject, said method comprising administering to the subject a composition comprising the bacterial species *Roseburia hominis*.

Another aspect of the invention relates to a method of regulating appetite in a subject, said method comprising administering to the subject a composition comprising the bacterial species *Roseburia hominis*.

Another aspect of the invention relates to the bacterial species *Roseburia hominis* for use in medicine.

Another aspect of the invention relates to a pharmaceutical composition comprising the bacterial species *Roseburia hominis* and a pharmaceutically acceptable excipient, carrier or diluent.

Another aspect of the invention relates to a nutritional supplement comprising the bacterial species *Roseburia hominis* and a nutritionally acceptable excipient, carrier or diluent.

Another aspect of the invention relates to a probiotic composition comprising the bacterial species *Roseburia hominis*.

Another aspect of the invention relates to a feedstuff, food product, nutritional supplement, dietary supplement or food additive comprising the bacterial species *Roseburia hominis*.

Another aspect of the invention relates to a process for producing a pharmaceutical composition according to the invention, said process comprising admixing the bacterial species *Roseburia hominis* with a pharmaceutically acceptable excipient, carrier or diluent.

Another aspect of the invention relates to a process for producing a nutritional supplement according to the invention, said process comprising admixing the bacterial species *Roseburia hominis* with a nutritionally acceptable excipient, carrier or diluent.

Another aspect of the invention relates to the bacterial species *Roseburia hominis* for use in maintaining immune homeostasis in a subject.

DETAILED DESCRIPTION OF THE INVENTION

As mentioned above, one aspect of the invention relates to *Roseburia hominis* for use in one or more of:
  treating an immune disorder;
  treating an intestinal disorder;
  improving intestinal microbiota;
  regulating the innate immune system of a subject
  regulating the adaptive immune system of a subject;
  promoting Tregs and immune tolerance;
  regulating appetite in a subject;
  promoting gut health in a subject; and/or
  maintaining immune homeostasis in a subject.
*Roseburia hominis*

*Roseburia hominis*, a recently described commensal-gut anaerobe of the phylogenetic cluster XIVa within the Firmicutes phylum, belongs to a dominant group of bacteria in the human gut and is also a major butyrate producer (11). The present applicant has elucidated the complete genome sequence and annotation for this bacterium. Further studies investigated both bacterial and host transcriptome responses in germfree mice mono-colonized with *R. hominis*. The roles of bacterial genes participating in colonization and adaptation to the murine gut, as well as the host genes responding to colonization by this bacterium are described herein.

Experiments by the Applicant have shown that the activity of *Roseburia hominis* is highly specific. Studies have shown that important genomes of *Roseburia* species are very different, indicating diverse functionality. Indeed, experiments have shown that bacteria from *Clostridium* Cluster XIVa, including the bacterial species *Roseburia intestinalis*, *Roseburia hominis* and *Eubacterium rectale* (all of which are butyrate producers) surprisingly induce very different and distinct effects on gut cells.

In one preferred embodiment, the bacterial species is the strain deposited under the terms of the Budapest Treaty at National Collections of Industrial, Food and Marine Bacteria (NCIMB) at NCIMB Ltd, Ferguson Building, Craibstone Estate, Bucksburn, Aberdeen, UK, AB21 9YA, on 21 Oct. 2004 on behalf of the Rowett Research Institute of Nutrition and Health, University of Aberdeen, Greenburn Road, Aberdeen, AB21 9SB, Scotland, UK, under the accession number NCIMB 14029T *Roseburia hominis* A2-183T (DSM=16839T). All microorganism deposits were made under the terms of the Budapest Treaty and thus viability of the deposit is assured. Maintenance of a viable culture is assured for 30 years from the date of deposit. During the pendency of the application, access to the deposit will be afforded to one determined by the Commissioner of the United States Patent and Trademark Office to be entitled thereto. All restrictions on the availability to the public of the deposited microorganisms will be irrevocably removed upon the granting of a patent for this application. The deposit will be maintained for a term of at least thirty (30) years from the date of the deposit or for the enforceable life of the patent or for a period of at least five (5) years after the most recent request for the furnishing of a sample of the deposited material, whichever is longest. The deposit will be replaced should it become necessary due to inviability, contamination or loss of capability to function in the manner described in the specification.

The bacterial species is preferably *Roseburia hominis* as described in Duncan, S. H., Aminov, R. I., Scott, K. P., Louis, P., Stanton, T. B., & Flint, H. J. (2006) *Int. J. Syst. Evol. Microbial.* 56: 2437-2441.

In one preferred embodiment, the bacterial species is in the form of a live bacterial population, a lyophilized bacterial population, a non-viable bacterial preparation, or the cellular components thereof. Preferably, where the bacterial species is in the form of a non-viable bacterial preparation, it is selected from heat-killed bacteria, irradiated bacteria and lysed bacteria.

In one preferred embodiment, the bacterial species is in the form of live bacteria or the cellular components thereof.

In one preferred embodiment, the bacterial species is in isolated form. As used herein, the term "isolated" means isolated from its native environment.

In one preferred embodiment, the bacterial species is in biologically pure form. As used herein the term "biologically pure" refers to a laboratory culture that is substantially free from other species of organism. Preferably, the bacterial species is in the form of a culture of a single species of organism.

The invention also encompasses the use of mutants of the bacterial species or strains described herein. As used herein, the term "mutant" includes derived bacterial strains having at least 93% homology, preferably at least 96% homology, more preferably 98% homology to the polynucleotide sequence of a referenced strain, but otherwise comprising mutations in other sequences in the bacterial genome. Mutants are obtainable by genetic engineering techniques inferring alteration of the genetic material of the strains of the invention or inferring a recombination of the genetic material of the strains of the invention with other molecules. Typically, in order to obtain such mutant strains, a person skilled in the art can use standard mutagenesis techniques such as UV radiation or exposure to mutagenic chemical products.

As used herein, the term "mutations" includes natural or induced mutations comprising at least single base alterations including deletions, insertions, transversions, and other modifications known to those skilled in the art, including genetic modification introduced into a parent nucleotide or amino acid sequence whilst maintaining at least 50% homology to the parent sequence. Preferably, the sequence comprising the mutation or mutations has at least 60%, more preferably at least 75%, more preferably still 85% homology with the parental sequence. As used herein, sequence "homology" can be determined using standard techniques known to those skilled in the art. For example, homology may be determined using the on-line homology algorithm "BLAST" program.

The invention also encompasses the use of homologues of the bacterial species or strains described herein. As used herein the term "homologue" refers to a bacterial strain having a nucleotide sequence having a degree of sequence identity or sequence homology with the nucleotide sequence of the parent bacterial strain (hereinafter referred to as a "homologous sequence(s)"). Here, the term "homologous" means an entity having a certain homology with the subject nucleotide sequence. Here, the term "homology" can be equated with "identity".

In the present context, a homologous sequence is taken to include a nucleotide sequence which may be at least 50, 60, 70, 75, 80, 85 or 90% identical, preferably at least 95%, 97%, 98% or 99% identical to the nucleotide sequence of the parent bacterial strain (the subject sequence).

Homology comparisons can be conducted by eye, or more usually, with the aid of readily available sequence comparison programs. These commercially available computer programs can calculate % homology between two or more sequences.

% homology may be calculated over contiguous sequences, i.e. one sequence is aligned with the other sequence and each amino acid in one sequence is directly compared with the corresponding amino acid in the other sequence, one residue at a time. This is called an "ungapped" alignment. Typically, such ungapped alignments are performed only over a relatively short number of residues.

Although this is a very simple and consistent method, it fails to take into consideration that, for example, in an otherwise identical pair of sequences, one insertion or deletion will cause the following amino acid residues to be put out of alignment, thus potentially resulting in a large reduction in % homology when a global alignment is performed.

Calculation of maximum % homology therefore firstly requires the production of an optimal alignment, taking into consideration gap penalties. A suitable computer program for carrying out such an alignment is the Vector NTI (Invitrogen Corp.). Examples of software that can perform sequence comparisons include, but are not limited to, the BLAST package (see Ausubel et al 1999 Short Protocols in Molecular Biology, 4th Ed—Chapter 18), BLAST 2 (see FEMS Microbial Lett 1999 17 4(2): 24 7-50; FEMS Microbial Lett 1999 177(1): 187-8), FASTA (Altschul et al 1990 J. Mol. Biol. 403-410) and AlignX for example. At least BLAST, BLAST 2 and FASTA are available for offline and online searching (see Ausubel et al 1999, pages 7-58 to 7-60). Preferably, the degree of identity with regard to a nucleotide sequence is determined over at least 20 contiguous nucleotides, preferably over at least 30 contiguous nucleotides, preferably over at least 40 contiguous nucleotides, preferably over at least 50 contiguous nucleotides, preferably over at least 60 contiguous nucleotides, preferably over at least 100 contiguous nucleotides. Preferably, the degree of identity with regard to a nucleotide sequence may be determined over the whole sequence.

The traditional identification of bacteria on the basis of phenotypic characteristics is generally not as accurate as identification based on genotypic methods. Comparison of the bacterial 16S rRNA gene sequence has emerged as a preferred genetic technique and allows for new strains to be identified by comparison of sequences with known bacterial DNA sequences using BLAST. The 16S rRNA gene sequence is universal in bacteria, and so relationships can be measured across many different bacteria. In general, the comparison of the 16S rRNA sequence allows differentiation between organisms at the genus level across all major phyla of bacteria, in addition to classifying strains at multiple levels, including species and sub-species level. The 16S rRNA gene sequence has been determined for a large number of strains. GenBank, the largest databank of nucleotide sequences, has over 20 million deposited sequences, of which over 90,000 are of 16S rRNA genes. This means that many previously deposited sequences exist against which the sequence of an unknown strain can be compared.

As used herein the term "16S rRNA identity" refers to the percentage identity with a known bacterial strain. In one preferred embodiment, the bacterial strain has a 16S rRNA identity of at least 99.5% with the strain deposited under the above accession number.

The invention also encompasses mutant strains, which can be obtained from the above-mentioned deposited strain, and strains exhibiting a DNA-DNA homology of at least 70% and/or a 16S RNA identity of at least 99.5% with the strain deposited under the above accession number.

In the context of the present invention, the term "DNA-DNA homology" refers to how closely related two or more separate strands of DNA are to each other, based on their nucleotide sequence. Typically, this is measured in terms of their % identity. In one preferred embodiment, the bacterial strain has a DNA-DNA homology of at least 70% with the strain deposited under the above accession number.

In one highly preferred embodiment, the bacterial strain has a DNA-DNA homology of at least 70% and a 16S rRNA identity of at least 99.5% with the strain deposited under the above accession number.

Therapeutic Applications

Another aspect of the invention relates to the bacterial species *R. hominis* for use in medicine.

More particularly, the bacterial species *Roseburia hominis* is for use in treating a disorder selected from an inflammatory disorder, an immune disorder and an intestinal disorder in a subject.

As used herein, the term "medicament" encompasses medicaments for both human and animal usage in human and veterinary medicine. In addition, the term "medicament" as used herein means any substance, which provides a therapeutic and/or beneficial effect. The term "medicament" as used herein is not necessarily limited to substances, which need Marketing Approval, but may include substances which, can be used in cosmetics, nutraceuticals, food (including feeds and beverages for example), probiotic cultures, nutritional supplements and natural remedies. In addition, the term "medicament" as used herein encompasses a product designed for incorporation in animal feed, for example livestock feed and/or pet food.

In one preferred embodiment of the invention, the disorder is selected from irritable bowel syndrome (IBS), colitis, inflammatory bowel disorder (IBD), including Crohn's disease and ulcerative colitis, pouchitis, functional dyspepsia, functional constipation, functional diarrhoea (including antibiotic associated diarrhoea, traveller's diarrhoea and pediatric diarrhoea), functional abdominal pain, functional bloating, Epigastric Pain Syndrome, Postprandial Distress Syndrome, gastrointestinal reflux disease (GERD), autoimmune diseases such as diabetes, arthritis, multiple sclerosis and psoriasis allergies, atopic diseases e.g. atopic dermatitis, necrotising enterocolitis, other infections, and combinations thereof.

In one particularly preferred embodiment, the disorder is an inflammatory disorder. Preferably, the expression of pro-inflammatory genes is downregulated in the host subject. Further details of these studies are presented below.

More preferably, the inflammatory disorder is colitis, even more preferably, Crohn's disease, ulcerative colitis or pouchitis.

In one particularly preferred embodiment, the intestinal disorder is IBS. The precise pathophysiology of IBS remains to be elucidated. Recent studies have described mucosal inflammation and alterations in intestinal microbiota in IBS patients and a disease correlation with intestinal infections.

In one particularly preferred embodiment, the intestinal disorder is IBD. Preferably, the expression of barrier genes is enhanced in the host subject. Further details of these studies are presented below.

In one particularly preferred embodiment, the intestinal disorder is Crohn's disease.

In one particularly preferred embodiment, the disorder is an immune disorder. Preferably, the immune disorder is selected from ulcerative colitis, pouchitis, other autoimmune conditions including rheumatoid arthritis, psoriasis, multiple sclerosis, allergies, including coeliac disease, atopic dermatitis and rhinitis.

In one embodiment, the bacterial species *Roseburia hominis* is for use in regulating the immune system of a subject. Immune regulation by bacterial species is known to be highly species-specific (8). In particular, the immune regulatory effect of Cluster XIVa and VI bacteria is very complicated, and independent of butyrate production (41).

In one preferred embodiment, the innate immune system of the subject is modulated.

In another preferred embodiment, the adaptive immune system of the subject is modulated towards immune regulation (and not immune activation, therefore reducing inflammation).

Another aspect of the invention relates to the bacterial species *Roseburia hominis* for improving intestinal microbiota in a subject.

Intestinal microbiota refers to microorganisms that live in the digestive tract of the host animals. These microorganisms perform a wide variety of metabolic, structural, protective and other beneficiary functions. As used herein, "improving intestinal microbiota" refers to increasing the number and/or or type of microorganisms present in the intestine of a host, and/or increasing the activity of said microorganisms in terms of their metabolic, structural, protective and other beneficiary functions.

Preferably, *Roseburia hominis* colonizes the colon and/or the ileum, more preferably the colon.

In one preferred embodiment, *Roseburia hominis* regulates the expression of at least one mobilization or chemotaxis gene.

More preferably, *Roseburia hominis* upregulates the expression of at least one mobilization or chemotaxis gene. More preferably still, the mobilization or chemotaxis gene is selected from MobA and MobL.

In another preferred embodiment, *Roseburia hominis* regulates the expression of at least one gene selected from FlaA1, FlaA2, Fla3 and FlaB.

Specific serum antibodies to FLA type proteins are present in inflammatory bowel disease. Thus, in one preferred embodiment, the *Roseburia hominis* is for use in treating inflammatory bowel disease.

In another preferred embodiment, *Roseburia hominis* regulates the expression of one or more of the following: acetyl-CoA acetyltransferase, 3-hydroxyacyl-CoA dehydrogenase, butyryl-CoA dehydrogenase, electron transfer flavoprotein beta subunit, and electron transfer flavoprotein alpha subunit.

Another aspect of the invention relates to the bacterial species *Roseburia hominis* for regulating the innate immune system of a subject.

As used herein, the term "innate immune system", also known as the non-specific immune system, comprises the cells and mechanisms that provide the host with immediate defense against infection by other organisms in a nonspecific manner. This means that the cells of the innate system recognize and respond to pathogens in a generic way, but unlike the adaptive immune system, it does not confer long-lasting or protective immunity to the host.

As used herein, the term "regulating the innate immune system" means inducing the activity of the innate immune system, and/or increasing the level of activity relative to the baseline level of activity such that it promotes immune homeostasis.

Loss or dysregulation of the innate immune function, either due to loss of epithelial barrier, innate immune peptides such as defensins, chemokines and cytokines or defective TLR signalling are associated with increased risk of inflammatory diseases, in several body organs including the gut. Such diseases include inflammatory bowel disease. Thus, in one highly preferred embodiment, the *Roseburia hominis* is for use in treating inflammatory bowel disease.

In one preferred embodiment, the *Roseburia hominis* regulates the expression of at least one gene selected from Tlr5, Tir1 Vnn1, Defb37, Pla2g, Muc16, Itln, Sprr1a, Cldn4, Pmp22, Crb3, Magi3, Marveld3, Mpp7, Defcr20, Pcgf2, Ltbp4, Igsf8 and Tcfe2a. Many of theses genes are gut barrier genes and antimicrobials and hence work to reduce invasiveness of gut pathogens and also reduce the numbers of viable pathogens.

Another aspect of the invention relates to the bacterial species *Roseburia hominis* for regulating the adaptive immune system of a subject.

As used herein, the term "adaptive immune system", otherwise known as the "specific immune system" refers to highly specialized, systemic cells and processes that eliminate or prevent pathogenic growth. The adaptive immune response provides the vertebrate immune system with the ability to recognize and remember specific pathogens (to generate immunity), and to mount stronger attacks each time the pathogen is encountered.

As used herein, the term "regulating the adaptive immune system" means inducing the activity of the adaptive immune system, and/or promoting immune homeostatic mechanisms by increasing the level of activity relative to the baseline level of activity. Preferably, the adaptive immune system is modulated towards immune regulation (and not immune activation therefore reducing inflammation).

Defects and disorders associated with the adaptive immune system, particularly related to the function of T cells, are associated with many inflammatory and autoimmune diseases. T cell responses associated with Th1, Th2 and Th17 are associated with atopic, inflammatory and autoimmune diseases. Therapies which improve or increase T regulatory (Tregs) cell populations are important in controlling diseases driven by excessive Th1, Th2 and Th17 cell responses.

In one preferred embodiment, *Roseburia hominis* activates at least one immune response gene in the colon or ileum.

In one preferred embodiment, *Roseburia hominis* regulates the adaptive immune system by modulating the expression of genes associated with T-cell regulation, more preferably in the colon. More preferably, *Roseburia hominis* induces Tregulatory cells (Tregs). An increase in Treg numbers will combat the effects of other effector T cells, such as Th1, Th17 and Th2 which drive inflammation, autoimmunity and allergic/atopic conditions. Hence this property of *R. hominis* can be exploited to address many diseases where Teff/Treg cell balance is lost, e.g. Crohn's and ulcerative colitis In one particularly preferred embodiment, *Roseburia hominis* upregulates the expression of at least one gene selected from Ly6g6c and Ly6g6e in the ascending colon. Depletion of Ly6g6c and Ly6g6e increases infection risk, both gut and respiratory tract and is associated with diseases such as neutropenia. Thus, in one preferred embodiment, the *Roseburia hominis* is for use in treating neutropenia.

Another aspect of the invention relates to the bacterial species *Roseburia hominis* for use in maintaining immune homeostasis in a subject. As used herein "maintaining immune homeostasis" refers to the self-regulation of the body's immune system to maintain oral tolerance or immune stability in response to changing conditions. Oral tolerance refers to the normal immune responses to food and commensal bacteria in a healthy gut. These are lost in coeliac disease and Inflammatory Bowel Diseases such as Crohn's disease and ulcerative colitis. Thus, in one particularly preferred embodiment, *Roseburia hominis* is for use in treating coeliac disease and Inflammatory Bowel Diseases such as Crohn's disease and ulcerative colitis.

Another aspect of the invention relates to the bacterial species *Roseburia hominis* for use in regulating appetite in a subject.

As used herein, "regulating appetite" refers to the ability to modulate (i.e. increase or decrease) the desire for a host to eat food. Preferably, *Roseburia hominis* exerts a stimulatory effect on host appetite by downregulating the expression of genes associated with the suppression of appetite. Preferably, *Roseburia hominis* downregulates the expression of at least one gene selected from Agt, Cartpt, Cck, Cxcl12 and Gcg. More preferably, *Roseburia hominis* downregulates, the expression of the satiety hormones Cck and Gcg.

The bacterial species according to the invention may also be used in prophylactic applications. In prophylactic applications, bacterial species or compositions according to the invention are administered to a patient susceptible to, or otherwise at risk of, a particular disease in an amount that is sufficient to at least partially reduce the risk of developing a disease. Such an amount is defined to be "a prophylactic effective dose". The precise amounts depend on a number of patient specific factors such as the patient's state of health and weight

BRIEF DESCRIPTION OF THE DRAWINGS

The present invention is further described by way of the following figures, wherein:

FIG. 10 shows the fold-induction of A20 for *E. rectale, R. hominis*, FLA of *E. rectale*, FLA1 of *R. hominis*, EAV9, FLA of SV1400 relative to controls.

R. HOMINIS PREFERENTIALLY COLONIZES THE COLON

Figure 1A:
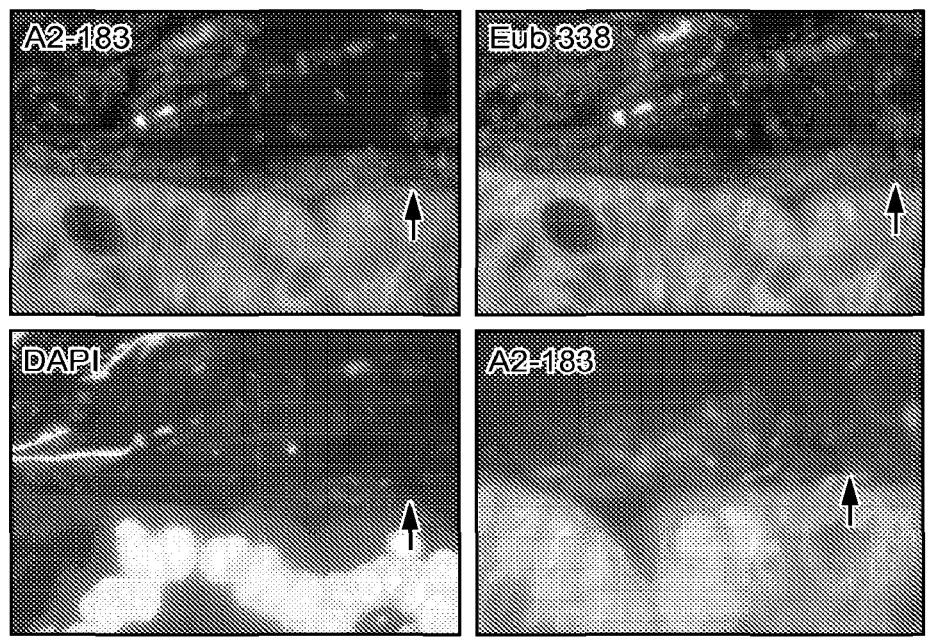
FIG. 1 shows the abundance and localization of *R. hominis* in ascending colon. (A) *R. hominis*-colonized mouse ascending colon showing close association of bacteria with the host epithelium, using the A2-183 FISH probe. Original magnification ×630. (B) PCR using *R. hominis*-specific primers showed a strong positive signal in faecal DNA post-colonization, while faeces of GF animals were negative for the presence of any bacteria. (C) Real-time PCR analysis showing colonization levels of *R. hominis*/mg faeces.
Figure 1B:
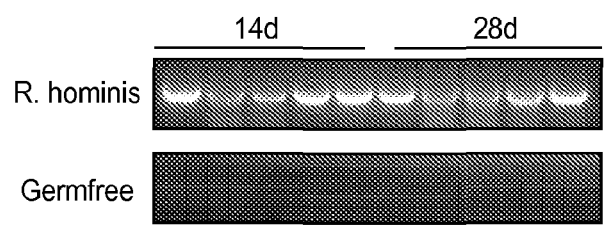
Figure 1C:
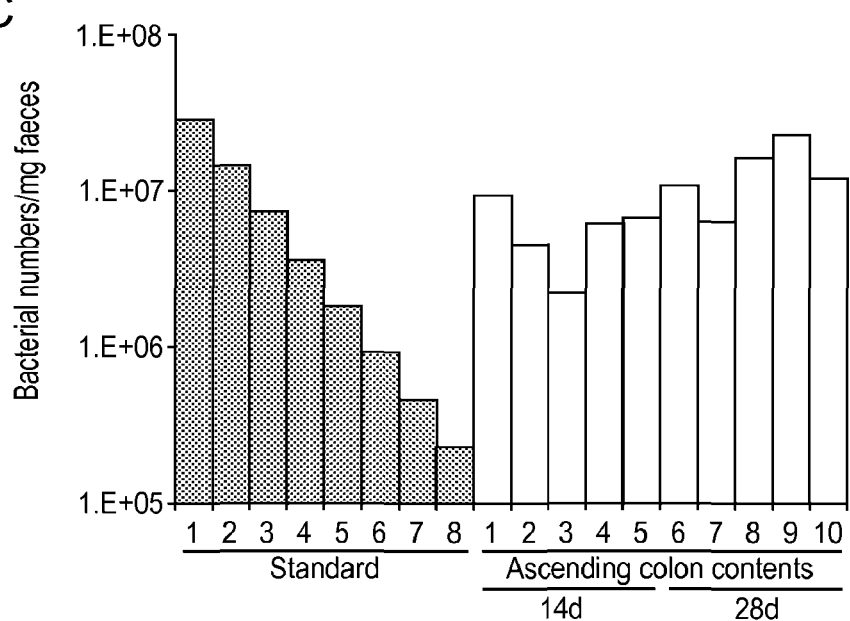
Figure 2A:
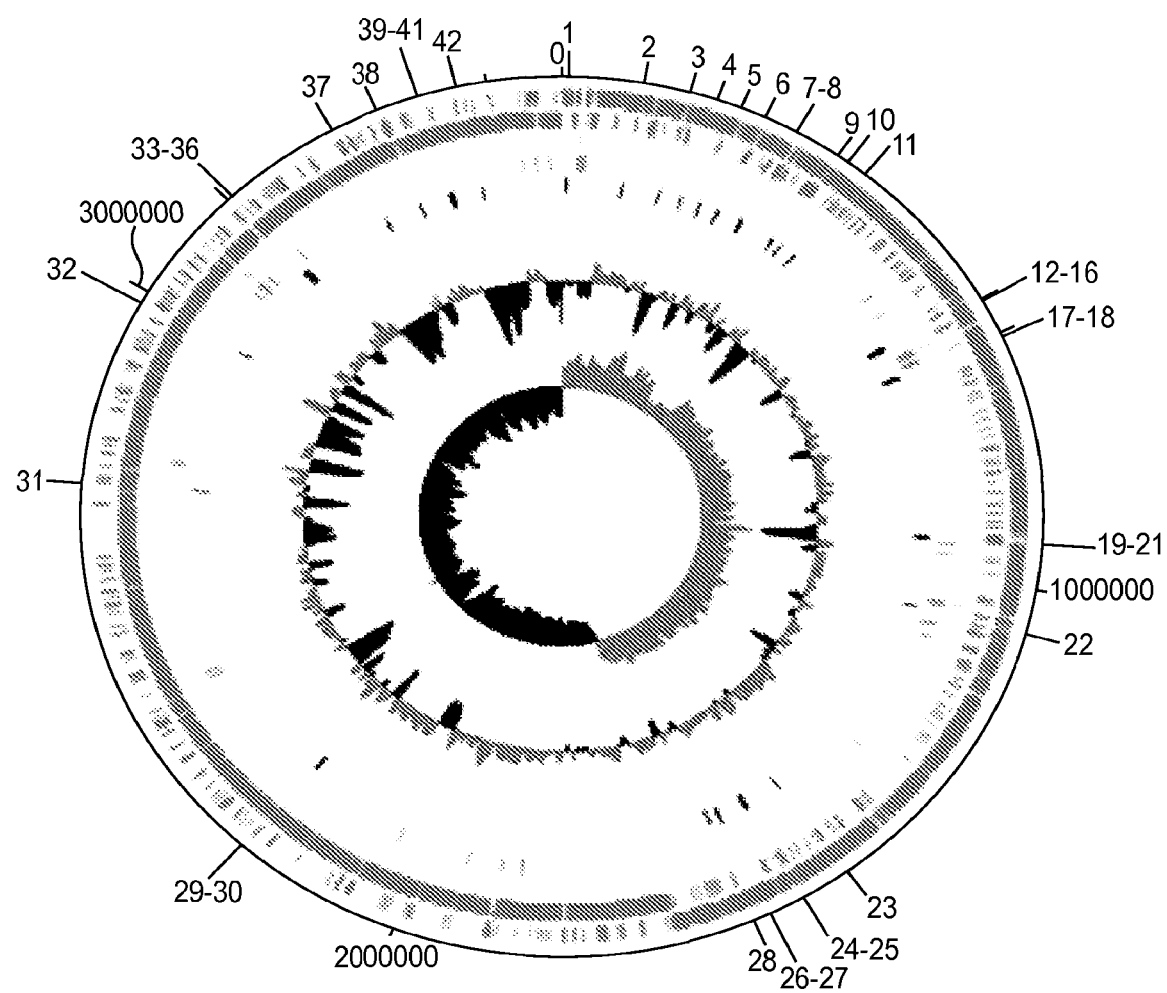
FIG. 2 shows the sequence and annotation of *R. hominis* genome. (A) *R. hominis* circular genome map with the location of the PCR experiments indicated in the regions targeted by the primers. The tracks on the genome map, starting at the outer track 0, are: track 0—(blue) Real-time PCR experiments indicated by numbered tick marks; track 1—(pale blue) Forward CDS; track 2—(pale blue) Reverse CDS; track 3—(blue) rRNA; track 4—(green) tRNA; track 5—(red) STS marking regions targeted by Real-time PCR; graph 1—GC content; graph 2—GC bias. (B) Functional annotation of the *R. hominis* genome.
Figure 2B:
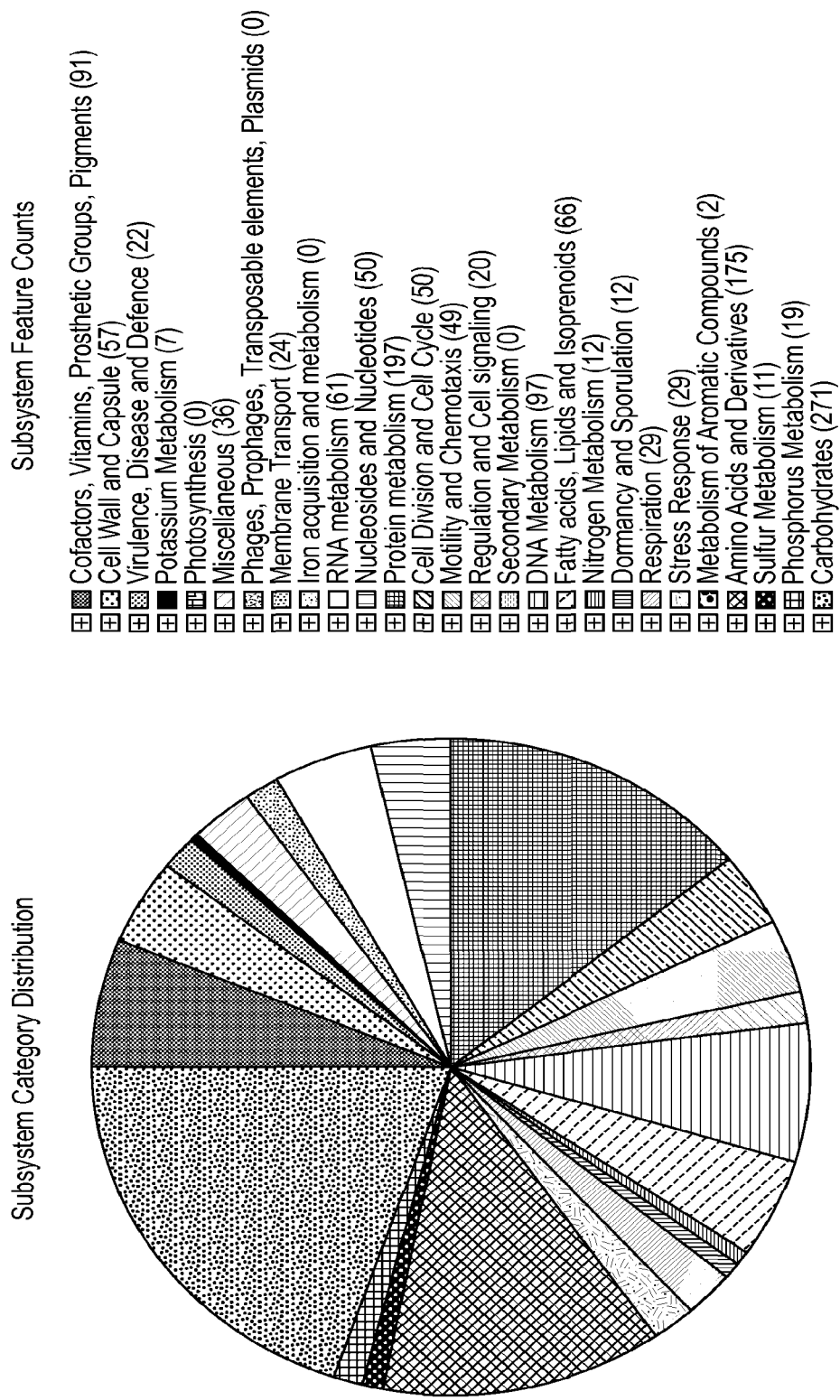

Healthy adult C3H/HeN germfree (GF) mice were inoculated with three gavages of *R. hominis* on consecutive days. Successful colonization was achieved using an inoculation medium containing 3% ascorbic acid and 2% cysteine to protect the bacterium from oxygen exposure. Analysis of gut tissue by fluorescent in situ hybridization (FISH) revealed that *R. hominis* colonized both the ileum and colon, but was found in much higher numbers in the colon. Bacteria were also found closely associated with the colonic mucosa (FIG. 1A). Colonization was further validated and quantified by PCR using *R. hominis*-specific primers with numbers approximating $1 \times 10^{10}$ bacteria/g faeces (FIGS. 1B and 1C). Faeces of GF animals tested negative for the presence of any bacteria. The *R. hominis* Genome Reveals Unique Genes Promoting Host Interactions The complete genome sequence of *R. hominis* A2-183 was elucidated (FIG. 2A, which is represented by a single 3,592,125-bp chromosome (FIG. 2B). Automated and manual annotation of the genome using the RAST platform revealed the presence of four ribosomal operons, 66 RNAs and 3,273 predicted proteins. The largest group of genes belonged to the Subsystem Category Carbohydrates (271 genes), encoding proteins involved in carbohydrate metabolism, followed by Protein Metabolism (197) and Amino acids and Derivatives (175) (FIG. 2B). Other important functional categories included Motility and Chemotaxis (49) and Dormancy and Sporulation (12). Comparative genomic analysis established that the closest relative in terms of genomic structure and function among the complete bacterial genomes is *Eubacterium rectale* (12), which is not surprising given the close taxonomical relatedness of these organisms (11, 13). Comparative reconstruction of these two genomes with 1,095 genes revealed that they differed by approximately 25% of the genes. In particular, these differences encompassed genes encoding important functions for interaction with the host. For example, the Motility and Chemotaxis genes encoding type IV fimbrial assembly proteins PilB and PilC were present in *E. rectale* but absent in *R. hominis* whereas flagellar basal-body rod protein FlgC, flagellar hook-basal body complex protein FliE, flagellin protein FlaB and flagellar motor switch protein FliG were unique to *R. hominis* The two bacterial genomes also differed by 42 carbohydrate genes, reflecting their divergent nutritional requirements. *R. hominis* Responds to the Gut Environment by Up-Regulating Mobilization and Chemotaxis Genes To determine the genes differentially expressed by *R. hominis* in response to association with the host and diet, a microarray was constructed using 6,000 PCR fragments from the small-insert-size sequencing library. Subsequent Realtime PCR validation was performed on 42 differentially expressed genes which cluster at specific regions of the *R. hominis* genome as illustrated in FIG. 2B. To distinguish between the effects of gut environment and dietary components, bacterial RNA was isolated from four different experimental conditions: (i) in vivo, from the caecum of mono-associated mice; (ii) in vitro, from bacteria grown in culture media; (iii) in vitro, from bacteria grown in the presence of dietary components; and (iv) from bacteria incubated on the surface of confluent Caco-2 and HT-29 cells.

Figure 3A:
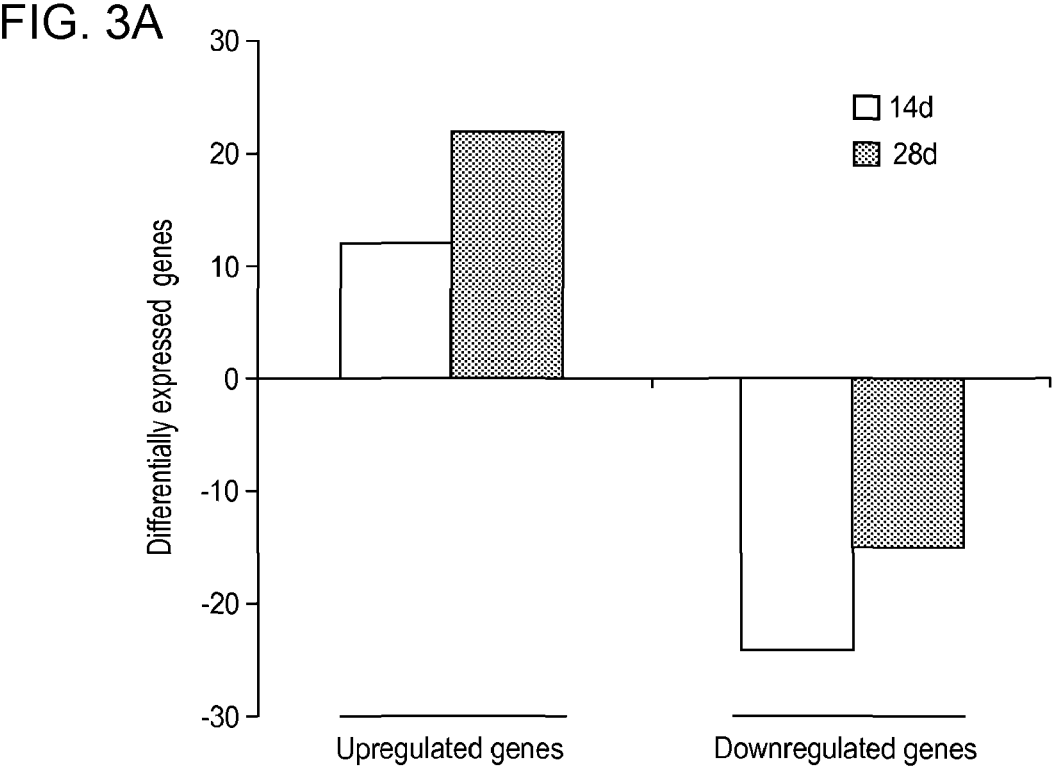
FIG. 3 identifies transcripts differentially expressed in *R. hominis* after colonization and adaptation to the murine gut. (A) Bacterial RNA was isolated from mouse caecum contents, labeled with either dCTP-Cy3 or dCTP-Cy5 during cDNA synthesis and hybridized to microarray slides incorporating a dye swap. Data was considered significant when fold change >2 and P<0.05. 50 differentially expressed genes (in vivo vs. in vitro) were uncovered by microarray analysis. (B) Real-time PCR validation of genes involved in conjugation/mobilization transfer. (C) Real-time PCR validation of genes involved in Motility and Chemotaxis. (D) Western blot of ascending gut contents immuno-stained with affinity-purified Fla2 antibody at 14d (lane 1: ladder, lanes 2-6: gut contents from animals 1-5, lanes 7-8: empty, lanes 9-10: *R. hominis* biomass (positive control)). Picture of *R. hominis* showing flagella (black arrows) and (E) Real-time PCR validation of genes involved in butyrate metabolism. (F) Realtime PCR analysis of *R. hominis* transcripts during in vitro exposure to human intestinal epithelial cells. Real-time PCR results are means of triplicates, *P<0.05, P<0.01, *p<0.001.
Figure 3B:
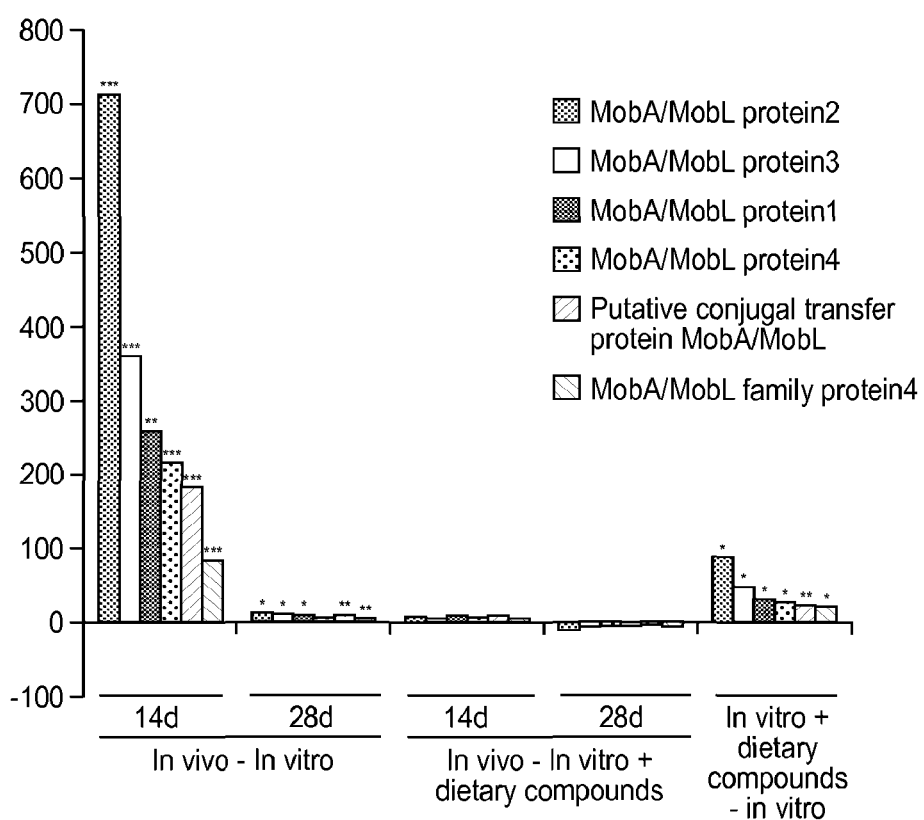

Fifty differentially expressed genes were identified (in vivo vs. in vitro) (FIG. 3A). The most surprising discovery was an extremely high up-regulation in vivo of genes involved in conjugation/mobilization transfer, the mobA- and mobL-like genes (FIG. 3B). The presence of such genes in the transcriptional studies was surprising as no identifiable genes were assigned to Phages, Prophages, Transposable Elements and Plasmids in the Subsystem Category feature. This difference in gene detection and allocation is likely due to the recognized limitations of the Subsystem Category annotation. The stimulatory effect of dietary compounds was much less pronounced, suggesting that the gut environment per se is a major inducer of genes involved in horizontal gene transfer.

Figure 3C:
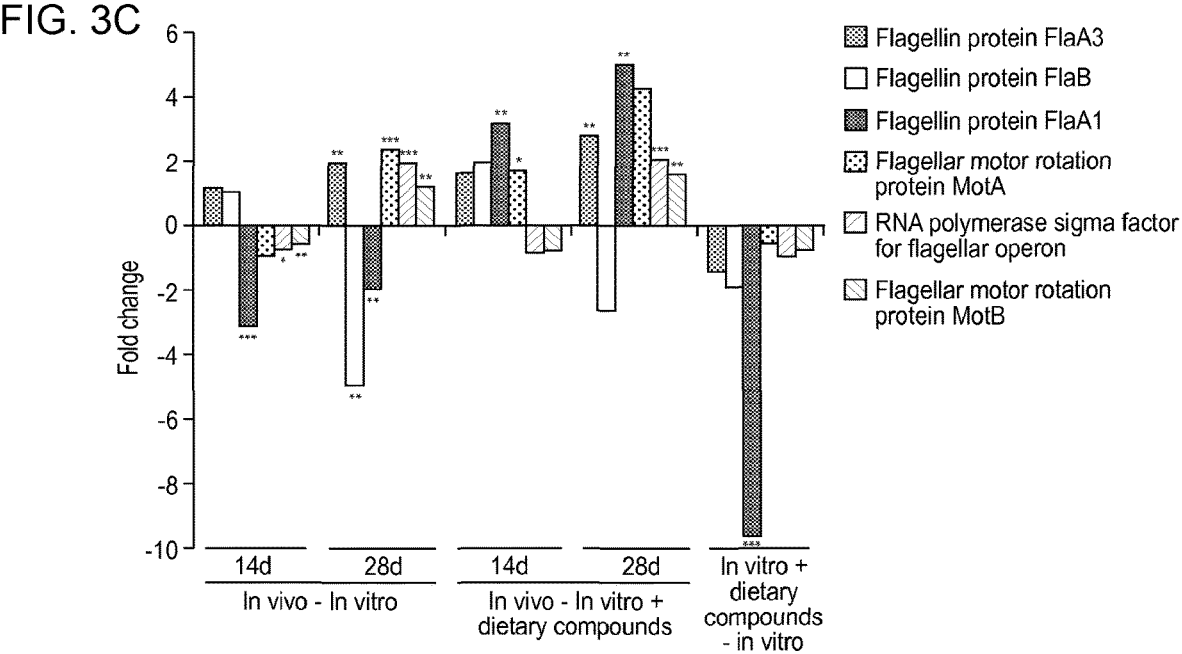
Figure 3D:
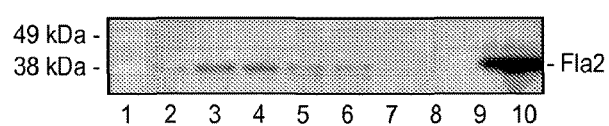
Figure 3D:
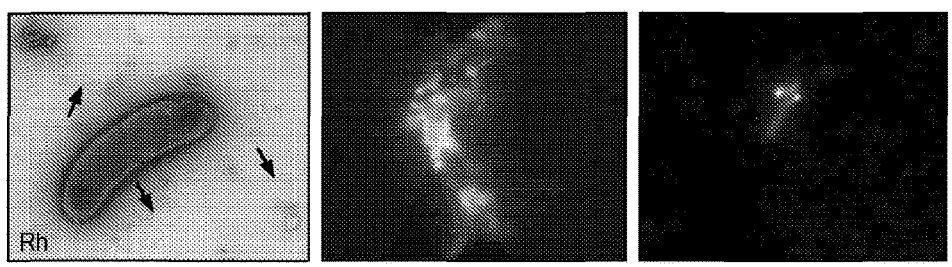

Other gut environment-induced subsystems included Membrane Transport, in particular magnesium transport, and Motility and Chemotaxis including multiple methyl-accepting chemotaxis proteins and genes of the flagellar operon (FIG. 3C). *R. hominis* possesses multiple flagellin genes flaA1, flaA2, flaA3, and flaB and interestingly growth in the mouse gut environment promoted flagellin expression in this bacterium as seen by western-blotting of bacteria isolated from in vivo colonized mice using *R. hominis*-specific flagellin antibodies (FIG. 3D). This is consistent with previous reports indicating that only certain subsets of Firmicutes produce flagella in vivo (14).

Figure 3E:
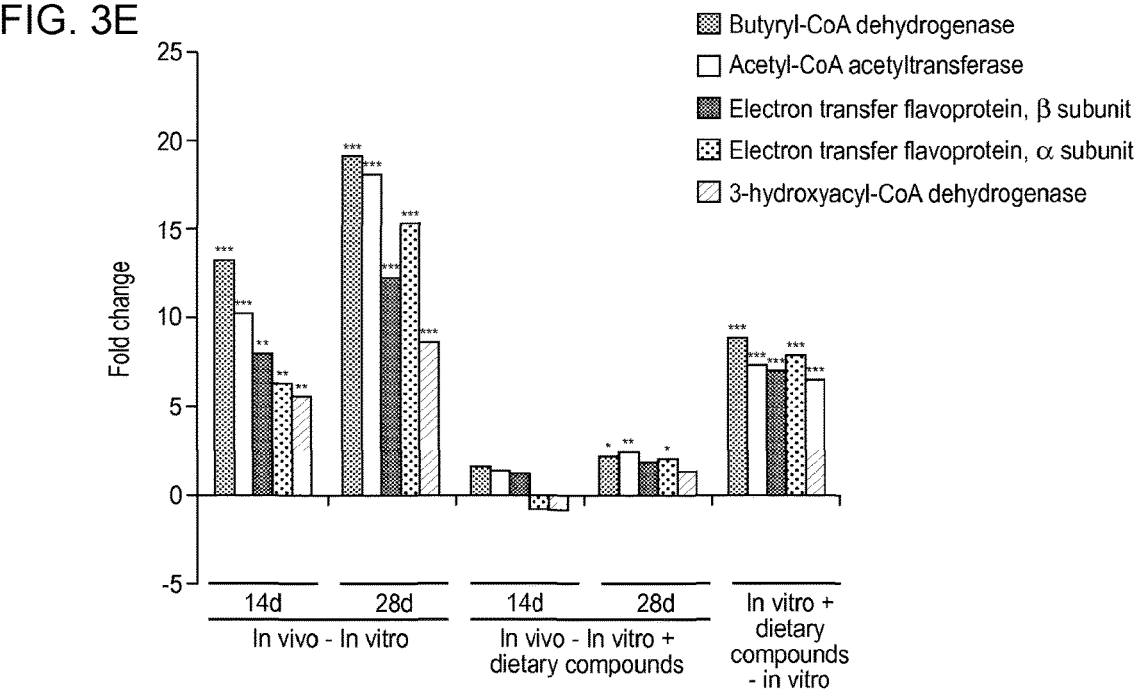

Not surprisingly, the expression of catabolic metabolism genes in *R. hominis* in the gut environment was mostly affected by dietary compounds (FIG. 3E). The genes involved included acetyl-CoA acetyltransferase, 3-hydroxyacyl-CoA dehydrogenase, butyryl-CoA dehydrogenase and phosphoenolpyruvate carboxykinase [ATP]. Although the regulation of these genes was mostly diet-driven, at the later sampling point the host effect was also apparent. Unexpectedly, the host environment down-regulated some genes participating in the metabolism of host-derived substances such as glucuronate, which is common in carbohydrate chains of mucosal proteoglycans.

Figure 3F:
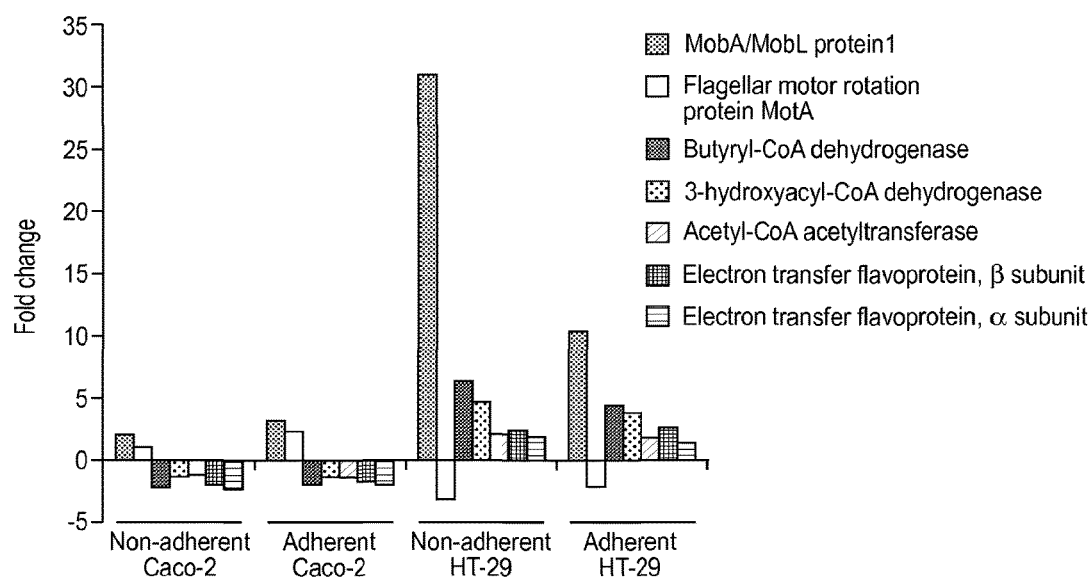
Figure 4A:
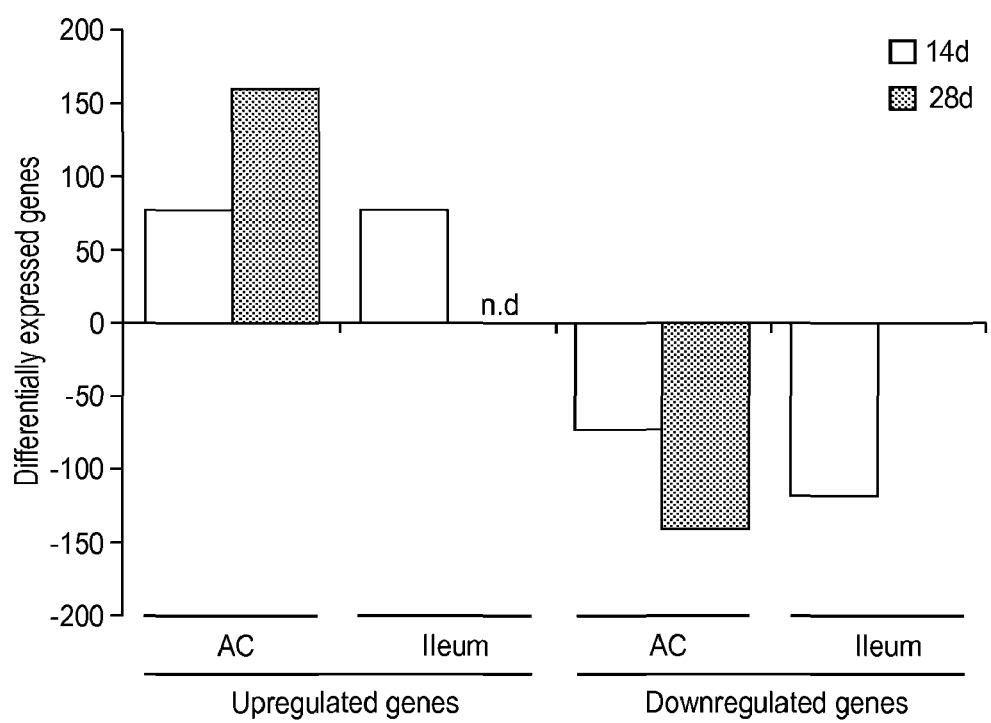
FIG. 4 identifies transcripts differentially expressed in the murine gut after mono-association with *R. hominis*. (A) Affymetrix microarray analysis of differentially expressed genes *R. hominis*-colonized mice relative to GF. Bar graphs represent number of genes higher and lower expressed after 14 and 28 days. (B) Heatmap generated from differentially expressed genes with functional significance-between GF and *R. hominis*-colonized mice at 14d and 28d. Columns represent individual arrays, and rows specific genes of interest. The Z-score depicts a measure of distance, in standard deviations, away from the mean. The relative value for each gene is depicted by colour intensity, with green indicating higher expression and red depicting lower expression. (C) Real-time PCR validation of genes shown to be significantly different between *R. hominis*-colonized and GF mice. Realtime PCR results are means of triplicates, *p<0.05, P<0.01, *P<0.001.
Figure 4B:
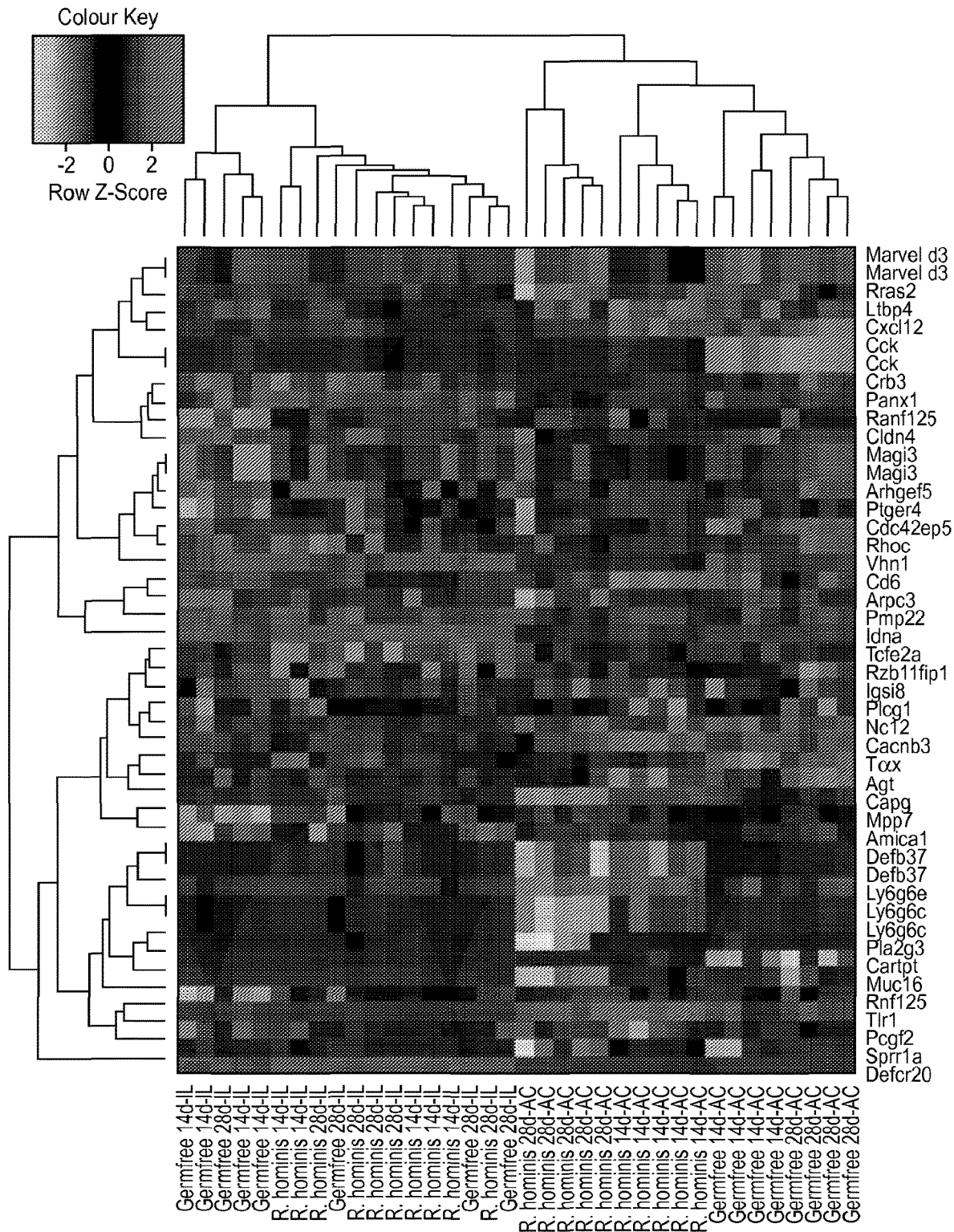
Figure 4C:
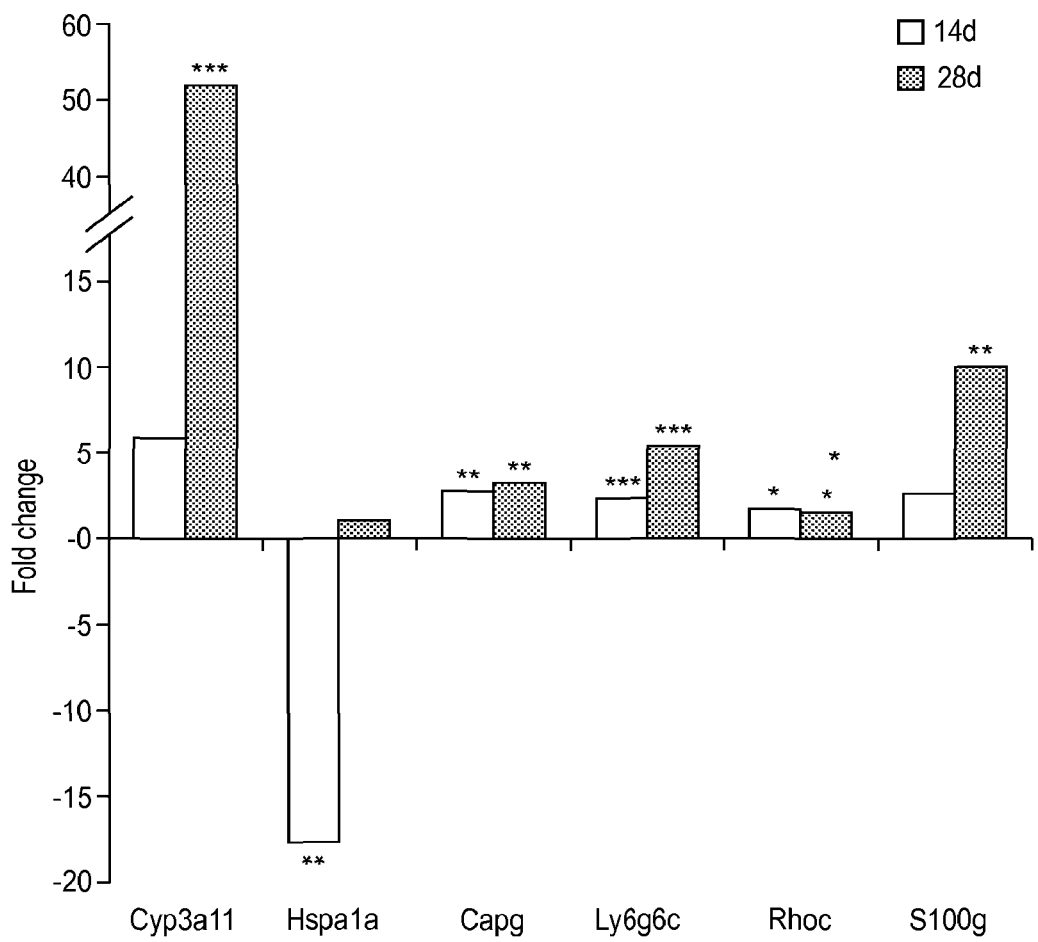
Figure 5A:
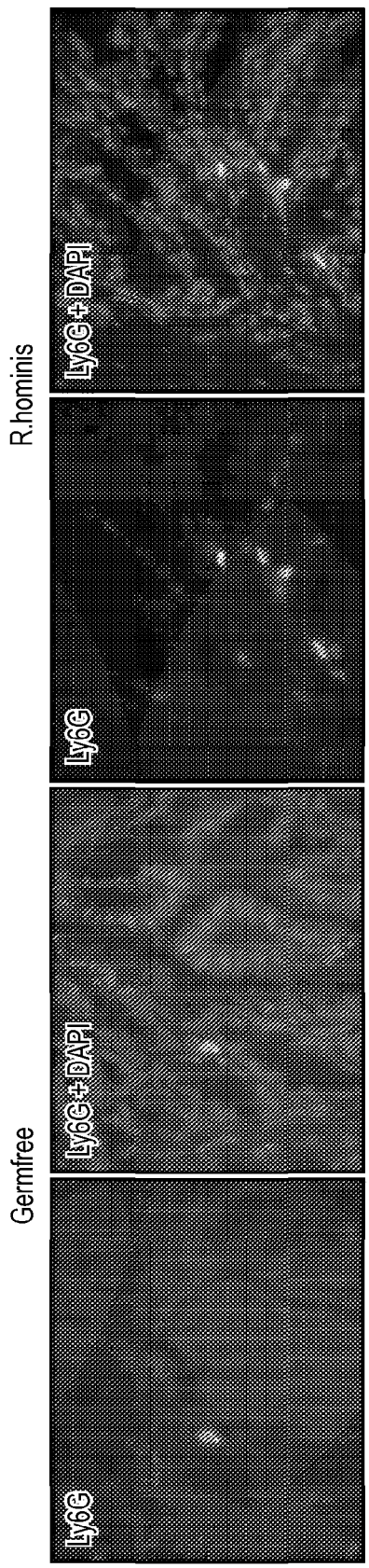
FIG. 5 shows expression and localization of T cell markers in colon. Immunofluorescence and analysis of lamina propria cells labeled with anti-Ly6G (A), anti-CD3 (B) and anti-CD11b (C) in lamina propria of GF mice and *R. hominis*-treated mice. *$P<0.05$.
Figure 5A:
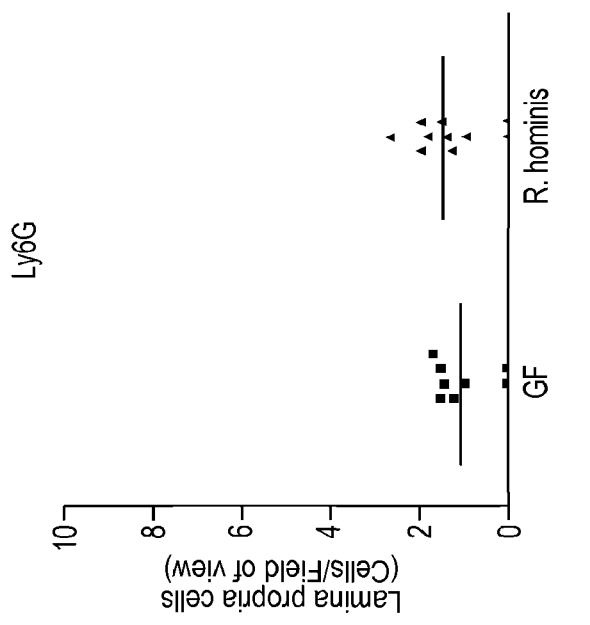
Figure 5B:
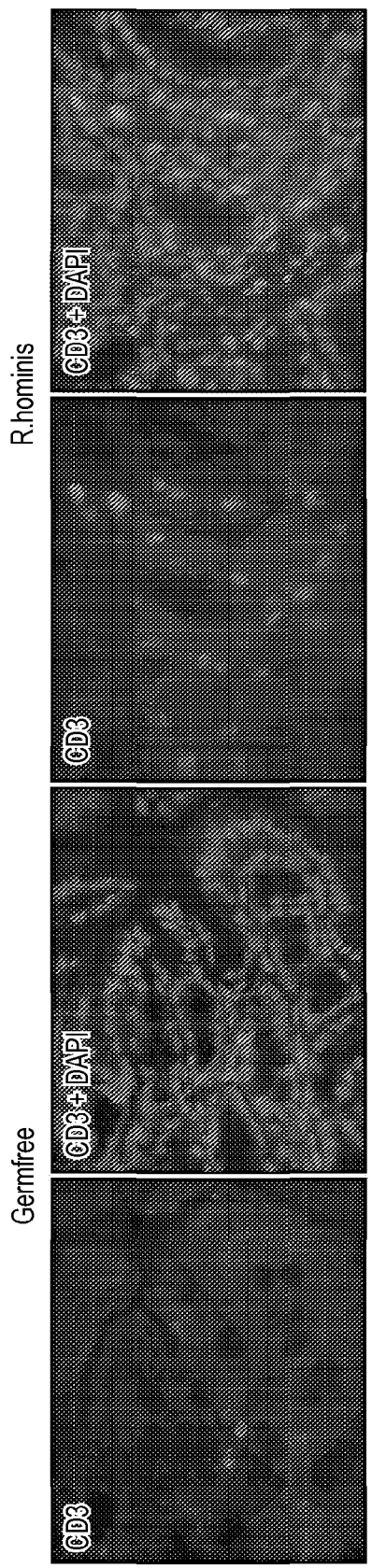
Figure 5B:
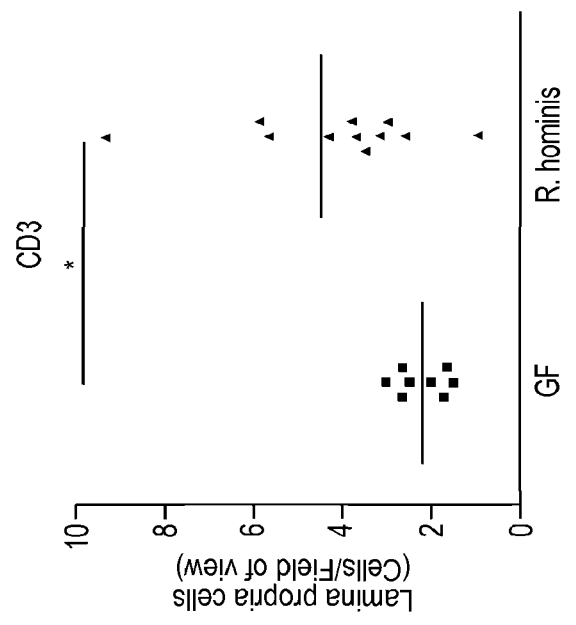
Figure 5C:
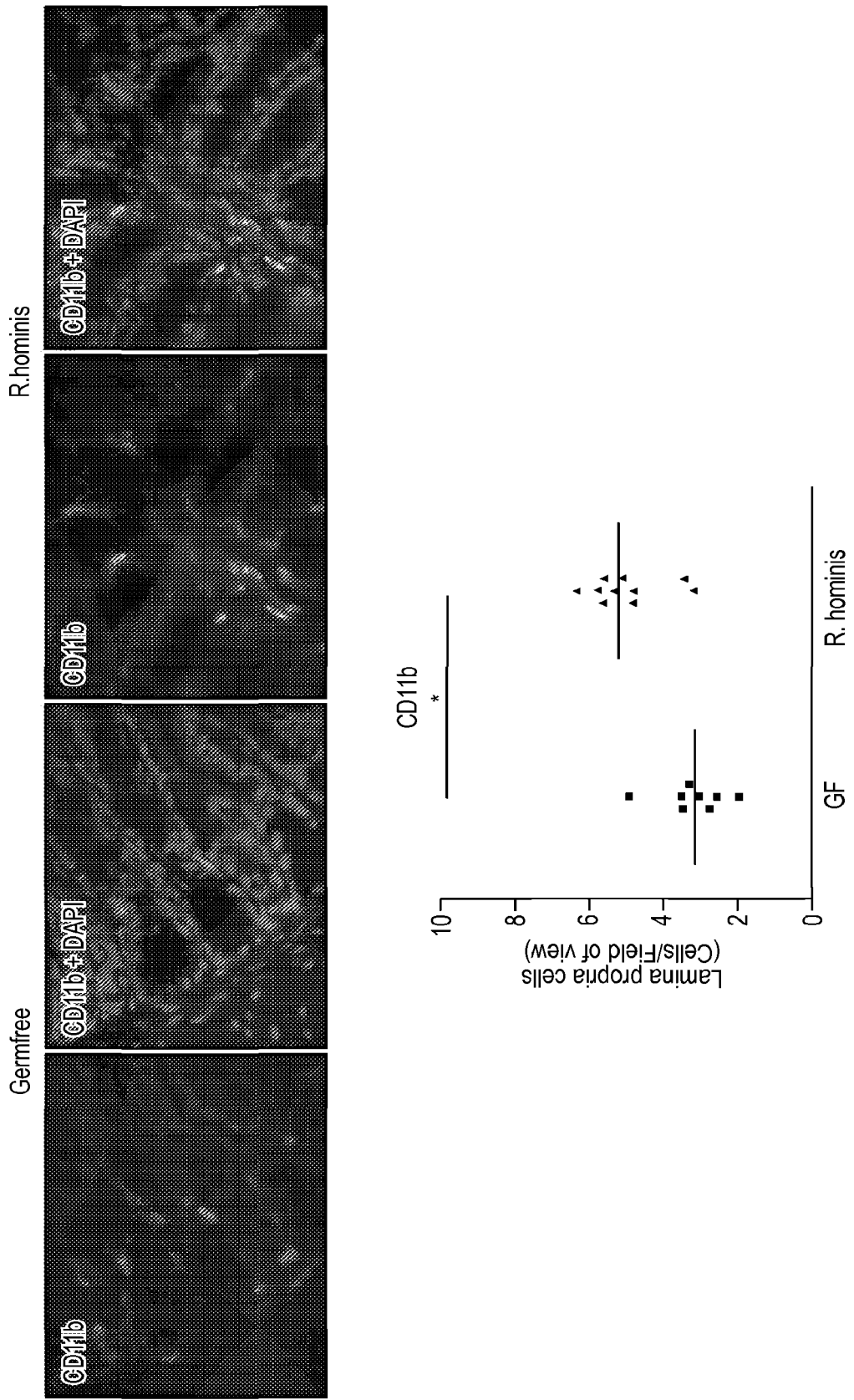
Figure 5D:
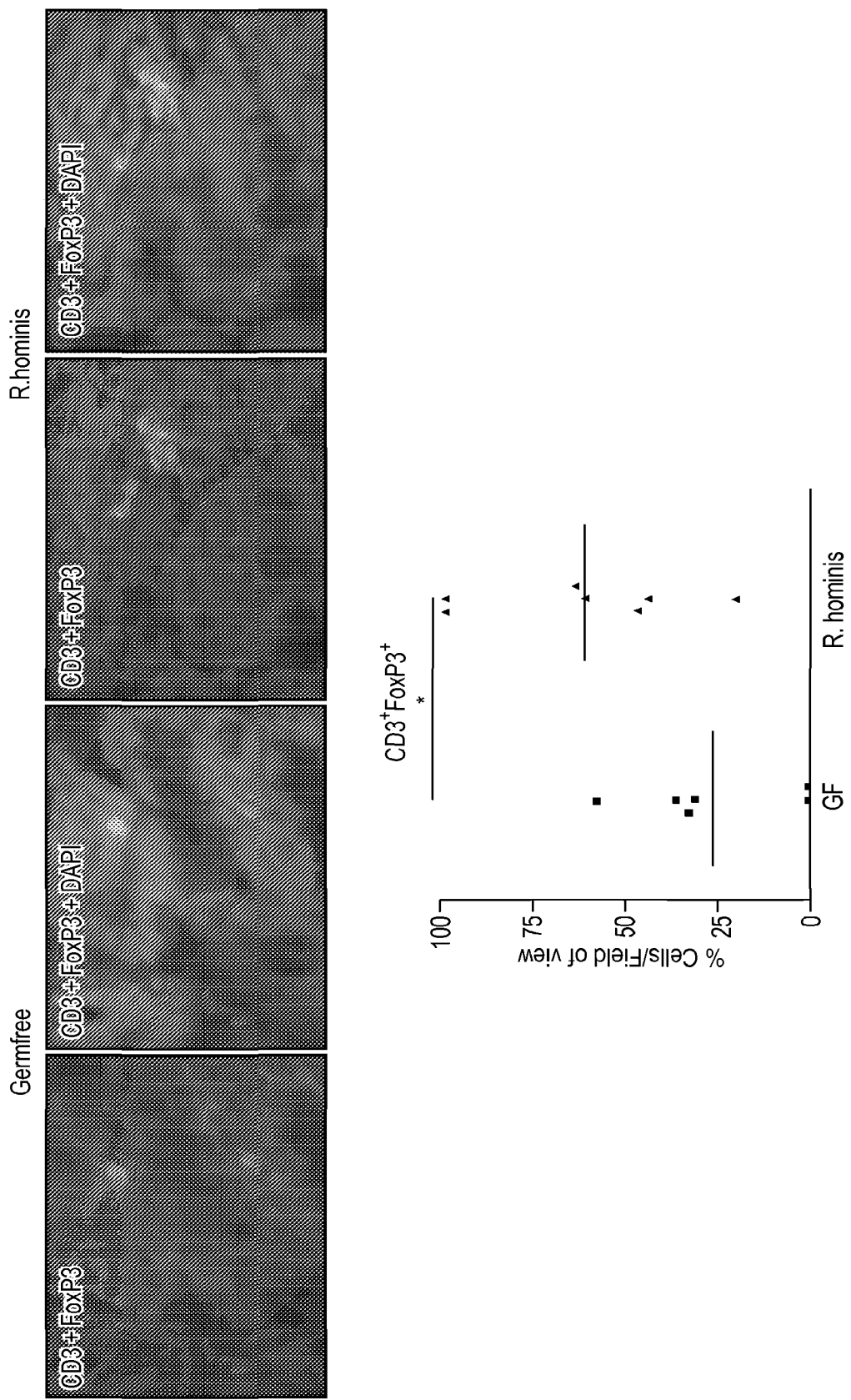

To further investigate the effects of host-adaptation on the *R. hominis* transcriptome, in vitro stimulation of human intestinal epithelial cells (Cato-2 and HT-29) was performed. This showed that the conjugation/mobilization transfer gene mobA/mobL protein1, which was induced by adaptation to the mouse gut, was also increased in both cell lines (FIG. 3F). Consistent with the in vivo data, the flagellin gene MotA was upregulated in Caco-2 cells. Genes involved in butyrate metabolism showed differences between the two cell lines, with downregulation seen in Caco-2 cells and upregulation in HT-29 cells. *R. hominis* Affects T Cell Pathways Mostly in the Colon The colonization of GF mice with *R. hominis* correlated with increased gut gene expression which was highest in the colon. (FIG. 4A). Differential expression was most profound at 28d after colonization, with 159 genes up-regulated and 143 genes down-regulated. The number of differentially expressed genes in the ileum at 14d was similar to the ascending colon, with 79 genes up-regulated and 119 genes down-regulated. Differential expression in the ileum was very low at 28d, consistent with reduced colonization levels. The transcriptomic response differed at the two time-points, as shown by the clear separation of significant transcripts by heatmap analysis (FIG. 4B). Positive Real-time PCR validation of Affymetrix data is shown in FIG. 4C.

The majority of pathways affected at 14d in the ileum and the ascending colon grouped into the categories cell differentiation, cell cycle regulation and tissue remodeling.

Figure 7:
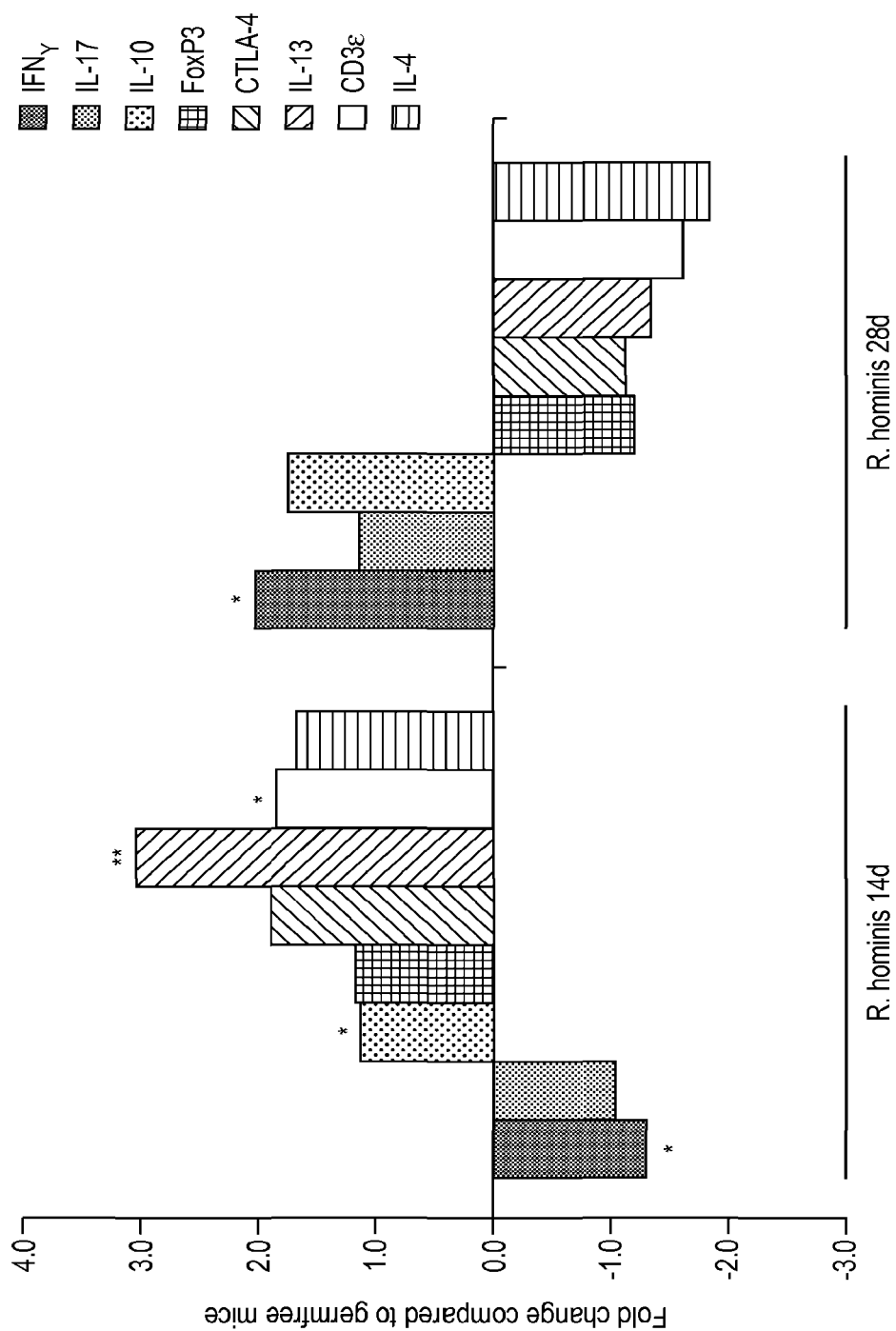
FIG. 7 shows real-time PCR analysis of mRNA levels of IL-10, IL-17 and IFN-γ. Real-time PCR was performed on ascending colon tissue for measurement of T cell markers. Real-time PCR results are means of triplicates, *$P<0.05$, **$P<0.01$.
Figure 8A:
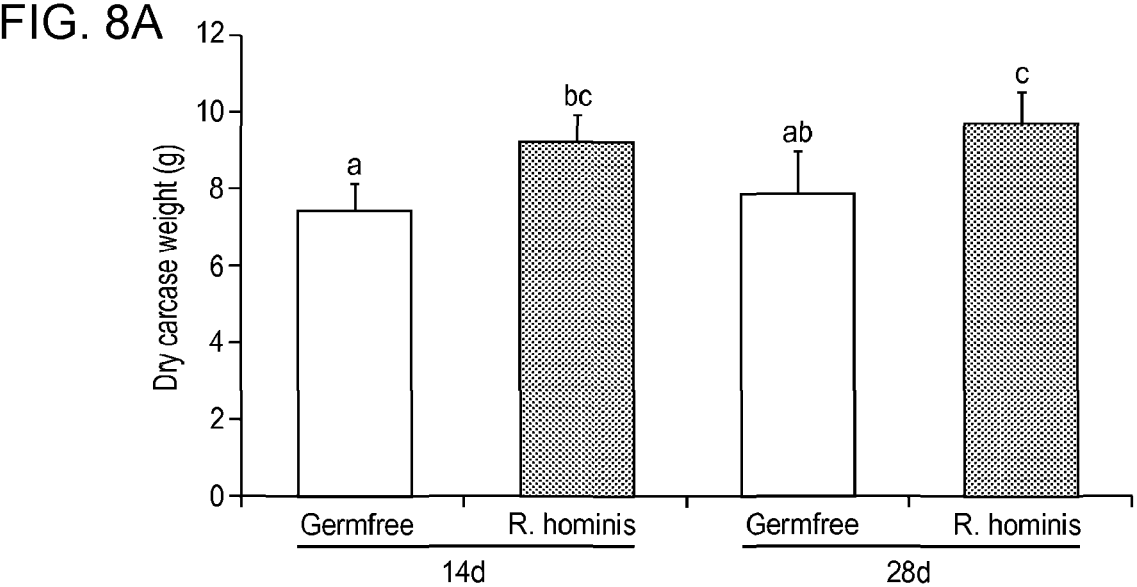
FIG. 8 shows the effects of mono-association of GF mice with *R. hominis* on body weight composition. Dry body weight and lipid carcass analysis was performed. (A) Dry carcass weights of *R. hominis*-associated mice were significantly heavier compared to GF animals. (B) Further carcass lipid analysis showed that total adiposity was also significantly higher in *R. hominis*-treated animals at 14d.
Figure 8B:
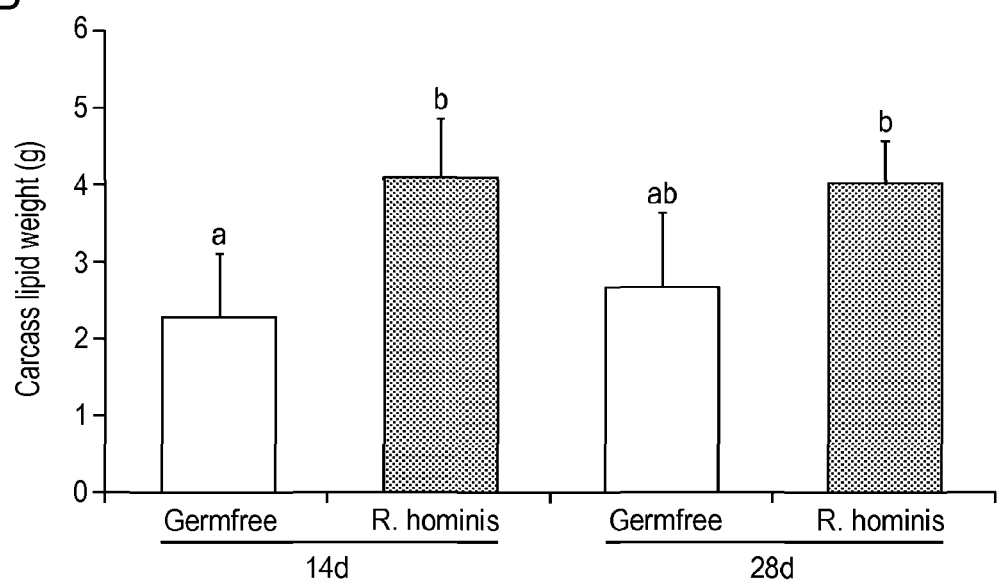

Importantly, immune response was the major pathway group induced at 28d in the ascending colon. The 36 significantly affected pathways in this category were mostly involved in T cell function and included the IL-10 signaling pathway, the ICOS pathway in T-helper cell and regulation of T cell function by CTLA-4. The genes involved in these pathways showed both up-regulation and down-regulation, so while these pathways were significantly affected by the presence of *R. hominis*, the precise net functional effects on T cell differentiation requires further investigation. However, enhanced IL-10, CD3s and IL-13 and changed expression of IFN-y was confirmed by Real-time PCR (FIG. 7), suggesting that *R. hominis* colonization may favor Treg and Th2 cell differentiation pathways. Gene Ontology analysis was applied to obtain additional information on the functional classification of differentially regulated genes. The GO-process for 'actin polymerization' (G0:0030041) (Arpc3, Capg, Cdc42ep5 and Rhoc) was up-regulated at 28d in the colon in *R. hominis* colonized mice (FIG. 8). Actin polymerization at the immune synapse is required for T cell activation and effector function. Gene induction was further confirmed by Real-time PCR (FIG. 4C). Overall, this data indicates that *R. hominis* actively effects the adaptive immune response in the colon by positively influencing T cell regulation.

Related to these results was the induction of members of the Ly6 family in the ascending colon. In particular, the GPI-anchored gene product of Ly6g6c was up-regulated 25-fold, and the related gene Ly6g6e was up-regulated twofold at 28d. Most hematopoietic cells express one or more members of the Ly6 family including neutrophils and plasmacytoid dendritic cells. Furthermore, a possible role of Ly6 in T cell activation, differentiation and maturation has been proposed (15).

Immunocytochemistry confirmed increased presence of Ly6G+, CD11b+ and CD3+ cells in *R. hominis*-colonized mice (FIG. 5). Consistent with the data showing T cell pathways mainly dominated by Treg responses, was a statistically significant increase in double-positive CD3+ FoxP3+ T cells in the colon of *R. hominis*-inoculated mice. Clearly colonization of *R. hominis*, as a single bacterial species, induced a significant increase in a population of CD3+ FoxP3+ cells, particularly in the colon of these mice. *R. hominis* Modulates Innate Immune Response Genes in Both the Ileum and Colon and Attenuates Colitis in IL 10KO Mice Genes involved in innate immunity and gut barrier function were significantly induced by the presence of *R. hominis* in the ascending colon. The GO-process 'innate immune response' (G0:0045087) was up-regulated and included the TLR-related genes Tlr5, Tlr1 and Vnn1. The up-regulation of Tlr5 was interesting, particularly given the corresponding induction of flagellar genes and the presence of flagellin protein in *R. hominis* during gut colonization, and may infer a role for this innate signaling pathway in mediating other innate and adaptive immune responses. The coupling between TLR5 signaling and CD4+ T cell responses has recently been demonstrated for flagellate pathogens (16). Similarly, the role off LR2 in facilitating the colonization of *Bacteroides fragilis*, Treg propagation and immune homeostasis has been shown (17).

Other innate immune genes affected in the colon by *R. hominis* included the antimicrobial peptides Defb37, Pla2g3, Muc16 and It1n and the gut barrier function genes Sprr1a, Cldn4, Pmp22, Crb3 and Magi3. Innate immune genes showing up-regulation in the ileum in response to *R. hominis* included Defcr20, Pcgf2, Ltbp4, Igsf8 and Tcfe2a. Interestingly, Pcgf2 negatively regulates the expression of different cytokines, chemokines, and chemokine receptors and may play an important role in controlling inflammatory responses in gut tissues in response to this commensal bacterium. Interestingly, we also showed negative regulation of the NF-KB pathway (G0:0043124) by *R. hominis*, which, like *B. thetaiotaomicron* (19), may contribute to immune homeostasis by down-regulating this inflammatory cascade.

Figure 6A:
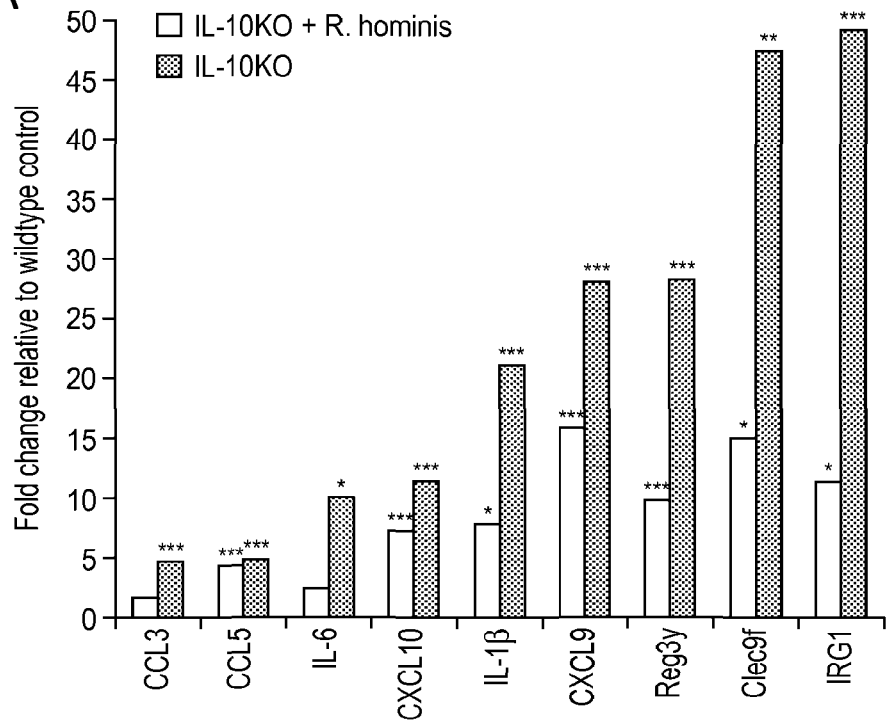
FIG. 6 shows the anti-inflammatory effects of *R. hominis* in an experimental model of colitis. IL-10KO mice were dosed three times a week for 14 weeks. (A) Untreated IL-10KO mice had strong elevation of all genes compared to wild-type mice, while differential gene expression was lower in *R. hominis*-treated animals. Real-time PCR results are means of triplicates, *$P<0.05$, $P<0.01$, *$P<0.001$. (B) Bodyweights of untreated IL-10KO and *R. hominis*-treated IL-10KO animals at the end of the study. (C) Ascending colon (haematoxylin/eosin stained) of IL-10KO and *R. hominis* treated IL-10KO animals. Original magnification ×100.
Figure 6B:
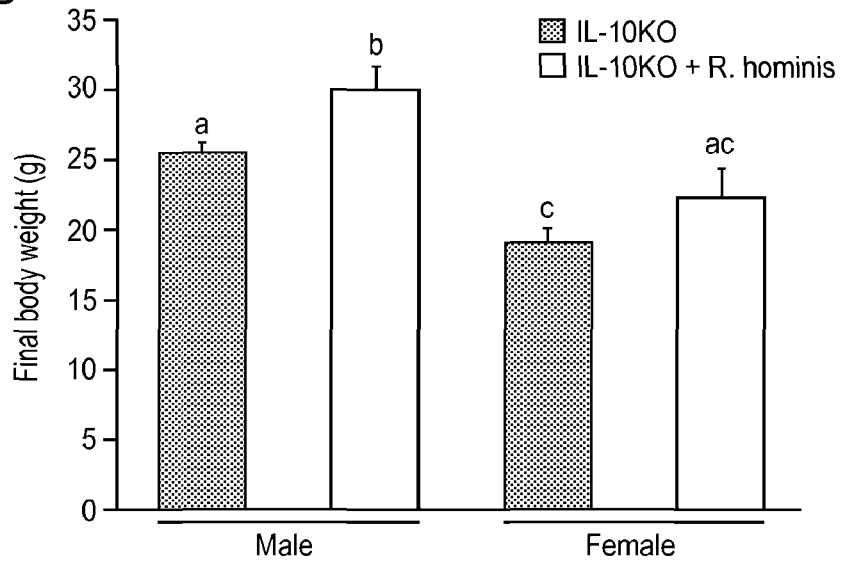
Figure 6C:
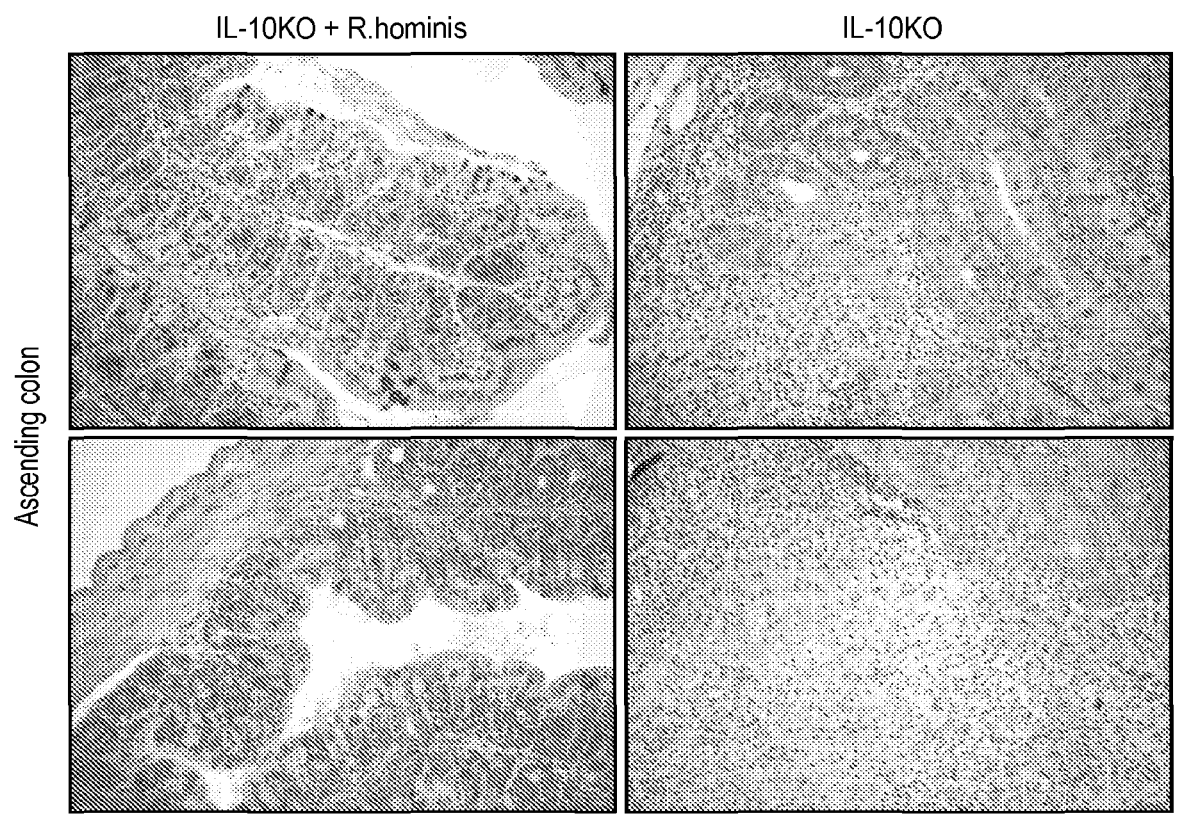

The IL-10 knockout mouse model was used to test the therapeutic efficacy of *R. hominis*, due to the control of inflammatory pathways as well as the positive effects on Treg induction in mono-associated mice. Mice were dosed (~50 µl, $10^{10}$ CFU) three times a week from weaning at 20d of age for a period of 14 weeks. Gene expression of a panel of pro-inflammatory biomarkers showed that untreated IL-10KO mice had strong elevation of all investigated genes compared to wild-type mice, with gene induction ranging from 4- to 49-fold (FIG. 6A). Pro-inflammatory gene induction was significantly lower in R. hominis-treated compared to untreated mice, indicating strong therapeutic benefits of oral administration of R. hominis. Bodyweights of R. hominis-treated animals were also heavier at the end of the study compared to untreated animals, and this effect was statistically significant in males (FIG. 6B). Finally, histological analysis showed the presence of severe inflammation in the ascending colon of untreated IL-10KO, while R. hominis-treated animals had a relatively healthy-looking colonic mucosa. R. hominis Colonization Influences Satiety Genes and Body Composition Significant metabolic actions of R. hominis in mono-associated mice were also evident. The GO-processes 'negative regulation of response to food' (G0:0032096), 'negative regulation of appetite' (G0:0032099), and 'regulation of catecholamine secretion' (G0:0050433) were all down-regulated in the ascending colon after colonization with R. hominis. This data infers that R. hominis exerts a stimulatory effect on host appetite. The genes involved in these processes were Agt, Cartpt, Cck and Cxcl12, with fold changes ranging from 2- to 12-fold. Cck, in particular, plays a major role in digestion and satiety as a hunger suppressant. Gcg also showed down-regulation at this gut site.

To establish whether these gene changes had physiological relevance in relation to food intake and body composition, dry carcass weight and composition analyses were performed. Interestingly, the dry carcass weights of R. hominis-associated mice were significantly heavier compared to GF animals, and the differences were most discernable at 14d. Further carcass lipid analysis showed that total adiposity was also significantly higher in R. hominis-treated animals at 14d. These finding are consistent with recent data revealing the role of Firmicutes in energy harvest through dietary fermentation, but also support the notion that gut bacteria can in fact modulate the brain-gut axis and appetite-regulating hormones. Discussion The long-term co-evolution of host-microbe mutualism has likely driven the selection of functionally important bacterial species in the gut, the majority of which are not highly represented in other ecosystems. Currently, there is limited information regarding the contribution of individual members of the microbial community to intestinal functions, particularly in relation to development of the mucosal immune system.

Recent work using a reversible colonization model based on E. coli (HA 107) has demonstrated that live bacteria are required in numbers approaching $10^8$ CFU s per gram of content for the immune-inducing effects on IgA (20). Recently, the specific functions of SFB and Bacteroides fragilis have been investigated in the mouse gut to define their individual contributions to T cell biology and both these bacteria have been shown to be potent inducers of Tregs and Th17 cells (5, 8, 9). The effects of individual members of the cluster XIVa Firmicutes have not been reported previously, although their presence in the ASF, which also affects T cell differentiation has been noted (10).

The applicant has demonstrated herein the first successful mono-association of the germ-free mouse gut with an anaerobic bacterium, R. hominis, which is a member of the Firmicutes phylum. The extreme oxygen sensitivity of bacteria like Roseburia requires strict anaerobic culture techniques, making it difficult to perform functional characterization. The applicant established stable mono-colonization of R. hominis in germfree mice and produced the complete annotated genomic sequence to uncover its metabolic organization, physiology, and symbiotic properties. It was found that the transcriptional responses of R. hominis following colonization could be attributed to both the host gut environment and diet. The host-driven effects dominated the response of R. hominis following mono-association. These included gene transfer, membrane transport, chemotaxis and motility subsystems. The strong up-regulation of genes involved in mobilization transfer supports the view that the gut environment is highly conducive to horizontal gene exchange between members of the gut microbiota. Thus, this environment may accelerate the dissemination of genes important for bacterial survival, colonization and function within the gut ecosystem.

The role of motility and flagellar apparatus in host colonization is well-elaborated for pathogenic bacteria but much less is known about the role of flagellar proteins in commensal bacteria. In vivo experiments revealed a stimulatory effect of the host intestinal environment on the expression of flagellin genes. Flagellin signals are perceived by host TLR5 receptors (24) and many pathogenic flagellin structures induce strong pro-inflammatory responses (24). Signaling through TLR5 in response to by resident flagellated commensals may be important for homeostasis, since deletion of TLR5 results in spontaneous colitis in mice (25). The enhanced expression of R. hominis flagellin in vivo is therefore of potential interest. Other work has shown that E. coli flagellin mutants have a colonization advantage over wildtype flagellated strains, possibly due to absence of innate recognition by TLR5 signaling (26, 27). The applicant has shown that for certain Firmicutes, upregulation of flagellin is a natural response to gut colonization. R. hominis flagellin protein remains expressed in vivo and correlates with sustained colonization, absence of overt inflammation and expansion of T cells of regulatory phenotype. Hence, commensal flagellin structures through TLR5 may help direct immune tolerance responses. Additional data based on TLR5KO and flagellin mutants of R. hominis will further clarify the importance of commensal flagellins in relation to immune homeostasis but the observed protective effect of R. hominis in IL-10 KO mice supports this hypothesis, although other signaling moieties such as butyrate may also contribute to immune regulation.

A clear role was established for R. hominis in promoting gut barrier function and innate immunity in the mouse colon. Tight junctions, gap junctions and adherens junctions operate to limit bacterial translocation to the subepithelial layer (28). Both Crohn's disease and ulcerative colitis are characterized by loss of barrier function and tight junction integrity. Interestingly, dysbiosis of the gut microbiota in IBD is associated with a reduction in Firmicutes (1, 29). The observation that R. hominis actively enhances the expression of barrier genes suggests that their loss in IBD patients may be functionally significant. Activation of tight junction complexes is not just the prerogative of R. hominis; other commensals, such as Bacteroides thetaiotaomicron and Lactobacillus acidophilus, also enhance mucosal barrier function (18, 30), inferring probiotic opportunities with these bacteria in human IBD.

The effects of R. hominis on the gut immune system were intriguing. The strongest effects were noted in the ascending colon and genes such as Ly6g6c were strongly up-regulated, as well as pathways involved in T cell regulation and differentiation and actin polymerization at the immune synapse, which are implicated in T cell activation and effector functions. Although the expression of Treg genes in response to *R. hominis* colonization was not very strong, the most affected T cell pathways included those related to IL-10, ICOS and CTLA-4, which are all involved in supporting Treg differentiation. Importantly, the applicant was able to demonstrate significant increases in CD3+FoxP3+ cells in the colons of these mice. These findings complement the recent data on other *Clostridium* species that drive Treg differentiation. Clearly, *R. hominis* can promote mucosal T cell expansion and impacts on T cell differentiation.

It was interesting to note the strong immune effects in the colon compared to the ileum, especially at 28d after mono-colonization with *R. hominis*. The transcriptomic data at 14d suggests that some immune priming could be initiated in ileum at this time-point. The effects on the different T cell subsets in the ascending colon at 28d may thus reflect a trafficking and homing of cells from ileum to mesenteric lymph node to the colon.

An interesting additional biological effect of *R. hominis* colonization was the regulation of genes influencing responses to food and control of appetite. In particular, the satiety hormones Cck and Gcg were significantly reduced. The effects of Cck on food intake are mediated via a vagal afferent pathway. This is the major neural pathway by which information about ingested nutrients reaches the central nervous system to influence both gut function and feeding behavior. Cck acts on the vagal system to decrease expression of molecules that stimulate appetite and feeding, and to increase expression of molecules that inhibit feeding and decrease appetite (Npy2r and Cartpt, both down-regulated two-fold in the current study). No link between Cck, Gcg and commensal bacteria has been reported thus far, however, both fatty acids and proteins are potent inducers of Cck and Gcg (31). *R. hominis* produces short-chain fatty acids such as butyrate with aliphatic tails of less than six carbons; this metabolic activity has been reported to reduce the stimulatory effect on plasma Cck observed with longer chain fatty acids (32). Interestingly, carcass weight analysis revealed that both body weight and lipid content was indeed significantly increased with *R. hominis*, consistent with body weight increases observed in conventionalization of germfree mice (33). Whether this is a direct effect of a reduction in satiety hormones as seen in the current study remains to be seen, as the involvement of Cck and Gcg has not been reported previously. However, it is important to acknowledge that a link between microbiota colonization and energy harvest from the diet, in part through release of SCFAs, has been shown previously (34). Given that *R. hominis* is a major butyrate producer, this mechanism is likely also to contribute to the metabolic efficiency observed following *R. hominis* treatment.

In summary, mono-association of the murine gut with *R. hominis* induced strong bi-directional gene expression events consistent with changes in bacterial membrane transport, chemotaxis and motility of this gut-adapted bacterium and a concomitant activation of the innate and adaptive immune system of the host. This metabolically active bacterium also exerted important effects on appetite and satiety genes which correlated with enhanced body weight gain in colonized mice. Compositions Another aspect of the invention relates to a composition comprising a bacterial species as described above and a pharmaceutically acceptable excipient, carrier or diluent. Suitable excipients, diluents, carriers are described below.

The composition may be any composition, but is preferably a composition to be administered orally, enterally or rectally. For example, the composition may be an edible composition. "Edible" means a material that is approved for human or animal consumption.

Another aspect of the invention relates to a probiotic composition comprising a bacterial species as described above.

As used herein, the term "probiotic" means microbial cell preparations or components of microbial cells with a beneficial effect on the health or well-being of the host. (Salminen S, Ouwehand A. Benno Y. et al "Probiotics: how should they be defined" Trends Food Sci. Techno. 1999:10 107-10).

Preferably, the probiotic composition is an orally administrable composition of metabolically active, i.e., live and/or or lyophilized, or non-viable heat-killed, irradiated or lysed probiotic bacteria. The probiotic composition may contain other ingredients. The probiotic composition of the invention can be administered orally, i.e., in the form of a tablet, capsule or powder. Encapsulated products are favoured for *R. hominis* as it is an anaerobe. Other ingredients (such as vitamin C, for example), may be included as oxygen scavengers. Prebiotic substrates such as these improve the colonisation and survival in vivo. Alternatively, the probiotic composition of the invention may be administered orally as a food or nutritional product, such as milk or whey based fermented dairy product, or as a pharmaceutical product.

A suitable daily dose of the probiotic bacteria is from about $1 \times 10^3$ to about $1 \times 10^{11}$ colony forming units (CFU), more preferably from about $1 \times 10^7$ to about $1 \times 10^{10}$ CFU, more preferably, about $1 \times 10^6$ to about $1 \times 10^{10}$ CFU.

In one preferred embodiment, the composition contains the bacterial species and/or cellular components thereof, as active ingredients, in an amount of from about $1 \times 10^6$ to about $1 \times 10^{11}$ CFU/g, respect to the weight of the composition, preferably from about $1 \times 10^8$ to about $1 \times 10^{10}$ CFU/g. The dose may be of 1 g, 3 g, 5 g, and 10 g.

Typically, a probiotic is optionally combined with at least one suitable prebiotic compound. A pre biotic is usually a non-digestible carbohydrate such as an oligo- or polysaccharide, or a sugar alcohol, which is not degraded or absorbed in the upper digestive tract. Known prebiotics include commercial products such as inulin and transgalacto-oligosaccharides.

Preferably, the composition of the present invention includes a pre biotic in an amount of from about 1 to about 30% by weight, respect to the total weight composition, preferably from 5 to 20% by weight. Preferred carbohydrates are selected from: fructo-oligosaccharides (or FOS), short-chain fructo-oligosaccharides, inulin, isomalt-oligosaccharides, pectins, xylo-oligosaccharides (or XOS), chitosan-oligosaccharides (or COS), beta-glucans, arable gum modified and resistant starches, polydextrose, D-tagatose, acacia fibers, carob, oats, and citrus fibers. Particularly preferred prebiotics are the short-chain fructo-oligosaccharides (for simplicity shown hereinbelow as FOSs-c.c); said FOSs-c.c. are not digestible carbohydrates, generally obtained by the conversion of the beet sugar and including a saccharose molecule to which three glucose molecules are bonded. Feedstuffs/Products A further aspect of the invention relates to food products, dietary supplements, nutraceuticals, nutritional formulae, drinks and medicaments containing a bacterial species as defined above, and use thereof.

In one preferred embodiment, the composition comprises additionally at least one other kind of other food grade bacterium, wherein the food grade bacterium is preferably selected from the group consisting of lactic acid bacteria, bifidobacteria, propionibacteria or mixtures thereof.

One aspect of the invention relates to a food product comprising the bacterial species defined above. The term "food product" is intended to cover all consumable products that can be solid, jellied or liquid. Suitable food products may include, for example, functional food products, food compositions, pet food, livestock feed, health foods, feedstuffs and the like. In one preferred embodiment, the food product is a health food.

As used herein, the term "functional food product" means food that is capable of providing not only a nutritional effect, but is also capable of delivering a further beneficial effect to the consumer. Accordingly, functional foods are ordinary foods that have components or ingredients (such as those described herein) incorporated into them that impart to the food a specific functional—e.g. medical or physiological benefit—other than a purely nutritional effect.

Examples of specific food products that are applicable to the present invention include milk-based products, ready to eat desserts, powders for re-constitution with, e.g., milk or water, chocolate milk drinks, malt drinks, ready-to-eat dishes, instant dishes or drinks for humans or food compositions representing a complete or a partial diet intended for pets or livestock.

In one preferred embodiment the composition according to the present invention is a food product intended for humans, pets or livestock. The composition may be intended for animals selected from the group consisting of dogs, cats, pigs, cattle, horses, goats, sheep or poultry. In a preferred embodiment, the composition is a food product intended for adult species, in particular human adults.

In the present invention, "milk-based product" means any liquid or semi-solid milk or whey based product having a varying fat content. The milk-based product can be, e.g., cow's milk, goat's milk, sheep's milk, skimmed milk, whole milk, milk recombined from powdered milk and whey without any processing, or a processed product, such as yoghurt, curdled milk, curd, sour milk, sour whole milk, butter milk and other sour milk products. Another important group includes milk beverages, such as whey beverages, fermented milks, condensed milks, infant or baby milks; flavoured milks, ice cream; milk-containing food such as sweets.

One aspect of the invention relates to a feedstuff or animal feed comprising the bacterial species defined above.

The compositions of the present invention may be—or may be added to—food supplements, also referred to herein as dietary or nutritional supplements or food additives. Thus, another aspect of the invention relates to a dietary supplement or food additive comprising one or more bacterial strains according to the invention.

The bacterial species and probiotic compositions according to the invention may also be used in animal nutrition (e.g. in pig nutrition), particularly in the early-weaned period and growing fattening period. The probiotics are expected to enhance immune function reduce and prevent infectious diseases, beneficially alter the microbiota composition, and improve growth and performance of animals, for example, through increased feed conversion efficiency.

Diluents, Excipients and Carriers

As mentioned above, the invention also relates to compositions, more preferably pharmaceutical compositions or nutritional supplements, comprising the bacterial species defined above, and use thereof. The bacterial species is generally administered in admixture with a pharmaceutically or nutritionally acceptable carrier, excipient or diluent, particularly for human therapy. The pharmaceutical compositions may be for human or animal usage in human and veterinary medicine.

Examples of such suitable excipients for the various different forms of pharmaceutical compositions described herein may be found in the "Handbook of Pharmaceutical Excipients, 2nd Edition, (1994), Edited by A Wade and P J Weller.

Acceptable carriers or diluents for therapeutic use are well known in the pharmaceutical art, and are described, for example, in Remington's Pharmaceutical Sciences, Mack Publishing Co. (A. R. Gennaro edit. 1985).

Examples of suitable carriers include lactose, starch, glucose, methyl cellulose, magnesium stearate, mannitol, sorbitol and the like. Examples of suitable diluents include ethanol, glycerol and water.

The choice of pharmaceutical carrier, excipient or diluent can be selected with regard to the intended route of administration and standard pharmaceutical practice. The pharmaceutical compositions may comprise as, or in addition to, the carrier, excipient or diluent any suitable binder(s), lubricant(s), suspending agent(s), coating agent(s), solubilising agent(s).

Examples of suitable binders include starch, gelatin, natural sugars such as glucose, anhydrous lactose, free-flow lactose, beta-lactose, corn sweeteners, natural and synthetic gums, such as acacia, tragacanth or sodium alginate, carboxymethyl cellulose and polyethylene glycol.

Examples of suitable lubricants include sodium oleate, sodium stearate, magnesium stearate, sodium benzoate, sodium acetate, sodium chloride and the like.

Preservatives, stabilizers, dyes and even flavoring agents may be provided in the pharmaceutical composition. Examples of preservatives include sodium benzoate, sorbic acid and esters of p-hydroxybenzoic acid. Antioxidants and suspending agents may be also used.

Nutritionally acceptable carriers, diluents and excipients include those suitable for human or animal consumption and that are used as standard in the food industry. Typical nutritionally acceptable carriers, diluents and excipients will be familiar to the skilled person in the art.

Administration

The compositions of the present invention may be adapted for oral, rectal, vaginal, parenteral, intramuscular, intraperitoneal, intraarterial, intrathecal, intrabronchial, subcutaneous, intradermal, intravenous, nasal, buccal or sublingual routes of administration. Preferably, the compositions of the present invention are adapted for oral, rectal, vaginal, parenteral, nasal, buccal or sublingual routes of administration.

For oral administration, particular use is made of compressed tablets, pills, tablets, gellules, drops, and capsules.

Other forms of administration comprise solutions or emulsions which may be injected intravenously, intraarterially, intrathecally, subcutaneously, intradermally, intraperitoneally or intramuscularly, and which are prepared from sterile or sterilisable solutions. The pharmaceutical compositions of the present invention may also be in form of suppositories, pessaries, suspensions, emulsions, lotions, ointments, creams, gels, sprays, solutions or dusting powders.

An alternative means of transdermal administration is by use of a skin patch. For example, the active ingredient can be incorporated into a cream consisting of an aqueous emulsion of polyethylene glycols or liquid paraffin. The bacterial strain can also be incorporated into an ointment consisting of a white wax or white soft paraffin base together with such stabilisers and preservatives as may be required.

Compositions may be formulated in unit dosage form, i.e., in the form of discrete portions containing a unit dose, or a multiple or sub-unit of a unit dose. Dosage A person of ordinary skill in the art can easily determine an appropriate dose of one of the instant compositions to administer to a subject without undue experimentation. Typically, a physician will determine the actual dosage which will be most suitable for an individual patient and it will depend on a variety of factors including the activity of the specific bacterial strain employed, the metabolic stability and length of action of that strain, the age, body weight, general health, sex, diet, mode and time of administration, rate of excretion, drug combination, the severity of the particular condition, and the individual undergoing therapy. The dosages disclosed herein are exemplary of the average case. There can of course be individual instances where higher or lower dosage ranges are merited, and such are within the scope of this invention.

The usual effective daily dose in humans is from about $1 \times 10^3$ to about $1 \times 10^{11}$, more preferably, from about $1 \times 10^7$ to about $1 \times 10^{11}$, even more preferably, from about $1 \times 10^6$ to about $1 \times 10^{10}$ CFU. Combinations In a particularly preferred embodiment, the compositions of the invention are administered in combination with one or more other active agents. In such cases, the compositions of the invention may be administered consecutively, simultaneously or sequentially with the one or more other active agents.

The present invention is further described by way of the following non-limiting examples. Examples Materials and Methods Bacterial Growth Conditions R. hominis A2-183T(=DSM 16839T=NCIMB 14029T) was grown anaerobically on synthetic YCFA or complex M2GSC media. Culture was inoculated from frozen stock into Hungate tubes and incubated overnight at 37° C. Bacteria were then grown on M2GSC agar plates for 48 h in a MACS-MG-1 000 anaerobic workstation (Don Whitley Scientific) under 80% $N_2$, 10% $CO_2$, and 10% $H_2$ at 37° C. The effect of mucin was investigated by adding 0.5% (w/v) mucin from porcine stomach type III (Sigma-Aldrich) to the YCFA medium.

For colonization of germfree mice, R. hominis was grown in YCFA media overnight at 37° C. The culture was spun down and the pellet was resuspended in one mL of YCFA media, supplemented with 2% cysteine (w/v, SigmaAldrich) and 3% ascorbic acid (w/v, Sigma-Aldrich).

Animal Experiments

Germ-free animal experiments were performed in the INRA gnotobiotic rodent breeding facility at Jouy-en-Josas (ANAXEM plateform, Institut Micalis, INRA, Jouy-en-Josas, France). All animal experiments were approved by the local ethical committee. Eighteen germfree C3H/HeN male mice were allocated into control (N=8) and treatment (N=10) groups and caged individually in plastic isolators. The mice were fed ad libitum on a sterilized commercial diet (R03-40; UAR). At day 0, animals in the treatment group were given 100 µL of R. hominis culture by gavage, while control animals were given 100 µL YCFA media. At day 14 and 28, four control animals and five R. hominis-treated animals were sacrificed. C57/BL6 IL-10KO experiments were performed at the Rowett Institute of Nutrition and Health (Aberdeen, Scotland, UK). Wild-type mice (N=8), IL-10KO (N=12) and IL-10KO+R. hominis (N=11) were analysed 14 weeks from the outset of the experiment. Briefly R. hominis was administered 3 times per week at $10^9$ cfu/day.

The ileum, ascending colon and descending colon were divided into four equal parts and transferred to RNAlater (Ambion), neutral buffered formalin (Sigma-Aldrich) or liquid nitrogen. The whole caecum and transverse colon were transferred to RNAlater. Histopathology was also evaluated in the IL-10KO mice.

Tissue Culture Experiments

All cell culture reagents, unless specified otherwise, were supplied by Sigma-Aldrich. $2 \times 10^5$ Caco-2 or HT29 cells in 1.5 mL DMEM (high glucose, HEPES) medium supplemented with heat-inactivated fetal bovine serum (Gibco), penicillin, streptomycin, amphotericin B and L-glutamine were seeded into the upper compartments of a six-well transwell plate (Corning). The lower compartments contained 3.0 mL of the same medium. Cells were incubated at 37° C. in a 5% $CO_2$ atmosphere until 3 days post-confluence, washed with Hanks' solution to remove antibiotics and FCS and stepped down in DMEM supplemented with L-glutamine, sodium selenite and transferrin for 24 h without antibiotics. Transwell inserts were then transferred to an anaerobic culture box within the anaerobic workstation at 37° C. The upper compartment of each insert was filled with anaerobic DMEM cell medium, while the lower compartment was filled with oxygenated DMEM.

R. hominis A2-183 culture was harvested at exponential phase by centrifugation at 3,500×g for 5 min. The pellet was washed and resuspended in 0.8 mL anaerobic DMEM. One hundred microliters of bacterial suspension ($10^8$ CFU/mL) was added to experimental wells. The control wells received the same amount of medium without bacterial cells. Additional control included bacterial cells incubated without Caco-2 or HT29 cells.

Bacterial and eukaryotic cells were harvested after 2 h and 4 h incubation. Both non-adherent and adherent bacteria were aspirated and stored in RNAlater. The viability of R. hominis cells was tested by plating onto YCFA plates. Caco-2 cells or HT-29 cells were harvested from the wells and also stored in RNAlater. R. hominis Library Construction R. hominis chromosomal DNA for small-size library construction and pyrosequencing was isolated using an UltraClean™ Microbial DNA Isolation Kit (Mo Bio Laboratories Inc) and high-molecular-weight DNA for fosmid libraries was isolated using a Wizard Genomic DNA Purification kit (Promega). DNA integrity was checked by gel electrophoresis.

DNA was mechanically sheared using a Nebulizer kit (Invitrogen) and fractionated by gel electrophoresis. DNA fragments of desired size were excised from the gel and purified using a Wizard® SV Gel and PCR Clean-Up System (Promega). End-repair was done with a DNA Terminator End Repair Kit (Lucigen). 1.5-3.5 kb fragments were cloned using the CloneSmart® LCAmp kit (Lucigen) and a 4-8 kb library was constructed using the pJAZZ®-OC vector (Lucigen). Fosmid libraries were constructed using the CopyControl™ Fosmid Library Production Kit (Epicentre Biotechnologies). Colonies were picked using an automated colony picker (BioRobotics BioPick, Genomic Solutions) and archived into 384-well microtitre plates containing 70 µL 2×LB medium supplemented with 10% glycerol and corresponding antibiotic. Cells were grown overnight at 37° C. with shaking and stored at −80° C.

Sequencing, Assembly, and Annotation

Templates for sequencing of small-size libraries were generated by PCR using one µL of clone biomass and primers SL1 and SR2 surrounding the cloning site of pSMART-LCAmp. PCR products were purified using MUL- TISCREEN® PCR Clean-up filter plates (Millipore). Recombinant DNA from the pJAZZ®-OC clones was isolated using the WIZARD® SV 96 Plasmid DNA Purification System (Promega). Fosmid DNA was isolated using the FosmidMAX FOSMIDMAX™ DNA Purification Kit (Epicentre). End-reads of DNA fragments from R. hominis WGS libraries with different insert sizes were obtained using CEQ8000 (Beckman Coulter) and ABI 3770 (Applied Biosystems) DNA sequencers. Genomic DNA from R. hominis was also sequenced using 454 GS20 (454 Life Sciences) and 454 FLX sequencers (Roche). The Sanger and 454 data were assembled with MIRA version 3; (35). The RAST annotation pipeline was used for automatic and manual annotation of the genome and for comparative genomic analyses. The annotated genomic sequence of R. hominis A2-183 was submitted to GenBank under the accession number CP003040. Microarray Analyses Bacterial Microarray.

Bacterial RNA was isolated from mouse caecum contents using the RNeasy mini kit, and further processed with the MICROBEnrich™ kit (Ambion), the MICROBExpress™ bacterial mRNA enrichment kit (Ambion), and the MessageAmp™ II-bacteria RNA amplification kit (Applied Biosystems). RNA was labeled with either dCTP-Cy3 or dCTP-Cy5 during eDNA synthesis (CyScribe First strand eDNA labelling kit; Amersham). Labeled products were purified using the CyScribe GFX purification kit (Amersham). PCR products amplified from 6000 clones in the RA8 library were arrayed in duplicate on amino silane-coated microscope slides (Coming) using a MicroGrid II TAS (BioRobotics). Amplified fragments of the housekeeping genes rpoD and gyrA were randomly distributed on the array as controls. Microarray hybridization was performed in the GeneTAC hybridization station (Genomic Solutions). Dye labeling was swapped for a second hybridization, and a separate RNA purification was also labeled and hybridized twice, to ensure reproducibility and to obtain statistically significant results. In total, four slides were hybridized for each comparison, for a total of 12 hybridizing spots per amplified clone. Fluorescence was measured in two channels using a GeneTAC LS IV (Genomic Solutions) with GeneTac Integrator version 3.0.1 software. Spot intensities were log-transformed and Loess normalization was applied to remove differences in probe labelling and hybridization efficiencies. One-sample t-tests were used on the log-ratio values to test for differential expression. Data was considered significant when fold change >2 and $P<0.05$. Mouse Microarray Analysis Ileum and ascending colon tissue was removed from RNA later and lyzed in TRIZOL® (Invitrogen). RNA was isolated using standard chloroform/isopropanol steps. Total RNA was further purified with the RNEASY® kit (Qiagen), including an RNase-free DNase I (Qiagen) digestion step. RNA integrity was determined using the Agilent 2100 Bioanalyzer (Agilent Technologies). Total RNA was processed into biotin-labeled eRNA using the One-Cycle Target Labeling Kit (Affymetrix). Hybridization to the GENECHIP® Mouse Genome Array (Affymetrix) on a GENECHIP® Fluidics Station 450 (Affymetrix) was performed at the Institute of Medical Sciences Micro array Core Facility (University of Aberdeen, UK). Chips were scanned with an Affymetrix GENECHIP® Scanner 3000 (Affymetrix). Image quality analysis was performed using GENECHIP® Operating Software (GCOS) (Affymetrix). Further data analysis was performed with the freely available software packages R and Bioconductor. The moderated F-test provided by the Bioconductor package limma was used to test for differential expression. Data was considered significant when $P<0.05$ using the Benjamini and Hochberg false discovery method. Statistical analysis was performed separately for each of the two time-points. All differentially expressed genes ($P<0.05$) were imported into Meta Core analytical software (GeneGo, St Joseph, Mich.) to generate pathway maps. Integrated pathway enrichment analysis was performed using the knowledge-based canonical pathways and endogenous metabolic pathways. Ranking of relevant integrated pathways was based on p-values calculated using hypergeometric distribution. P-values represented the probability of a given number of genes from the input list to match a certain number of genes in the map by chance, considering the numbers of genes in the experiment versus the number of genes in the map within the full set of all genes on maps. Gene Ontology (GO) based functional interpretation of the data was performed using DAVID, an expanded version of the original web-accessible program (37). Significantly different transcripts ($P<0.05$) were allocated into the GO category 'Biological Process' to unearth patterns of gene expression significantly enriched for specific GO terms.

Microarray data were submitted to the National Center for Biotechnology Information (NCBI) Gene Expression Omnibus (accession number GSE25544). RT-PCR Analysis Bacterial PCR primers were designed using the online tool Primer3Plus (38) and purchased from Sigma-Aldrich. Real-time PCR analysis was performed using a 7500 Fast Real-Time PCR System (Applied Biosystems) with the Power SYBR Green PCR Master Mix (Applied Biosystems). PCR was performed as follows: one cycle at 95° C. for 10 min, followed by 40 cycles at 95° C. for 15 sec and 60° C. for 1 min, ending with a dissociation step. All samples were run in triplicate. GyrA was used as a reference gene for normalization due to its low variation between samples.

For host gene expression, 2 fig of total eukaryotic RNA isolated from the ileum and ascending colon was reverse-transcribed into eDNA using the High Capacity eDNA Reverse Transcription Kit (Applied Biosystems) with random primers. Real-time PCR analysis was performed using a 7500 Fast Real-Time PCR System (Applied Biosystems) with the QuantiFast SYBR Green PCR Kit (Qiagen) and QuantiTect Primer Assays (Qiagen). PCR cycling conditions were as follows: one cycle at 95° C. for 5 min, followed by 40 cycles at 95° C. for 10 sand at 60° C. for 30 s, ending with a dissociation step. All samples were run in triplicate. Hprt was selected as a reference gene for normalization because of its low variation between samples. All RT-PCR data were analyzed on a logarithmic scale with base 2 by Student's t test allowing unequal variances with a significance cut-off of $P<0.05$. Differences were back-transformed to calculate fold changes.

Western Blot

Immuno-purified rabbit polyclonal antibodies against *Roseburia hominis* Fla2 was produced as described in Duck et al (39). In brief, New Zealand white female rabbits were immunized with synthetic peptide in complete Freund's adjuvant and boosted several times. For *R. hominis* fla2 peptide 261-275 (SEQ ID NO: 1: C-AQYND-DAKSVLEILK-COOH) and peptide 58-71 (SEQ ID NO:2: C-GLNKASRNSQDGIS-CONH$_2$) were used. Following immunization the antibodies were purified on an immuno-affinity column prepared by coupling the peptides to 1 mL of activated SEPHAROSE® beads For the western blot, ascending colon gut contents were suspended in Iaemmli buffer containing 8M urea. *R. hominis* biomass (positive control) was diluted in the same buffer.

Thirty μL of each sample was loaded into wells of a NuPAGE® Novex® 4-12% Bis-Tris gel (Invitrogen) and electrophoresed, followed by further processing using the WesternBreeze Chemiluminescent Immunodetection System (Invitrogen). Fla2 antibody was diluted 1:1000 in antibody diluent and incubated overnight at 4° C., followed by 1 h at room temperature with alkaline phosphatase conjugated anti-rabbit. Detection was accomplished using the Fuji LAS3000 image system. Dry Body Weight and Lipid Carcass Analysis Eviscerated mouse carcass was weighed, lyophilized to constant weight and then milled for analysis. Lipid content was determined by extraction (1:100 w/v) with chloroform/methanol (2:1 v/v) as described previously (40).

FISH Analysis

FISH analysis was performed on gut tissue sections using a general bacterial probe Eub338 and a newly designed R. hominis A2-183-specific probe.

Tissues fixed in neutral buffered formalin were embedded in Technovit 8100 (Heraeus Kulzer). Two-micron sections were cut using a rotary microtome (Leica/Reichert Autocut). Three sections were taken per slide at 100 μm, 200 μm and 300 μm into the tissue, resulting in nine sections per animal.

Slides were dehydrated by consecutive incubation in 50% (v/v), 80% and 96% ethanol and dried at room temperature. 16S rRNA FISH probes used were a general bacterial probe Eub338 (SEQ ID NO:3: GCTGCCTCCCGTAGGAGT; Cy3) and a newly designed R. hominis A2-183-specific probe (SEQ ID NO: 4: GTACATTACATACTCTGTCAGTG; FITC), which was extensively tested for specificity against a panel of intestinal bacterial isolates. Ten microliter probe (30 ng/μL) in 100 μL hybridization buffer was applied to the dehydrated sample and incubated at probe-specific temperature. The slides were washed in washing buffer at 50° C. for 30 min, dipped in ice-cold water to remove residual washing buffer and dried under compressed air flow. Counterstaining was performed with 4',6-1.5 diamidino-2-phenylindole (DAPI; Vector Laboratories Inc) and slides were mounted with VECTASHIELD® Mounting Medium for fluorescence (Vector Laboratories Inc) to prevent fading. Bacteria were visualized using a Leica DM RBE fluorescence microscope (Leitz GMBH) and photographed with a Penguin 600CL camera (Pixera) and VIEWFINDER™ 3.0 software (Studio Lite). High-magnification images (×63) were retrieved using the Apochromatics system (Leica).

Immunofluorescence

Immuno-localization of T cell markers was examined on sequential cryosections (8 11 m). Sections were fixed either in pre-cooled methanol for 30 min at −20° C. (Ly6G FITC, CD3 FITC, CD 11 b FITC, all at 1:50 (BD Biosciences)), or, for the double-labeled FoxP3 (1:500, Abeam) with CD3 FITC (1:100, BD Biosciences) fixed in 1% paraformaldehyde (PFA) for 2 min at RT followed by 3 min in 0.01% TRITON® X in PBS. All sections were blocked with 10% BSA (Sigma) containing 10% relevant pre-immune sera in PBS (pH 7.4). Methanol-fixed tissues were incubated with primary antibodies for 1 h at RT. PFA-fixed sections were incubated with antibodies over night at 4° C. FoxP3 was visualized using Alexa goat anti rabbit 594 (1:1000, Molecular Probes). Sections were counter labeled with DAPI and mounted with VECTASHIELD® (Vector Laboratories). For quantification of positive cells, a minimum of five fields of view from each mouse section was examined, using imaging software and microscope settings described above. Histology Tissue samples were fixed for three hours in Carnoy's fixative (60% (v/v) ethanol, 30% (v/v) chloroform and 10% (v/v) glacial acetic acid) at room temperature with constant agitation. The samples were transferred to 70% ethanol and stored at room temperature until orientated for transverse sectioning and embedded in cold-curing resin using TECHNOVIT® 8100 (Heraeus Kulzer) according to the manufacturer's instructions. The embedded tissue was mounted onto Histoblocs using TECHNOVIT®3040 (Heraeus Kulzer). Four micron sections were cut using a rotary microtome (Leics Autocut) fitted with a glass knife (TAAB Laboratories Equipment Ltd.). Tissue sections were stained using standard haemotoxylin/eosin methods and examined with a Zeiss Axioskop microscope equipped with ×10 and ×20 objectives. Images were taken using a Qimaging camera and IMAGE PRO PLUS® software.

Comparison of Genomes of *Roseburia*-Related Species and Strains

The Applicant produced a complete genome sequence of R. hominis A2-183, which is represented by a single 3,592,125-bp chromosome. Automated and manual annotation of the genome using the RAST platform revealed the presence of four ribosomal operons, 66 RNAs and 3,273 predicted proteins. The Subsystem Category Distribution for R. hominis A2-183, R. inulinivorans DSM 16841, R. intestinalis L1-82, R. intestinalis M50/1 and *Eubacterium rectale* ATCC 33656 are shown in FIGS. 11-15 respectively.

This information illustrates the differences in number of genes (presented in brackets) in each functional subsystem. These genes are very important in mediating host response to each individual bacterium. Importantly these genes, both in number and function, are different between the various strains. The results are summarised below:

R. hominis A2-183
Cell Wall and Capsule (57)
Membrane Transport (24)
Motility and Chemotaxis (49)
Regulation and Cell signaling (16)
Dormancy and Sporulation (12)
Carbohydrates (271)
E. rectale ATCC 33656
Cell Wall and Capsule (41)
Membrane Transport (13)
Motility and Chemotaxis (16)
Regulation and Cell signaling (9)
Dormancy and Sporulation (6)
Carbohydrates (172)
R. intestinalis L1-82
Cell Wall and Capsule (35)
Membrane Transport (36)
Motility and Chemotaxis (15)
Regulation and Cell signaling (10)
Dormancy and Sporulation (17)
R. intestinalis M50/1
Cell Wall and Capsule (28)
Membrane Transport (37)
Motility and Chemotaxis (17)
Regulation and Cell signaling (10)
Dormancy and Sporulation (17) Carbohydrates (201)
R. inulinovorans DSM 16841
Cell Wall and Capsule (69)
Membrane Transport (26)
Motility and Chemotaxis (14)
Regulation and Cell signaling (9)
Dormancy and Sporulation (17)
Carbohydrates (160)

Percentage Sequence Identity of >3000 Genes Found in Contig 1 Highlights the Differences Between the Bacterial Genome of *R. hominis* and the Bacterial of *E. rectale*, *R. intestinalis* and *R. inulinivorans*

Comparisons were made between the genomes of various *Roseburia* species and the related species *Eubacterium rectale*, the closest relative to *R. hominis*.

*R. hominis* reference genome 585394.12
*E. rectale* genome ATCC336556 515619.3
*R. intestinalis* L1-82166486.4
*R. intestinalis* MS0/1166486.5
*R. inulinovorans* DSM16841 622312.3

The percentage identity of potential genes between the various *Roseburia* genomes ranges from 0% to around 90% sequence identity. Many genes are hypothetical and vary between the strains. Large numbers of genes are present in the *R. hominis* genomes that are absent from the genomes of the others *Roseburia* species

*Roseburia hominis* has 924 genes that are not found in the other genomes of other *Roseburia* species (0% identity) indicting that almost 25% of its genome is unique to *R. hominis*. Also the low homology between other genes (<10-70%) indicates that the functions of many others genes are also likely to differ.

The information provides compelling evidence that these bacteria are very different from a genome and functional perspective, and cannot be grouped other than by their phylogenetic relatedness, which is generally based on the conserved gene 16S ribosomal gene which is a conserved piece of prokaryotic DNA found in all bacteria. 16S rRNA gene sequences are used for bacterial phylogeny and taxonomy studies (shared genetic marker).

Figures 9, 10:
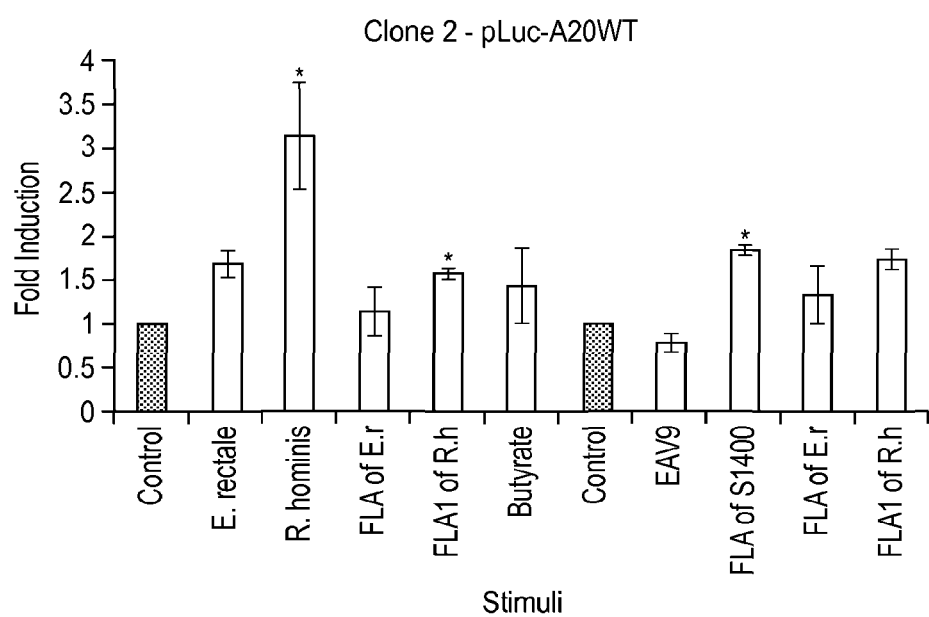
FIG. 9 illustrates a comparison of gene expression data for three strains of bacteria from Cluster XIVa (Firmicutes), namely *Roseburia hominis, E. rectale* and *Roseburia intestinalis*.
FIG. 10 shows that *Roseburia hominis* induces A20, a negative regulator of NF-KB signaling with potent anti-inflammatory activity, whereas other bacterial strains have no effect. The flagellin moiety of *Roseburia hominis* (FLA1 of *R. hominis*) also induces A20 unlike that of *Eubacterium rectale*, a related bacterium. In more detail.
Figure 11:
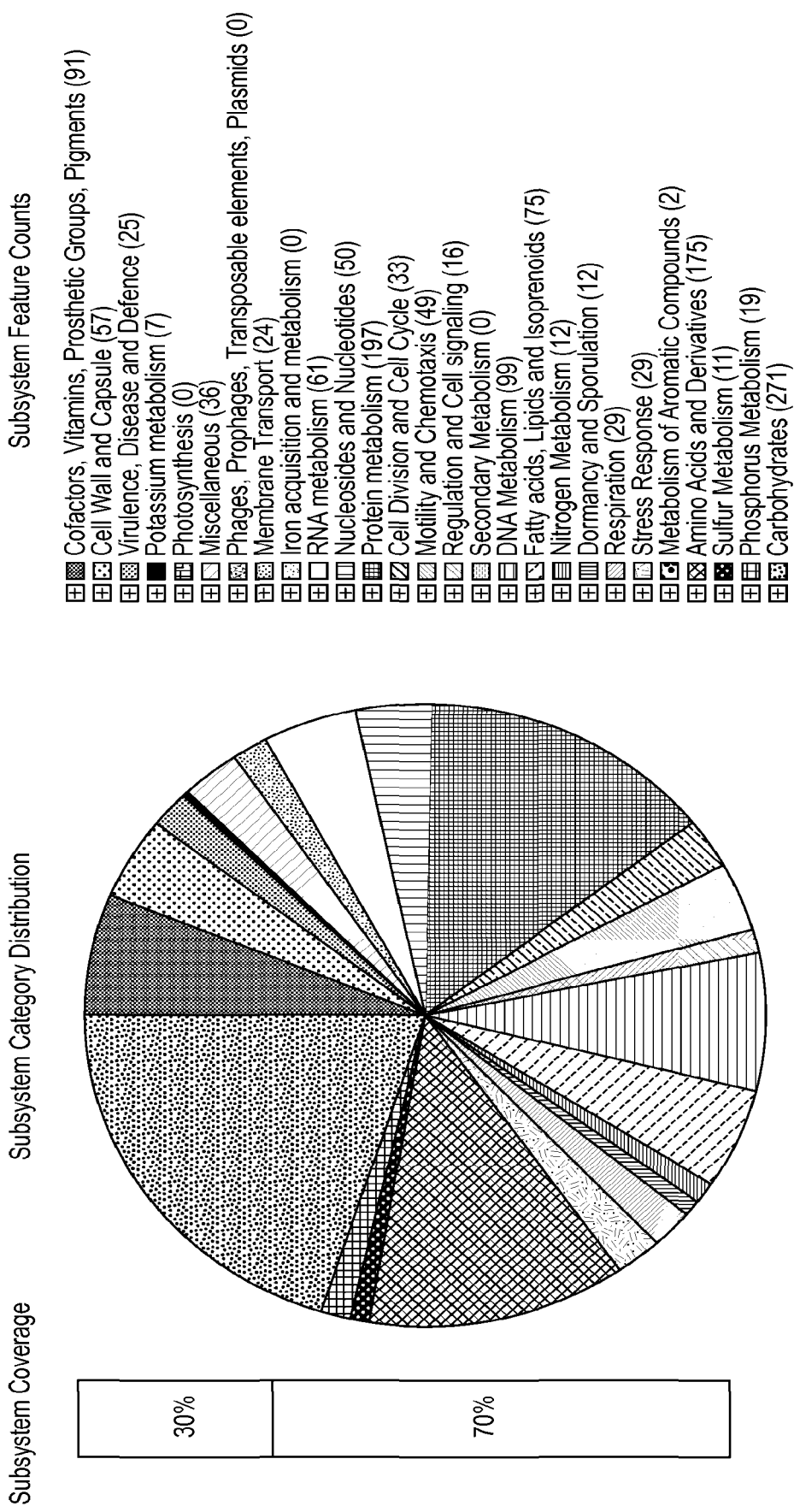
FIG. 11 shows the Subsystem Category Distribution for *R. hominis* A2-183 as determined by RAST, showing functional subsystems and the number of genes in each subcategory.
Figure 12:
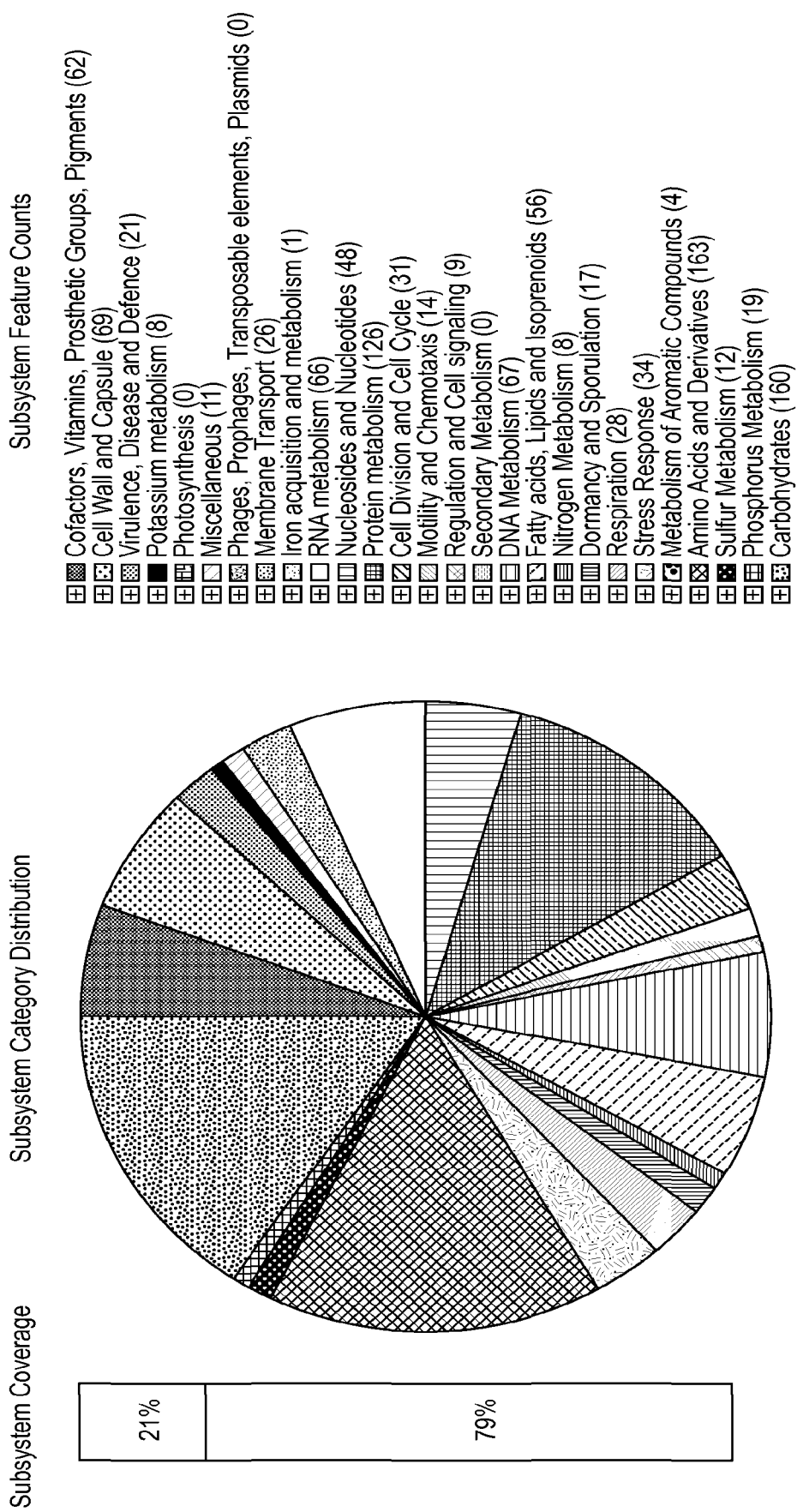
FIG. 12 shows the Subsystem Category Distribution for *R. inulinivorans* DSM 16841 A2-183 as determined by RAST, showing functional subsystems and the number of genes in each subcategory.
Figure 13:
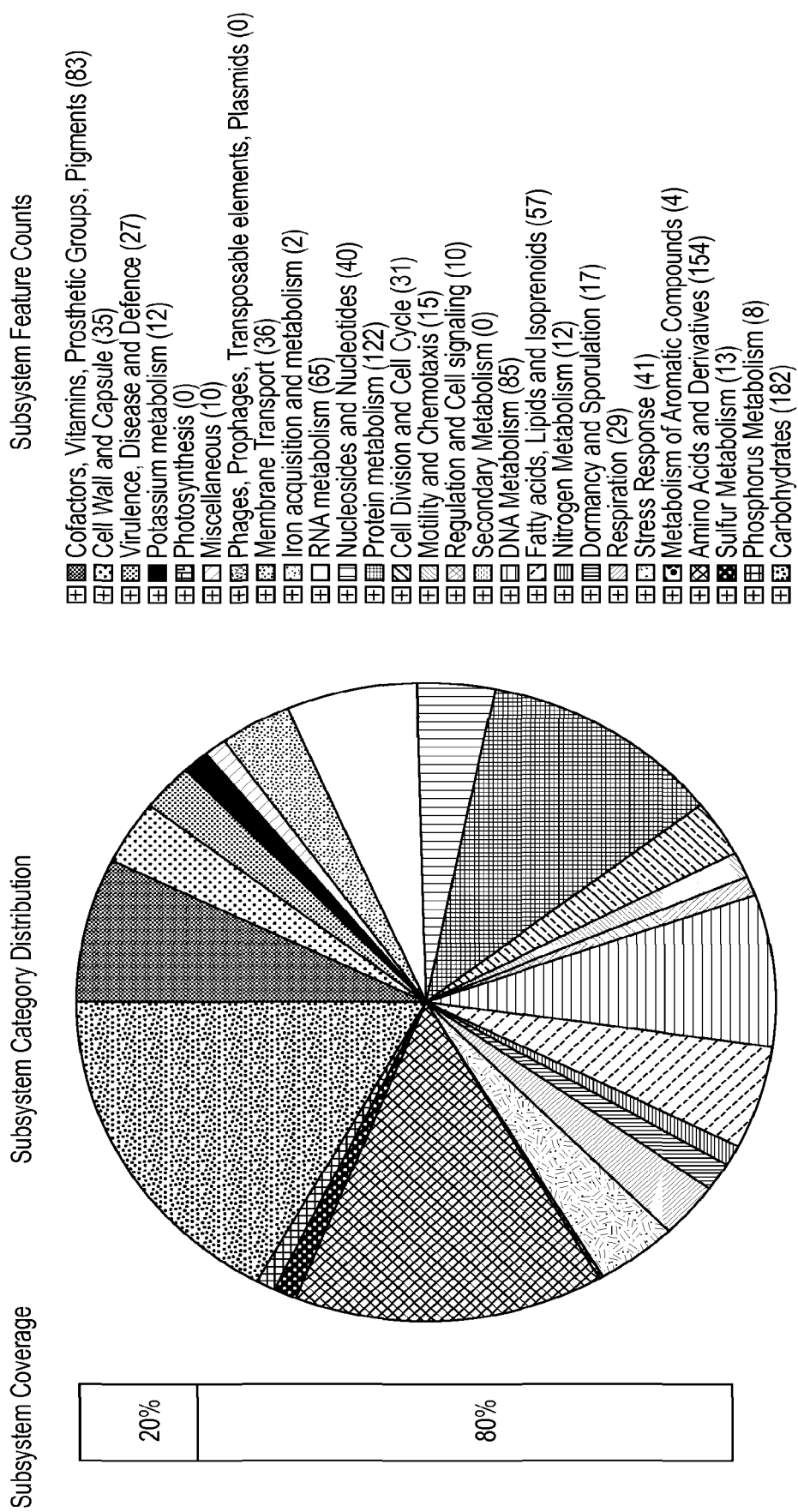
FIG. 13 shows the Subsystem Category Distribution for *R. intestinalis* L1-82 as determined by RAST, showing functional subsystems and the number of genes in each subcategory.
Figure 14:
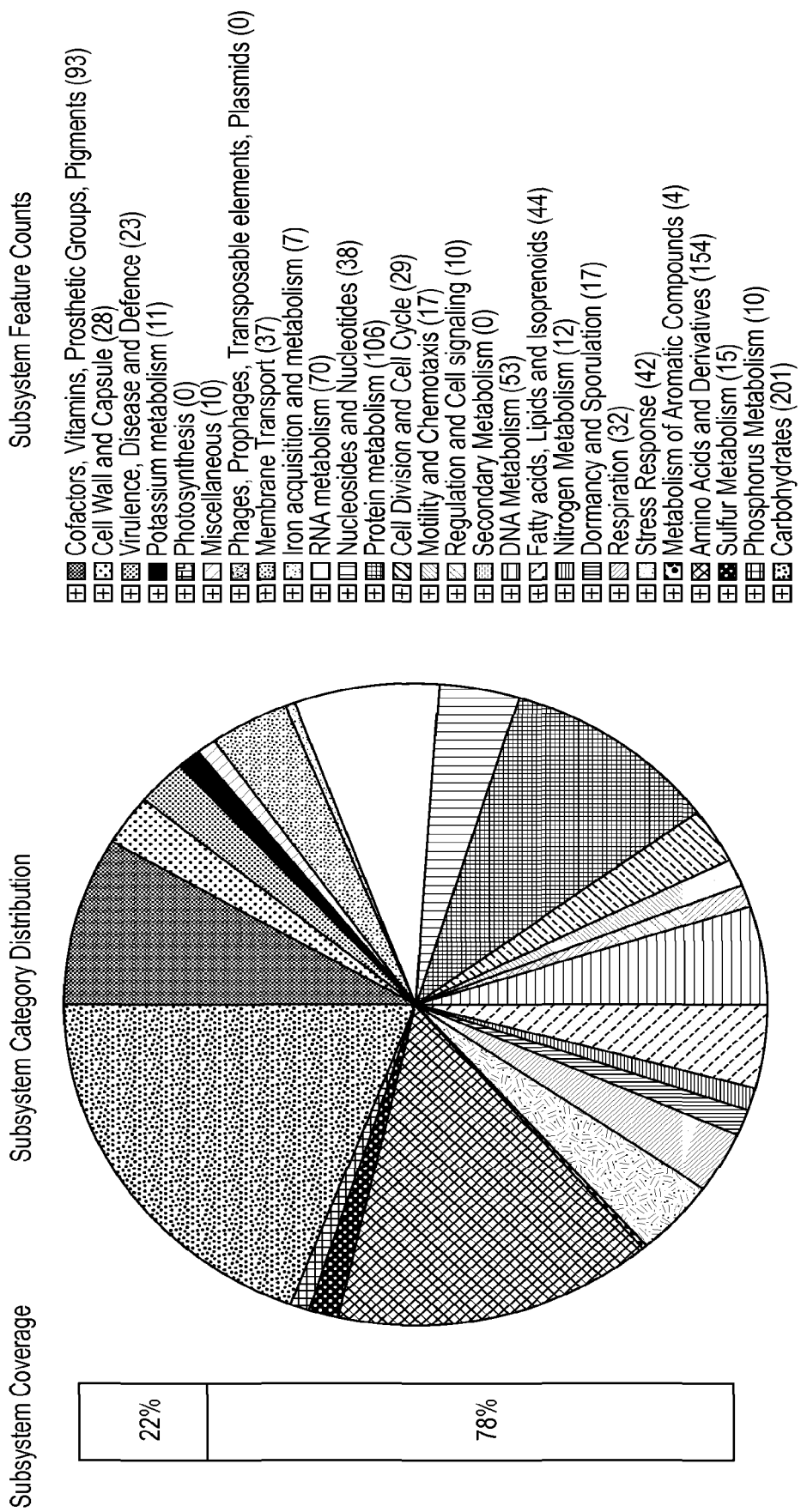
FIG. 14 shows the Subsystem Category Distribution for *R. intestinalis* M50/1 as determined by RAST, showing functional subsystems and the number of genes in each subcategory.
Figure 15:
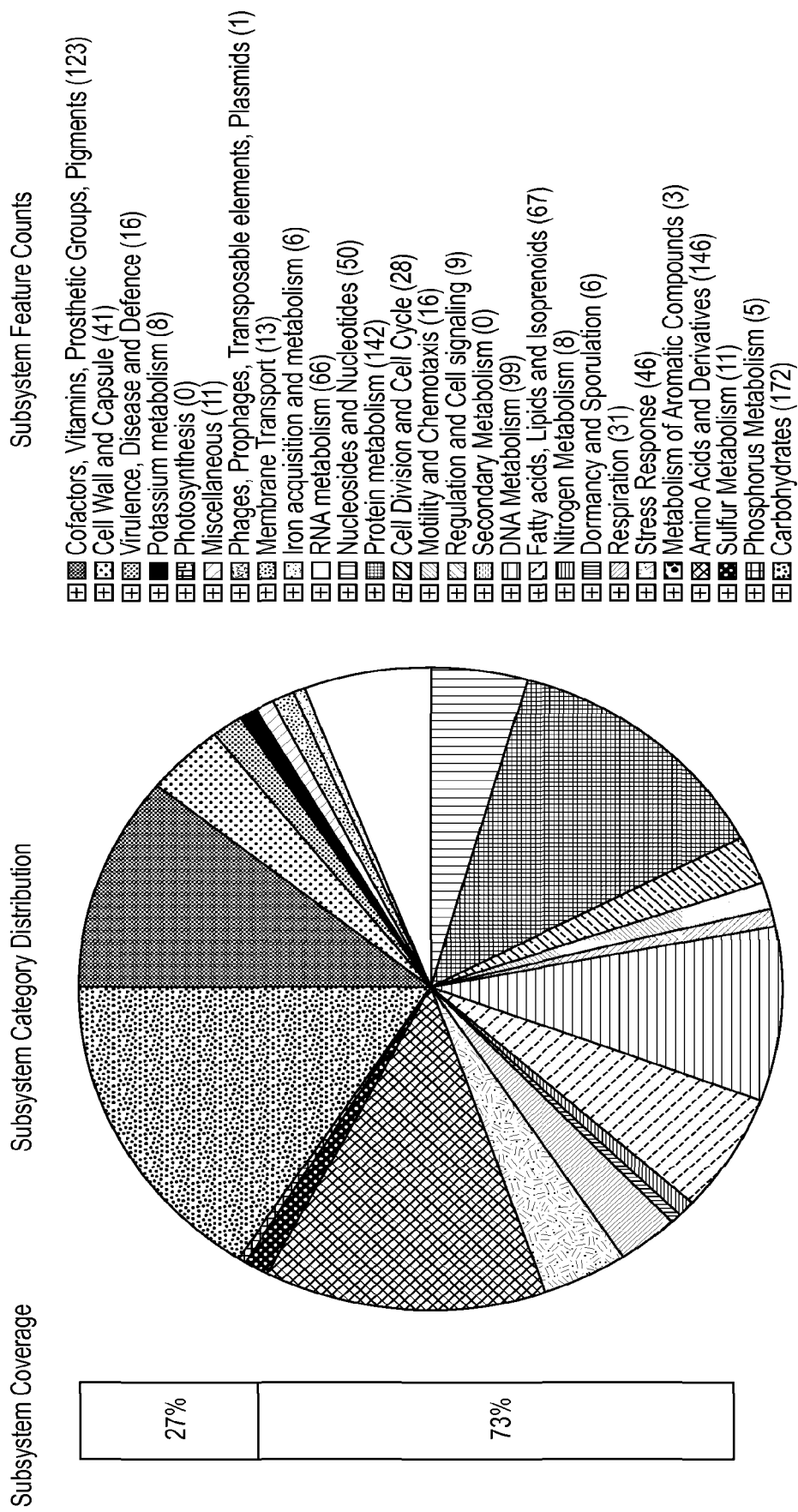
FIG. 15 shows the Subsystem Category Distribution for *Eubacterium rectale* ATCC 33656 as determined by RAST, showing functional subsystems and the number of genes in each subcategory.

Functionality in Relation to Host Response and Immunity is Bacterial Strain Specific FIG. 9 illustrates a comparison of gene expression data for three strains of bacteria from Cluster XIV a (Firmicutes), namely *Roseburia hominis, E. rectale* and *Roseburia intestinalis*. The data indicates the numbers of unique genes expressed by the phylogenetically related bacterial strains following exposure to human epithelial cells. Gene expression was determined by using Affymetrix human microarrays containing 56,000 genes. This difference reflects the differences in their respective genomes. [These experiments are similar to those described elsewhere in the specification using mouse microarrays but used specific human microarrays. The GENECHIP® Human Genome 0133 Plus 2.0 Array is the first and most comprehensive whole human genome expression array. The Affymetrix GENECHIP® Human Genome U133 Plus 2.0 Array (HG-U133 Plus 2.0) microarray comprises 1,300,000 unique oligonucleotide features covering over 47,000 transcripts and variants, which, in turn, represent approximately 3 9, 000 of the best characterized human genes. The cell lines used to evaluate the signalling responses induced by different commensal bacteria include the human colon cell line Caco-2 cells and HT-29 cells and bacteria including *R. hominis, E. rectale* and *R. intestinalis* where compared against *Salmonella enteritidis*, an enteric pathogen.

Functional Differences in Cluster XIV a Bacteria—Comparison Between *R. hominis* and *E. rectale*

FIG. 10 shows that *Roseburia hominis* induces A20 a negative regulator of NF-κB signaling with potent anti-inflammatory activity whereas other bacterial strains have no effect. The flagellin moiety of *Roseburia hominis* also induces A20 unlike that of *Eubacterium rectale*, a related bacterium.

Cell culture reagents, unless specified otherwise, were supplied by Sigma-Aldrich. Caco-2 (ECACC Cat No. 8601 02002) and HT29 (ATCC) cell lines cultured in Dulbecco's Modified Eagle Medium (DMEM) supplemented with 10% Foetal Bovine Serum (FBS) (Gibco, UK), 200 mM L-glutamine and 1% antibiotics/antimycotics were seeded in six-well transwell plate (Coming). Cells were incubated at 37° C. in a 5% CO2 atmosphere until 3 days post-confluence, washed with Hanks' solution to remove antibiotics and FCS and stepped down in DMEM supplemented with L-glutamine, sodium selenite and transferrin for 24 h without antibiotics. Transwell inserts were then transferred to an anaerobic culture box within the anaerobic workstation at 37° C. The upper compartment of each insert was filled with anaerobic DMEM cell medium, while the lower compartment was filled with oxygenated DMEM.

*Roseburia hominis* A2-183 and *E. rectale* ATCC336556 in standard YCFA and M2 culture media and *Salmonella* enteric serovar *enteritidis* cultured in LB broth were harvested at exponential phase by centrifugation at 3,500×g for 5 min. The pellet was washed and resuspended in anaerobic DMEM. One hundred microliters of bacterial suspension ($10^8$ CFU/mL) was added to experimental wells. The control wells received the same amount of medium without bacterial cells. Additional control included bacterial cells incubated without Caco-2 or HT29 cells.

Bacterial and eukaryotic cells were harvested after 2 h and 4 h incubation. Both non-adherent and adherent bacteria were aspirated and stored in RNALater. Caco-2 cells or HT-29 cells were harvested from the wells and also stored in RNALater.

Luciferase Assay for Determination of A20 Luciferase Gene Expression

FUGENE® 6 transfection reagent (Roche, UK) was used for the transfection of HT29 cells with the plasmids carrying the luciferase reporter gene under the control of the A20 promoter pLuc-A20 and pLuc-A2011 NF-KB (mutated in 3 nucleotides in the A20 promoter region) and the GFP reporter gene under the control of the A20 promoter pCAGGS-GFP\A20 and pLucGL2\NF-KB. After 48 h, the cells were stimulated with live bacteria *R. hominis, E. rectale* and *S. enteritidis* and recombinant flagellins; *S. enteritidis* and *R. hominis* (Fla 1) (100 ng/ml) for 9, 12 and 24 h. Recombinant flagellin were generated using full length sequences cloned into appropriate vectors and expressed in *E. coli* JM109, BL21 and Rosetta. Luciferase (Firefly-f-Lue and *renilla*-rLuc) activities were determined using the DUALGLO® luciferase assay system (Pro mega, UK) and an Envision 2102 Multilabel Reader. The relative luciferase reporter activity was obtained by normalization to *renilla* control.

Various modifications and variations of the described aspects of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes of carrying out the invention, which are obvious to those skilled in the relevant fields are intended to be within the scope of the following claims.

What is claimed is:

1. A composition that comprises a lyophilized *Roseburia* bacteria strain, wherein the *Roseburia* bacteria strain is the *Roseburia hominis* strain deposited under accession number NCIMB 14029, wherein the composition comprises from about $1\times10^6$ to about $1\times10^{11}$ colony forming units of the bacteria strain per gram (CFU/g) with respect to a weight of the composition; and an excipient, carrier or diluent, wherein the composition is a solid unit dose tablet or capsule formulation, and wherein the capsule is formulated for delivery of the *Roseburia* bacteria strain to a colon or an ileum when administered orally to a subject.

2. The composition of claim 1, wherein the composition produces a decrease in at least one pro-inflammatory cytokine when administered orally to the subject, wherein the decrease is in comparison to a corresponding subject not administered with the composition.

3. The composition of claim 1, wherein the composition comprises a carrier, wherein the carrier is selected from the group consisting of lactose, starch, glucose, methyl cellulose, magnesium stearate, mannitol, sorbitol, and combinations thereof.

4. The composition of claim 1, wherein the composition is an edible composition.

5. The composition of claim 1, wherein the composition is a probiotic composition.

6. The composition of claim 1, wherein the composition further comprises a prebiotic compound.

7. The composition of claim 6, wherein the prebiotic compound is a carbohydrate, inulin or a transgalacto-oligosaccharide.

8. The composition of claim 7, wherein the composition comprises the carbohydrate, and wherein the carbohydrate is selected from the group consisting of: fructo-oligosaccharides; short-chain fructo-oligosaccharides; isomalt-oligosaccharides; pectins; xylooligosaccharides; chitosan-oligosaccharides; beta-glucans; arable gum modified and resistant starches; polydextrose; D-tagatose; acacia fibers; carob; oats; and citrus fibers.

9. The composition of claim 6, wherein the prebiotic compound is in an amount of from about 1% to about 20% by weight with respect to a total weight of the composition.

10. The composition of claim 1, wherein the composition further comprises at least one additional bacterium.

11. The composition of claim 10, wherein the at least one additional bacterium is a food grade bacterium.

12. The composition of claim 11, wherein the food grade bacterium is selected from the group consisting of lactic acid bacteria, bifidobacteria, propionibacteria, and mixtures thereof.

13. The composition of claim 1, further comprising an oxygen scavenger.

* * * * *